US011166479B2

(12) United States Patent
Miller et al.

(10) Patent No.: US 11,166,479 B2
(45) Date of Patent: Nov. 9, 2021

(54) FEEDSTUFFS FOR AQUACULTURE COMPRISING STEARIDONIC ACID

(71) Applicants: Matthew Robert Miller, Atawhai (NZ); Christopher Guy Carter, Howden (AU); Peter David Nichols, West Hobart (AU); Surinder Pal Singh, Downer (AU); Xue-Rong Zhou, Harrison (AU); Allan Graham Green, Cremorne Point (AU)

(72) Inventors: Matthew Robert Miller, Atawhai (NZ); Christopher Guy Carter, Howden (AU); Peter David Nichols, West Hobart (AU); Surinder Pal Singh, Downer (AU); Xue-Rong Zhou, Harrison (AU); Allan Graham Green, Cremorne Point (AU)

(73) Assignee: COMMONWEALTH SCIENTIFIC AND INDUSTRIAL RESEARCH ORGANISATION, Acton (AU)

( * ) Notice: Subject to any disclaimer, the term of this patent is extended or adjusted under 35 U.S.C. 154(b) by 420 days.

(21) Appl. No.: 15/833,826

(22) Filed: Dec. 6, 2017

(65) Prior Publication Data
US 2018/0103659 A1      Apr. 19, 2018

Related U.S. Application Data

(60) Division of application No. 14/298,399, filed on Jun. 6, 2014, now abandoned, which is a continuation of
(Continued)

(30) Foreign Application Priority Data

Nov. 17, 2006   (WO) ............... PCT/AU2006/001737

(51) Int. Cl.
A23K 20/158       (2016.01)
A01K 61/10        (2017.01)
(Continued)

(52) U.S. Cl.
CPC ............ *A23K 20/158* (2016.05); *A01K 61/10* (2017.01); *A01K 61/80* (2017.01); *A01K 67/027* (2013.01);
(Continued)

(58) Field of Classification Search
CPC .... A23K 20/158; A23K 50/80; A23K 20/142; A23K 50/10; A01K 2227/70;
(Continued)

(56) References Cited

U.S. PATENT DOCUMENTS 4,945,050 A     7/1990  Sanford et al.
5,004,863 A     4/1991  Unibeck et al.
(Continued)

FOREIGN PATENT DOCUMENTS

CA        2563470 A1 * 11/2005 ........... A23K 20/158
WO     WO 1987/006614      11/1987
(Continued)

OTHER PUBLICATIONS

Bell et al., "Substituting Fish Oil with Crude Palm Oil in the Diet of Atlantic Salmon (*Salmo salar*) Affects Muscle Fatty Acid Composition and Hepatic Fatty Acid Metabolism". The Journal of Nutrition 132:222-230, 2002) (Year: 2002).*
(Continued)

*Primary Examiner* — Erik Kashnikow
*Assistant Examiner* — Assaf Zilbering
(74) *Attorney, Agent, or Firm* — Gary J. Gershik

(57) ABSTRACT

The present invention relates to feedstuffs for use in aquaculture, as well as methods for producing said feedstuffs. The invention also provides methods for rearing fish and/or
(Continued)

Figure 1:
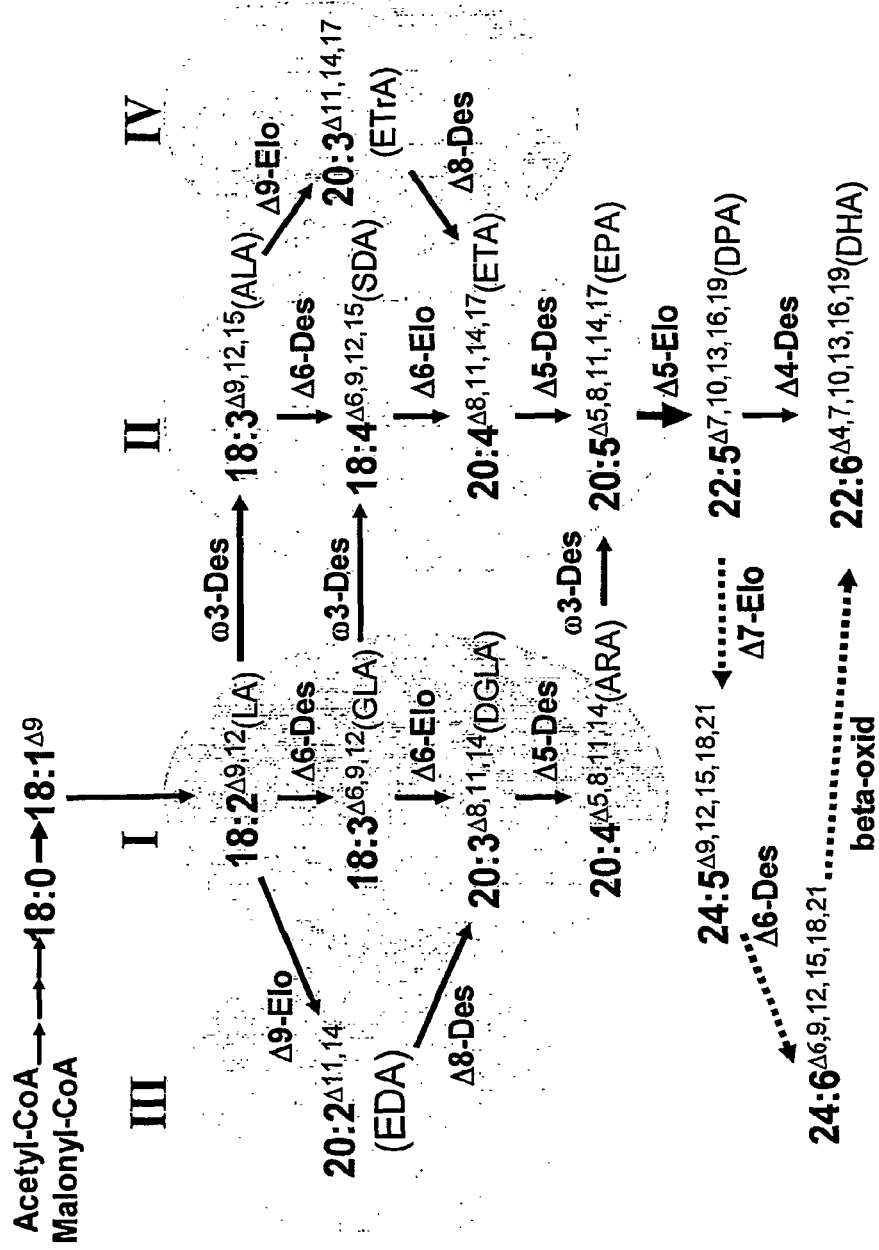

crustaceans. In particular, the present invention provides a method of rearing a fish or crustacean, the method comprising feeding the fish or crustacean a feedstuff comprising lipid, the fatty acid of said lipid comprising at least 5.5% (w/w) stearidonic acid (SDA).

22 Claims, 2 Drawing Sheets

Specification includes a Sequence Listing.

Related U.S. Application Data application No. 12/085,261, filed as application No. PCT/AU2006/001737 on Nov. 17, 2006, now Pat. No. 8,795,744.

(60) Provisional application No. 60/737,946, filed on Nov. 18, 2005.

(51) Int. Cl.
| | |
|---|---|
| *A01K 61/80* | (2017.01) |
| *A23K 50/10* | (2016.01) |
| *A23K 50/80* | (2016.01) |
| *A01K 67/027* | (2006.01) |
| *A23K 20/147* | (2016.01) |
| *A23K 20/142* | (2016.01) |
| *A23K 50/75* | (2016.01) |
| *C12P 7/64* | (2006.01) |
| *C12N 15/82* | (2006.01) |
| *C12N 9/02* | (2006.01) |
| *C12N 9/10* | (2006.01) |

(52) U.S. Cl.
CPC .............. *A23K 50/10* (2016.05); *A23K 50/80* (2016.05); *C12N 15/8247* (2013.01); *C12P 7/6472* (2013.01); *A01K 2227/40* (2013.01); *A01K 2227/70* (2013.01); *A01K 2267/02* (2013.01); *A23K 20/142* (2016.05); *A23K 20/147* (2016.05); *A23K 50/75* (2016.05); *C12N 9/0083* (2013.01); *C12N 9/1029* (2013.01); *Y02A 40/81* (2018.01); *Y02A 40/818* (2018.01); *Y10S 426/805* (2013.01)

(58) Field of Classification Search
CPC ...... A01K 61/10; A01K 61/80; A01K 67/027; A01K 2267/02; A01K 2227/40; A01K 61/00; C12N 9/0083; C12N 9/1029; C12N 15/8247; Y02A 40/81; Y02A 40/818; Y10S 426/805
See application file for complete search history.

(56) References Cited

U.S. PATENT DOCUMENTS

| | | | |
|---|---|---|---|
| 5,104,310 A | 4/1992 | Saltin et al. | |
| 5,141,131 A | 8/1992 | Miller et al. | |
| 5,159,135 A | 10/1992 | Urnbeck et al. | |
| 5,177,010 A | 1/1993 | Goldman et al. | |
| 5,384,253 A | 1/1995 | Krzyzek et al. | |
| 5,472,869 A | 12/1995 | Krzyzek et al. | |
| 5,504,200 A | 4/1996 | Hall et al. | |
| 5,608,152 A | 3/1997 | Kridl et al. | |
| 5,698,246 A | 12/1997 | Villamar et al. | |
| 8,173,870 B2 | 5/2012 | Ursin et al. | |
| 8,221,819 B2 | 7/2012 | Ursin et al. | |
| 8,795,744 B2 | 8/2014 | Miller et al. | |
| 2003/0017231 A1 | 1/2003 | Hjaltason et al. | |
| 2003/0124218 A1 | 7/2003 | Hjaltason et al. | |
| 2003/0159173 A1 | 8/2003 | Wolter et al. | |
| 2004/0022923 A1 | 2/2004 | Hjaltason et al. | |
| 2009/0299083 A1 | 12/2009 | Miller et al. | |

FOREIGN PATENT DOCUMENTS

| | | | | |
|---|---|---|---|---|
| WO | WO 1991/003980 | 4/1991 | | |
| WO | WO 1992/009696 | 6/1992 | | |
| WO | WO 1993/021335 | 8/1993 | | |
| WO | WO 1995/015389 | 6/1995 | | |
| WO | WO 1995/023230 | 8/1995 | | |
| WO | WO 1998/045461 | 10/1998 | | |
| WO | WO 1999/016890 | 4/1999 | | |
| WO | WO 2000/042195 | 7/2000 | | |
| WO | WO 2002/081668 | 10/2002 | | |
| WO | WO 2002/092073 A1 | 11/2002 | | |
| WO | WO 2002/092540 A1 | 11/2002 | | |
| WO | WO 2003/099216 A2 | 12/2003 | | |
| WO | WO 2005/021761 A1 | 3/2005 | | |
| WO | WO-2005021761 A1 * | 3/2005 | ......... | C12N 15/8247 |
| WO | WO 2005/102310 A1 | 11/2005 | | |
| WO | WO 2006/028839 A2 | 3/2006 | | |

OTHER PUBLICATIONS

Ruinan et al., "Phytosterol Contents of Edible Oils and Their Contributions to Estimated Phytosterol Intake in the Chinese Diet". Foods, 8, 334 (2019)) (Year: 2019).*
Torstensen et al., "Lipid Metabolism and Tissue Composition in Atlantic Salmon (*Salmo salar* L.)—Effects of Capelin Oil, Palm Oil, and Oleic Acid-Enriched Sunflower Oil as Dietary Lipid Source". Lipids, vol. 35, No. 6 (2000), 652-664 (Year: 2000).*
Jul. 9, 2018 English translation of Response to First Office Action issued in connection with Norwegian Patent Application No. 20082797.
Jul. 5, 2019 Notice of Opposition and its English translation issued in connection with corresponding European Patent No. 1965658.
Communication Pursuant to Article 94(3) EPC dated Sep. 26, 2016 in connection with European Patent Application No. 06817510.8.
Good, Joanne Elizabeth, "Replacement of dietary fish oil with vegetable oils: effects on fish health", 2004, University of Stirling, "Culture of Altantic cod (*Gadus morhua*) juveniles and Artic char (*Salvelinus alpinus*) on diets containing Echium oil: effects on fish health and immune function", pp. 264-304.
Anonymous, "feedstuff—Definition from the Merriam-Webster Online Dictionary", Apr. 24, 2009, http://web.archive.org/web/20090424031405/http://www.merriam-webster.com/dictionary/feedstuff.
Wood, Cathryn E, "Premarket Notification for a New Dietar Ingredient, Echium oil", Jan. 1, 2002, http://www.fda.gov/ohrms/dockets/dockets/95s0316/95s-0316-rpt0147-03-vol105.pdf.
Ursin, Viginia M., "Symposium: Improving Human Nutrition through Genomics, Proteomics and Biotechnologies Modification of Plant Lipids for Human Health: Development of Functional Land-Based Omega-3 Fatty Acids 1", Apr. 11, 2003, The Journal of Nutrition 133: 4271-4274.
I.P Forster et al., "Rendered meat and bone meals as ingredients of diets for shrimp*Litopenaeus vannamei* (Boone, 1931)", Apr. 1, 2003, Aquaculture 219(1-4):655-670.
Carole Blanchet et al., "Fatty acid composition of wild and farmed Atlantic salmon (*Salmon salar*) and rainbow trout (*Oncorhynchus mykiss*)" May 1, 2005, Lipids 40(5): 529-531.
Sep. 27, 2016 Third Party Observations, filed in connection with European Patent Application No. 06817510.8, including English Language Translation.
Response to the Apr. 19, 2016 Fourth Examination Report filed for Canadian patent application 2,630,173.
Apr. 15, 2014 Office Action, issued in connection with Canadian Patent Application No. 2,630,173.
Oct. 15, 2014 Response to Office Action, filed in connection with Canadian Patent Application No. 2,630,173.
Apr. 8, 2015 Third Office Action, issued in connection with Canadian Patent Application No. 2,630,173.

(56) References Cited

OTHER PUBLICATIONS

Oct. 6, 2015 Response to Third Office Action, filed in connection with Canadian Patent Application No. 2,630,173.

Apr. 19, 2016 Fourth Office Action, issued in connection with Canadian Patent Application No. 2,630,173.

Eckert et al., (2006) Co-Expression of Borage Delta-6 Desaturase and Arabidopsis Delta-5 Desaturase Results in High Accumulation of Stearidonic Acid in the Seeds of Transgenic Soybean. Planta, 224: 1050-1057.

International Search Report issued by the International Searching Authority (ISA/AU) dated Feb. 27, 2007 in connection with International Application No. PCT/AU2006/001737.

International Preliminary Report on Patentability issued by the International Bureau of WIPO dated May 20, 2008 in connection with PCT International Application No. PCT/AU2006/001737.

Written Opinion of the International Searching Authority issued by the International Searching Authority (ISA/AU) dated Feb. 27, 2007 in connection with PCT International Application No. PCT/AU2006/001737.

Phleger, C.F. et al. "Lipids and nutrition of the southern rock lobster, *Jasus edwardsii*, from hatch to puerulus" Mar. Freshwater Res., 2001, 52:1475-86.

Opsahl-Ferstad, H.-G. et al. "Biotechnological approaches to modify rapeseed oil composition for applications in aquaculture" Plant Science, 2003, 165:349-357.

Miller, M.R. et al. "Regiospecificity Profiles of Storage and Membrane Lipids from the Gill and Muscle Tissue of Atlantic Salmon (*Salmo salar* L.) Grown at Elevated Temperature" Lipids, 41(9):865-876.

Bayir, A. et al. "Fatty acid composition in some selected marine fish species living Turkish waters" J. Sci. Food Agric., 2006, 86:163-168.

Kiessling, A. et al. "Effects of Reduced Feed Ration Levels on Fat Content and Fatty Acid Composition in White and Red Muscle from Rainbow Trout" Aquaculture, 1989, 79:169-175.

Njinkoué, J-M. et al. "Lipids and fatty acids in muscle, liver and skin of three edible fish from the Senegalese coast: *Sardinella maderensis, Sardinella aurita* and *Cephalopholis taeniops*" Comp. Biochem. Physio. Part B, 2002, 131:395-402.

Bell, J.G. et al. "Substituting Fish Oil with Crude Palm Oil in the Diet of Atlantic Salmon (*Salmo salar*) Affects Muscle Fatty Acid Composition and Hepatic Fatty Acid Metabolism" The J. of Nutrition, 132:222-230.

Phleger, C.F. et al. "Interannual and between species comparison of the lipids, fatty acids and sterols of Antarctic krill from the US AMLR Elephant Island survey area" Comp. Biochem. Physio. Part B, 2002, 131:733-747.

Kim, J.D. et al. "Effects of Dietary Lipid to Protein Ratios on the Fatty Acid Composition of Muscle Lipids in Rainbow Trout" Nutrition Rep. Inter., Jul. 1989, 40(1):9-16.

Nordgarden, U. et al. "Seasonally changing metabolism in Atlantic salmon (*Salmo salar* L.) II—β-oxidation capacity and fatty acid composition in muscle tissues and plasma lipoproteins" Aquaculture Nutr., 2003, 9:295-303.

Haliloğlu, H.I. et al. "Comparison of fatty acid composition in some tissues of rainbow trout (*Oncorhynchus mykiss*) living in seawater and fresh water" Food Chem., 2004, 86:55-59.

Yang, X. et al. "Dietary α-Linolenic and Linoleic Acids Competitively Affect Metabolism of Polyunsaturated Fatty Acids in Arctic Charr (*Salvelinus alpinus*)" The J. of Nutrition, 1994, 124(7):1133-1145.

Saito, H. et al. "High levels of n-3 polyunsaturated fatty acids in Euphausia pacifica and its role as a source of docosahexaenoic and icosapentaenoic acids for higher trophic levels" Marine Chem., 2002, 78:9-28.

Bell, J.G. et al. "Effects of diets rich in linoleic (18:2n-6) and α-linolenic (18:3n-3) acids on the growth, lipid class and fatty acid compositions and eicosanoid production in juvenile turbot (*Scophthalmus maximus* L.)" Fish Physio. And Biochem., 1994, 13(2):105-118.

Luzzana, U. et al. "Seasonal variations in fat content and fatty acid composition of male and female coregonid 'bondella' from Lake Maggiore and landlocked shad from Lake Como (Northern Italy)" J. Fish Biology, 1996, 48:352-366.

Aras, N.M. et al. "Comparison of Fatty Acid Profiles of Different Tissues of Mature Trout (*Salmo trutta labrax*, Pallas, 1811) Caught from Kazandere Creek in Çoruh Region, Erzurum, Turkey" Turkish J. Vet. Animal Sci., 2003, 27:311-316.

González-Félix, M.L. et al. "Nutritional evaluation of fatty acids for the open thelycum shrimp, *Litopenaeus vannamei*: II. Effect of dietary n-3 and n-6 polyunsaturated and highly unsaturated fatty acids on juvenile shrimp growth, survival, and fatty acid composition" Aquaculture Nutr., 2003, 9:115-122.

Abbadi, A. et al. "Biosynthesis of Very-Long-Chain Polyunsaturated Fatty Acids in Transgenic Oilseeds: Constraints on Their Accumulation" The Plant Cell, 2004, 16:2734-2748.

Hong, H. et al. "High-Level Production of γ-Linolenic Acid in *Brassica juncea* Using a Δ6 Desaturase from Pythium irregulare" Plant Physiology, 2002, 129:354-362.

Ursin, V.M. et al. "Modification of Plant Lipids for Human Health: Development of Functional Land-Based Omega-3 Fatty Acids" The J. of Nutrition, 133:4271-4274.

Sato, S. et al. "Production of γ-Linolenic Acid and Stearidonic Acid in Seeds of Marker-Free Trangenic Soybean" Crop Science, 44:646-652.

Sayanova, Olga et al. "Accumulation of Δ6-unsaturated fatty acids in transgenic tobacco plants expressing a Δ6-desaturase from Borago officinalis" J. Experimental Botany, 50(340):1647-1652.

Bell et al., Effect of dietary echium oil on growth, fatty acid composition and metabolism, gill prostaglandin production and macrophage activity in Atlantic cod (*Gadus morhua* L.). Aquaculture Research, 2006, 37:606-617.

Ghioni et al., Metabolism of 18:4n-3 (stearidonic acid) and 20:4n-3 in salmonoid cells in culture and inhibition of the production of prostaglandin F2 (PGF2) from 20:4n-6 (arachidonic acid). Fish Physiology and Biochemistry, 2002, 27:81-96.

Abbadi et al. (2001) "Transgenic oilseeds as sustainable source of nutritionally relevant C20 and C22 polyunsaturated fatty acids?" Eur. J. Lipid. Sci. Technol. 103:106-113.

Arondel et al. (1992) "Map-Based Cloning of a Gene Controlling Omega-3 Fatty Acid Desaturation in Arabidopsis" Science 258:1353-1355.

Barlow (2000) "Fishmeal and Fish Oil: Sustainable Feed Ingredients for Aquafeeds" Global Aquac. Advo. 3: 85-86.

Baumlein et al. (1991) "A novel seed protein gene from Vicia faba is developmentally regulated in transgenic tobacco and *Arabidopsis* plants" Mol. Gen. Genet. 225:459-467.

Baumlein et al (1992) "Cis-analysis of a seed protein gene promoter: the conservative RY repeat CATGCATG within the legumin box is essential for tissue-specific expression of a legumin gene" Plant J. 2:233-239.

Bell et al. (1993) "Effect of Diets Rich in Linoleic or α-Linolenic Acid on Phospholipid Fatty Acid Composition and Eicosanoid Production in Atlantic Salmon (*Salmo salar*)" Lipids. 28: 819-826.

Bell et al. (2001) "Replacement of Fish Oil with Rapeseed Oil in Diets of Atlantic Salmon (*Salmo salar*) Affects Tissue Lipid Compositions and Hepatocyte Fatty Acid Metabolism " J. Nutr. 131:1535-1543.

Bell et al. (2002) "Substituting Fish Oil with Crude Palm Oil in the Diet of Atlantic Salmon (*Salmo salar*) Affects Muscle Fatty Acid Composition and Hepatic Fatty Acid Metabolism" J. Nutr. 132: 222-230.

Bell et al. (2003) "Altered Fatty Acid Compositions in Atlantic Salmon (*Salmo salar*) Fed Diets Containing Linseed and Rapeseed Oils Can Be Partially Restored by a Subsequent Fish Oil Finishing Diet" J. Nutr. 133: 2793-2801.

Bell et al. (2004) "Replacement of Dietary Fish Oil with Increasing Levels of Linseed Oil: Modification of Flesh Fatty Acid Compositions in Atlantic Salmon (*Salmo salar*) Using a Fish Oil Finishing Diet" Lipids. 39: 223-232.

Berberich et al. (1998) "Two maize genes encoding ω-3 fatty acid desaturase and their differential expression to temperature" Plant Mol. Biol. 36:297-306.

(56) References Cited

OTHER PUBLICATIONS

Bilyeu et al. (2003) "Three Microsomal Omega-3 Fatty-Acid Desaturase Genes Contribute to Soybean Linolenic Acid Levels" Crop Sci. 43: 1833-1838.
Bligh and Dyer (1959) "Orange-red Flesh in Cod and Haddock" Can. J. Biochem. Physiol. 37: 911-917.
Bransden et al. (2003) "Replacement of fish oil with sunflower oil in feeds for Atlantic salmon (*Salmo salar* L.): effect on growth performance, tissue fatty acid composition and disease resistance" Comp. Biochem. Physiol, B. 135: 611-625.
Broun et al. (1998) "A bifunctional oleate 12-hydroxylase: desaturase from Lesquerella fendleri" Plant J. 13:201-210.
Browse and Slack (1981) "Catalase Stimulates Linoleate Desaturase Activity in Microsomes from Developing Linseed Cotyledons" FEBS Letters 131:111-114.
Carter et al. (2003) "Potential of Thraustochytrids to Partially Replace Fish Oil in Atlantic Salmon Feeds" Mar. Biotechnol. 5: 480-492.
Cho et al. (1999) "Cloning, Expression, and Nutritional Regulation of the Mammalian Δ-6 Desaturase" J. Biol. Chem. 274:471-477.
Chung et al. (1999) "Cloning and Characterization of a Seed-Specific ω-3 Fatty Acid Desaturase cDNA from Perilla frutescens" Plant Cell Physiol. 40: 114-118.
De Block et al. (1989) "Transformation of *Brassica napus* and *Brassica oleracea* Using Agrobacterium tumefaciens and the Expression of the bar and neo Genes in the Transgenic Plants" Plant Physiol. 91:694-701.
Domergue et al. (2002) "Cloning and functional characterization of Phaeodactylum tricornutum front-end desaturases involved in eicosapentaenoic acid biosynthesis" Eur. J. Biochem. 269:4105-4113.
Drexler et al. (2003) "Metabolic engineering of fatty acids for breeding of new oilseed crops: strategies, problems and first results" J. Plant Physiol. 160:779-802.
Fonseca-Madrigal et al. (2005) "Influence of dietary palm oil on growth, tissue fatty acid compositions, and fatty acid metabolism in liver and intestine in rainbow trout (*Oncorhynchus mykiss*)" Aquac. Nutr. 11: 241-250.
Fontagné et al (2000) "Response of common carp (*Cyprinus carpio*) larvae to different dietary levels and forms of supply of medium-chain fatty acids" Aquat. Living Resour. 13:429.437.
Gamborg et al. (1968) "Nutrient Requirements of Suspension Cultures of Soybean Root Cells" Exp. Cell Res. 50:151-158.
Garcia-Maroto et al. (2002) "Cloning and Molecular Characterization of the Δ6-Desaturase from Two Echium Plant Species: Production of GLA by Heterologous Expression in Yeast and Tobacco" Lipids 37:417-426.
Girke et al. (1998) "Identification of a novel Δ6-acyl-group desaturase by targeted gene disruption in Physcomitrella patens" Plant J. 15:39-48.
Good, Joanne Elizabeth: "Replacement of dietary fish oil with vegetable oils: effects on fish health", 2004, University of Stirling, XP002676377, pp. 264-304.
Guil-Guerrero et al. (2000) "Occurrence and characterization of oils rich in γ-linolenic acid Part I: Echium seeds from Macaronesia" Phytochemistry 53:451-456.
Hamada et al. (1994) "Cloning of a cDNA encoding tobacco ω-3 fatty acid desaturase" Gene 147: 293-294.
Hamada et al. (1996) "cDNA Cloning of a Wounding-Inducible Gene Encoding a Plastid ω-3 Fatty Acid Desaturase from Tobacco" Plant Cell Physiol. 37: 606-611.
Harel et al. (2002) "Advanced DHA, EPA and ArA enrichment materials for marine aquaculture using single cell heterotrophs" Aquaculture. 213: 347-362.
Hastings et al. (2001) "A vertebrate fatty acid desaturase with Δ5 and Δ6 activities" Proc. Natl. Acad. Sci. U.S.A. 98:14304-14309.
Helland et al. (1996) "A simple method for the measurement of daily feed intake of groups of fish in tanks" Aquaculture. 139: 157-163.
Hong et al. (2002) "Isolation and Characterization of a Δ5 FA Desaturase from Pythium irregulare by Heterologous Expression in *Saccharomyces cerevisiae* and Oilseed Crops" Lipids 37:863-868.
Horiguchi et al. (1998) "Developmental Regulation of Genes for Microsome and Plastid ω-3 Fatty Acid Desaturases in Wheat (*Triticum aestivum* L.)" Plant Cell Physiol. 39:540-544.
Huang et al. (1999) "Cloning of Δ12- and Δ6-Desaturases from Mortierella alpine and Recombinant Production of γ-Linolenic Acid in *Saccharomyces cerevisiae*" Lipids 34:649-659.
Jones and Harwood (1980) "Desaturation of linoleic acid from exogenous lipids by isolated chloroplasts" Biochem J. 190:851-854.
Kajikawa et al. (2004) "Isolation and characterization of Δ6-desaturase, an ELO-like enzyme and Δ5-desaturase from the liverwort *Marchantia polymorpha* and production of arachidonic and eicosapentaenoic acids in the methylotrophic yeast *Pichia pastoris*" Plant Mol Biol 54:335-352.
Kirsch et al. (1997) "Rapid, transient, and highly localized induction of plastidial ω-3 fatty acid desaturase mRNA at fungal infection sites in Petroselinum crispum" Proc. Natl. Acad. Sci. U.S.A. 94: 2079-2084.
Kishnankutty (2005) "Plant proteins in fish feed: An additional analysis" Biochimica et Biophysica Acta 1734:13-24.
Leonard, et al. (2000) "cDNA cloning and characterization of human Δ5-desaturase involved in the biosynthesis of arachidonic acid" Biochem. J. 347:719-724.
Li et al. (2003) "The Tomato Suppressor of prosystemin-mediated responses2 Gene Encodes a Fatty Acid Desaturase Required for the Biosynthesis of Jasmonic Acid and the Production of a Systemic Wound Signal for Defense Gene Expression" Plant Cell 15:1646-1661.
Liu et al. (2002) "High-Stearic and High-Oleic Cottonseed Oils Produced by Hairpin RNA-Mediated Post-Transcriptional Gene Silencing" Plant Physiol. 129:1732-1743.
Metz et al. (2001) "Production of Polyunsaturated Fatty Acids by Polyketide Synthases in Both Prokaryotes and Eukaryotes" Science 293:290-293.
Meyer et al. (2003) "Biosynthesis of Docosahexaenoic Acid in Euglena gracilis: Biochemical and Molecular Evidence for the Involvement of a Δ4-Fatty Acyl Group Desaturase" Biochemistry 42:9779-9788.
Michaelson et al. (1998) "Isolation of a Δ5-Fatty Acid Desaturase Gene from Mortierella alpina" J. Biol. Chem. 273:19055-19059.
Morita et al. (2000) "Biosynthesis of fatty acids in the docosahexaenoic acid-producing bacterium Moritella marina strain MP-1" Biochem. Soc. Trans. 28:872-879.
Murashige and Skoog (1962) "A Revised Medium for Rapid Growth and Bio Assays with Tobacco Tissue Cultures" Physiologica Plantarum 28:147-150.
Napier et al. (1998) "Identification of a Caenorhabditis elegans Δ6-fatty-acid-desaturase by heterologous expression in *Saccharomyces cerevisiae*" Biochem J. 330:611-614.
Napier et al. (1999) "A growing family of cytochrome b5-domain fusion proteins" Trends in Plant Sci 4:2-4.
Naylor et al. (2000) "Effect of aquaculture on world fish supplies" Nature. 405: 1017-1024.
Needleman and Wunsch (1970) "A General Method Applicable to the Search for Similarities in the Amino Acid Sequence of Two Proteins" J. Mol. Biol. 48:443-453.
Pereira et al. (2004) "A novel ω3-fatty acid desaturase involved in the biosynthesis of eicosapentaenoic acid" Biochem. J. 378:665-671.
Polvi and Ackman (1992) "Atlantic salmon (*Salmo salar*) muscle lipids and their response to alternative dietary fatty acid sources" J Agric. Food Chem. 40:1001-1007.
Qi et al. (2002) "Identification of a cDNA encoding a novel C18-Δ9 polyunsaturated fatty acid-specific elongating activity from the docosahexaenoic acid (DHA)-producing microalga, *Isochrysis galbana*" FEBS Lett. 510:159-165.
Qiu et al. (2001) "Identification of a Δ4 Fatty Acid Desaturase from Thraustochytrium sp. Involved in the Biosynthesis of Docosahexanoic Acid by Heterologous Expression in *Saccharomyces cerevisiae* and *Brassica juncea*" J. Biol. Chem. 276:31561-31566.

(56) References Cited

OTHER PUBLICATIONS

Radke et al. (1988) "Transformation of *Brassica napus* L. using Agrobacterium tumefaciens: developmentally regulated expression of a reintroduced napin gene" Theor. Appl. Genet. 75: 685-694.
Reddy et al. (1993) "Isolation of Δ6-desaturase gene from the cyanobacterium *Synechocystis* sp. strain PCC 6803 by gain-of-function expression in *Anabaena* sp. strain PCC 7120" Plant Mol. Biol. 22:293-300.
Sakamoto et al. (1997) "Temperature-regulated mRNA accumulation and stabilization for fatty acid desaturase genes in the cyanobacterium *Synechococcus* sp. strain Pcc 7002" Mol. Microbiol. 23: 1281-1292.
Sakuradani et al. (1999) "Δ6-Fatty acid desaturase from an arachidonic acid-producing Mortierella fungus Gene cloning and its heterologous expression in a fungus, Aspergillus" Gene 238:445-453.
Sayanova et al. (1997) "Expression of a borage desaturase cDNA containing an N-terminal cytochrome b5 domain results in the accumulation of high levels of Δ6- desaturated fatty acids in transgenic tobacco" Proc. Natl. Acad. Sci. U.S.A. 94:4211-4216.
Sayanova et al. (1999) "Histidine-41 of the Cytochrome b5 Domain of the Borage Δ6 Fatty Acid Desaturase Is Essential for Enzyme Activity1" Plant Physiol. 121:641-646.
Sayanova et al. (2003) "Identification of Primula fatty acid Δ6-desaturases with n-3 substrate preferences" FEBS Lett. 542:100-104.
Sayanova and Napier (2004) "Eicosapentaenoic acid: biosynthetic routes and the potential for synthesis in transgenic plants" Phytochemistry 65:147-158.
Seierstad et al. (2005) "Dietary intake of differently fed salmon the influence on markers of human atherosclerosis" Euro. J. Clin. Invest. 35: 52-59.
Sterling (2001) Sustainability of fish meal and oil supply. Paper presented at Scottish-Norwegian Conference on Sustainable Futures for Marine Fish Farming (Jun. 2001). www.iffo.org.uldtechisterling.htm.
Sperling et al. (2000) "A bifunctional Δ6-fatty acyl acetylenase/desaturase from the moss *Ceratodon purpureus*" Eur. J. Biochem. 267:3801-3811.
Sperling and Heinz (2001) "Desaturases fused to their electron donor" Eur. J. Lipid Sci. Technol 103:158-180.
Sprecher et al. (1995) "Reevaluation of the pathways for the biosynthesis of polyunsaturated fatty acids" J. Lipid Res. 36:2471-2477.
Spychalla et al. (1997) "Identification of an animal ω-3 fatty acid desaturase by heterologous expression in Arabidopsis" Proc. Natl. Acad. Sci. U.S.A. 94:1142-1147.
Suga et al. (2002) "Two Low-temperature-inducible Chlorella Genes for Δ12 and ω-3 Fatty Acid Desaturase (FAD): Isolation of Δ12 and ω-3 fad cDNA Clones, Expression of Δ12 fad in *Saccharomyces cerevisiae*, and Expression of ω-3 fad in *Nicotiana tabacum*" Biosci. Biotechnol. Biochem. 66: 1314-1327.
Takeyama et al. (1997) "Expression of the eicosapentaenoic acid synthesis gene cluster from *Shewanella* sp. in a transgenic marine cyanobacterium, *Synechococcus* sp." Microbiology 143:2725-2731.
Tanaka et al. (1999) "Isolation of clustered genes that are notably homologous to the eicosapentaenoic acid biosynthesis gene cluster from the docosahexaenoic acid-producing bacterium Vibrio marinus strain MP-1" Biotechnol. Lett. 21:939-945.
Tang et al. (1999) GenBank Accession No. AAD13527.1 "omega-3 fatty acid desaturase precursor [*Vernicia fordii*]".
Tanhuanpaa et al. (2002) "Mapping of genes affecting linolenic acid content in *Brassica rapa* ssp. oleifera" Mol. Breed. 10: 51-62.
Torstensen et al. (2004) "Replacing dietary fish oil with increasing levels of rapeseed oil and olive oil—effects on Atlantic salmon (*Salmo salar* L.) tissue and lipoprotein lipid composition and lipogenic enzyme activities" Aquac. Nutr. 10: 175-192.
van de Loo and Somerville (1994) "Plasmid ω-3 Fatty Acid Desaturase cDNA from Ricinus communis" Plant Physiol. 105: 443-444.

Vrinten et al. (2005) "Two FAD3 Desaturase Genes Control the Level of Linolenic Acid in Flax Seed" Plant Physiol. 139: 79-87.
Wallis and Browse (1999) "The Δ8-Desaturase of Euglena gracilis: An Alternate Pathway for Synthesis of 20-Carbon Polyunsaturated Fatty Acids" Arch. Biochem. Biophys. 365:307-316.
Wang et al. (1998) "Improved Vectors for Agrobacterium tumefaciens-mediated Transformation of Monocot Plants" Acta Horticulturae 461: 401-407.
Whitney et al. (2003) "Functional characterisation of two cytochrome b5-fusion desaturases from Anemone leveillei: the unexpected identification of a fatty acid Δ6-desaturase" Planta 217:983-992.
Yadav et al. (1993) "Cloning of Higher Plant ω-3 Fatty Acid Desaturases" Plant Physiol. 103: 467-476.
Yamamoto et al. (1992) "Novel mRNA Sequences Induced by Indole-3-Acetic Acid in Sections of Elongating Hypocotyls of Mung Bean (*Vigna radiata*)" Plant Cell Physiol. 33: 13-20.
Yamazaki et al. (1992) "Comparison of the conversion rates of α-linilenic acid (18:3(n-3)) and steridonic acid (18:4(n-3)) to longer polyunsaturated fatty acids in rats" Biochim. Biophys. Acta. 1123: 18-26.
Yang et al. (2004) "SOR1, a gene associated with bioherbicide production in sorghum root hairs" J. Exp. Bot. 55: 2251-2259.
Yazawa (1996) "Production of Eicosapentaenoic Acid from Marine Bacteria" Lipids 31:S297-S300.
Yu et al. (2000) "Production of Eicosapentaenoic Acid by a Recombinant Marine Cyanobacterium, *Synechococcus* sp." Lipids 35:1061-1064.
Zhang et al. (2004) "Large-scale analysis of the barley transcriptome based on expressed sequence tags" FEBS Lett. 556:81-85.
Zheng et al. (2005) "Environmental and dietary influences on highly unsaturated fatty acid biosynthesis and expression of fatty acyl desaturase and elongase genes in liver of Atlantic salmon (*Salmo salar*)" Biochimica et Biophysica Acta 1734: 13-24.
Extended European Search Report and Search Opinion dated Jun. 6, 2012 in connection with European Patent Application No. 06817510.8.
Australian Examination Report dated May 30, 2011 in connection with Australian Patent Application No. 2006315096.
Response filed to Australian Examination Report filed Feb. 14, 2013 in connection with Australian Patent Application No. 2006315096.
Office Action dated Sep. 13, 2011 in connection with U.S. Appl. No. 12/085,261, filed Jun. 23, 2009.
Response to Office Action dated Sep. 13, 2011, filed Nov. 14, 2011, in connection with U.S. Appl. No. 12/085,261, filed Jun. 23, 2009.
Office Action dated Dec. 22, 2011 in connection with U.S. Appl. No. 12/085,261, filed Jun. 23, 2009.
Response to Office Action dated Dec. 22, 2011, filed Mar. 22, 2012, in connection with U.S. Appl. No. 12/085,261, filed Jun. 23, 2009.
Office Action dated Dec. 6, 2012 in connection with U.S. Appl. No. 12/085,261, filed Jun. 23, 2009.
Response to Office Action dated Dec. 6, 2012, filed Apr. 8, 2013, in connection with U.S. Appl. No. 12/085,261, filed Jun. 23, 2009.
Office Action dated Oct. 3, 2013 in connection with U.S. Appl. No. 12/085,261, filed Jun. 23, 2009.
Response to Office Action dated Oct. 3, 2013, filed Feb. 11, 2014, in connection with U.S. Appl. No. 12/085,261, filed Jun. 23, 2009.
Notice of Allowance dated Feb. 28, 2014 in connection with U.S. Appl. No. 12/085,261, filed Jun. 23, 2009.
Amendment filed Mar. 20, 2014 in connection with U.S. Appl. No. 12/085,261, filed Jun. 23, 2009.
Communication filed May 27, 2014 in connection with U.S. Appl. No. 12/085,261, filed Jun. 23, 2009.
Examination Report dated Sep. 26, 2016 and cited documents for European patent application 06817510.8.
Third Party Observations dated Oct. 1, 2016 in connection with European patent application 06817510.8.
Summons to Oral Proceedings dated Nov. 13, 2017 which issued in relation to European patent application 06817510.8.
Examiner's first report and its English translation which issued in relation to corresponding Norwegian patent application 20082797.
Good, Joanne Elizabeth, "Culture of Atlantic cod (*Gadus morhua*) juveniles and Arctic char (*Salvelinus alpinus*) on diets containing Echium oil: effects on fish health and immune function", Replace-

(56) References Cited

OTHER PUBLICATIONS ment of dietary fish oil with vegetable oils: effects on fish health, University of Stirling, (2004), pp. 264-304.

Cathryn E Wood, "Premarket Notification for a new Dietary ingredient, Echium oil", Jan. 1, 2002.

Virginia M Ursin, "Symposium: Improving human nutrition through genomics, proteomics and biotechnologies, modification of plant lipids for human health: Development of functional land-based omega-3 fatty acids 1", The journal of Nutrition, vol. 133, Nov. 4, 2003, pp. 4271-4274.

Carole Blanchet et al; "Fatty acid composition of wild and farmed Atlantic salmon (*salmo solar*) and rainbow trout (*Oncorhynchus mykiss*)", Lipids, vol. 40, No. 5, Jan. 5, 2005, pp. 529-531.

* cited by examiner

SEQUENCE LISTING

<160> NUMBER OF SEQ ID NOS: 31

<210> SEQ ID NO 1
<211> LENGTH: 444
<212> TYPE: PRT
<213> ORGANISM: Homo sapiens

<400> SEQUENCE: 1

```
Met Gly Lys Gly Gly Asn Gln Gly Glu Gly Ala Ala Glu Arg Glu Val
1               5                   10                  15

Ser Val Pro Thr Phe Ser Trp Glu Glu Ile Gln Lys His Asn Leu Arg
            20                  25                  30

Thr Asp Arg Trp Leu Val Ile Asp Arg Lys Val Tyr Asn Ile Thr Lys
        35                  40                  45

Trp Ser Ile Gln His Pro Gly Gly Gln Arg Val Ile Gly His Tyr Ala
    50                  55                  60

Gly Glu Asp Ala Thr Asp Ala Phe Arg Ala Phe His Pro Asp Leu Glu
65                  70                  75                  80

Phe Val Gly Lys Phe Leu Lys Pro Leu Leu Ile Gly Glu Leu Ala Pro
                85                  90                  95

Glu Glu Pro Ser Gln Asp His Gly Lys Asn Ser Lys Ile Thr Glu Asp
            100                 105                 110

Phe Arg Ala Leu Arg Lys Thr Ala Glu Asp Met Asn Leu Phe Lys Thr
        115                 120                 125

Asn His Val Phe Phe Leu Leu Leu Leu Ala His Ile Ile Ala Leu Glu
    130                 135                 140

Ser Ile Ala Trp Phe Thr Val Phe Tyr Phe Gly Asn Gly Trp Ile Pro
145                 150                 155                 160

Thr Leu Ile Thr Ala Phe Val Leu Ala Thr Ser Gln Ala Gln Ala Gly
                165                 170                 175

Trp Leu Gln His Asp Tyr Gly His Leu Ser Val Tyr Arg Lys Pro Lys
            180                 185                 190

Trp Asn His Leu Val His Lys Phe Val Ile Gly His Leu Lys Gly Ala
        195                 200                 205

Ser Ala Asn Trp Trp Asn His Arg His Phe Gln His Ala Lys Pro
    210                 215                 220

Asn Ile Phe His Lys Asp Pro Asp Val Asn Met Leu His Val Phe Val
225                 230                 235                 240

Leu Gly Glu Trp Gln Pro Ile Glu Tyr Gly Lys Lys Lys Leu Lys Tyr
                245                 250                 255

Leu Pro Tyr Asn His Gln His Glu Tyr Phe Phe Leu Ile Gly Pro Pro
            260                 265                 270

Leu Leu Ile Pro Met Tyr Phe Gln Tyr Gln Ile Ile Met Thr Met Ile
        275                 280                 285

Val His Lys Asn Trp Val Asp Leu Ala Trp Ala Val Ser Tyr Tyr Ile
    290                 295                 300

Arg Phe Phe Ile Thr Tyr Ile Pro Phe Tyr Gly Ile Leu Gly Ala Leu
305                 310                 315                 320

Leu Phe Leu Asn Phe Ile Arg Phe Leu Glu Ser His Trp Phe Val Trp
                325                 330                 335

Val Thr Gln Met Asn His Ile Val Met Glu Ile Asp Gln Glu Ala Tyr
            340                 345                 350

Arg Asp Trp Phe Ser Ser Gln Leu Thr Ala Thr Cys Asn Val Glu Gln
        355                 360                 365
```

```
Ser Phe Phe Asn Asp Trp Phe Ser Gly His Leu Asn Phe Gln Ile Glu
    370                 375                 380

His His Leu Phe Pro Thr Met Pro Arg His Asn Leu His Lys Ile Ala
385                 390                 395                 400

Pro Leu Val Lys Ser Leu Cys Ala Lys His Gly Ile Glu Tyr Gln Glu
                405                 410                 415

Lys Pro Leu Leu Arg Ala Leu Leu Asp Ile Ile Arg Ser Leu Lys Lys
                420                 425                 430

Ser Gly Lys Leu Trp Leu Asp Ala Tyr Leu His Lys
                435                 440

<210> SEQ ID NO 2
<211> LENGTH: 444
<212> TYPE: PRT
<213> ORGANISM: Mus musculus

<400> SEQUENCE: 2

Met Gly Lys Gly Gly Asn Gln Gly Glu Gly Ser Thr Glu Arg Gln Ala
1               5                   10                  15

Pro Met Pro Thr Phe Arg Trp Glu Glu Ile Gln Lys His Asn Leu Arg
                20                  25                  30

Thr Asp Arg Trp Leu Val Ile Asp Arg Lys Val Tyr Asn Val Thr Lys
            35                  40                  45

Trp Ser Gln Arg His Pro Gly Gly His Arg Val Ile Gly His Tyr Ser
        50                  55                  60

Gly Glu Asp Ala Thr Asp Ala Phe Arg Ala Phe His Leu Asp Leu Asp
65                  70                  75                  80

Phe Val Gly Lys Phe Leu Lys Pro Leu Leu Ile Gly Glu Leu Ala Pro
                85                  90                  95

Glu Glu Pro Ser Leu Asp Arg Gly Lys Ser Ser Gln Ile Thr Glu Asp
                100                 105                 110

Phe Arg Ala Leu Lys Lys Thr Ala Glu Asp Met Asn Leu Phe Lys Thr
            115                 120                 125

Asn His Leu Phe Phe Phe Leu Leu Leu Ser His Ile Ile Val Met Glu
        130                 135                 140

Ser Leu Ala Trp Phe Ile Leu Ser Tyr Phe Gly Thr Gly Trp Ile Pro
145                 150                 155                 160

Thr Leu Val Thr Ala Phe Val Leu Ala Thr Ser Gln Ala Gln Ala Gly
                165                 170                 175

Trp Leu Gln His Asp Tyr Gly His Leu Ser Val Tyr Lys Lys Ser Ile
                180                 185                 190

Trp Asn His Val Val His Lys Phe Val Ile Gly His Leu Lys Gly Ala
            195                 200                 205

Ser Ala Asn Trp Trp Asn His Arg His Phe Gln His His Ala Lys Pro
        210                 215                 220

Asn Ile Phe His Lys Asp Pro Asp Ile Lys Ser Leu His Val Phe Val
225                 230                 235                 240

Leu Gly Glu Trp Gln Pro Leu Glu Tyr Gly Lys Lys Leu Lys Tyr
                245                 250                 255

Leu Pro Tyr Asn His Gln His Gly Tyr Phe Phe Leu Ile Gly Pro Pro
                260                 265                 270

Leu Leu Ile Pro Met Tyr Phe Gln Tyr Gln Ile Ile Met Thr Met Ile
            275                 280                 285

Ser Arg Arg Asp Trp Val Asp Leu Ala Trp Ala Ile Ser Tyr Tyr Met
290                 295                 300
```

Arg Phe Phe Tyr Thr Tyr Ile Pro Phe Tyr Gly Ile Leu Gly Ala Leu
305                 310                 315                 320

Val Phe Leu Asn Phe Ile Arg Phe Leu Glu Ser His Trp Phe Val Trp
                325                 330                 335

Val Thr Gln Met Asn His Leu Val Met Glu Ile Asp Leu Asp His Tyr
            340                 345                 350

Arg Asp Trp Phe Ser Ser Gln Leu Ala Ala Thr Cys Asn Val Glu Gln
                355                 360                 365

Ser Phe Phe Asn Asp Trp Phe Ser Gly His Leu Asn Phe Gln Ile Glu
370                 375                 380

His His Leu Phe Pro Thr Met Pro Arg His Asn Leu His Lys Ile Ala
385                 390                 395                 400

Pro Leu Val Lys Ser Leu Cys Ala Lys His Gly Ile Glu Tyr Gln Glu
                405                 410                 415

Lys Pro Leu Leu Arg Ala Leu Ile Asp Ile Val Ser Ser Leu Lys Lys
                420                 425                 430

Ser Gly Glu Leu Trp Leu Asp Ala Tyr Leu His Lys
                435                 440

<210> SEQ ID NO 3
<211> LENGTH: 459
<212> TYPE: PRT
<213> ORGANISM: Pythium irregulare

<400> SEQUENCE: 3

Met Val Asp Leu Lys Pro Gly Val Lys Arg Leu Val Ser Trp Lys Glu
1               5                   10                  15

Ile Arg Glu His Ala Thr Pro Ala Thr Ala Trp Ile Val Ile His His
                20                  25                  30

Lys Val Tyr Asp Ile Ser Lys Trp Asp Ser His Pro Gly Gly Ser Val
            35                  40                  45

Met Leu Thr Gln Ala Gly Glu Asp Ala Thr Asp Ala Phe Ala Val Phe
        50                  55                  60

His Pro Ser Ser Ala Leu Lys Leu Leu Glu Gln Phe Tyr Val Gly Asp
65                  70                  75                  80

Val Asp Glu Thr Ser Lys Ala Glu Ile Glu Gly Pro Ala Ser Asp
                85                  90                  95

Glu Glu Arg Ala Arg Arg Glu Arg Ile Asn Glu Phe Ile Ala Ser Tyr
                100                 105                 110

Arg Arg Leu Arg Val Lys Val Lys Gly Met Gly Leu Tyr Asp Ala Ser
            115                 120                 125

Ala Leu Tyr Tyr Ala Trp Lys Leu Val Ser Thr Phe Gly Ile Ala Val
        130                 135                 140

Leu Ser Met Ala Ile Cys Phe Phe Asn Ser Phe Ala Met Tyr Met
145                 150                 155                 160

Val Ala Gly Val Ile Met Gly Leu Phe Tyr Gln Gln Ser Gly Trp Leu
                165                 170                 175

Ala His Asp Phe Leu His Asn Gln Val Cys Glu Asn Arg Thr Leu Gly
            180                 185                 190

Asn Leu Ile Gly Cys Leu Val Gly Asn Ala Trp Gln Gly Phe Ser Val
        195                 200                 205

Gln Trp Trp Lys Asn Lys His Asn Leu His His Ala Val Pro Asn Leu
210                 215                 220

His Ser Ala Lys Asp Glu Gly Phe Ile Gly Asp Pro Asp Ile Asp Thr

```
225                 230                 235                 240

Met Pro Leu Leu Ala Trp Ser Lys Glu Met Ala Arg Lys Ala Phe Glu
                245                 250                 255

Ser Ala His Gly Pro Phe Phe Ile Arg Asn Gln Ala Phe Leu Tyr Phe
            260                 265                 270

Pro Leu Leu Leu Ala Arg Leu Ser Trp Leu Ala Gln Ser Phe Phe
        275                 280                 285

Tyr Val Phe Thr Glu Phe Ser Phe Gly Ile Phe Asp Lys Val Glu Phe
        290                 295                 300

Asp Gly Pro Glu Lys Ala Gly Leu Ile Val His Tyr Ile Trp Gln Leu
305                 310                 315                 320

Ala Ile Pro Tyr Phe Cys Asn Met Ser Leu Phe Glu Gly Val Ala Tyr
                325                 330                 335

Phe Leu Met Gly Gln Ala Ser Cys Gly Leu Leu Leu Ala Leu Val Phe
            340                 345                 350

Ser Ile Gly His Asn Gly Met Ser Val Tyr Glu Arg Glu Thr Lys Pro
        355                 360                 365

Asp Phe Trp Gln Leu Gln Val Thr Thr Thr Arg Asn Ile Arg Ala Ser
    370                 375                 380

Val Phe Met Asp Trp Phe Thr Gly Gly Leu Asn Tyr Gln Ile Asp His
385                 390                 395                 400

His Leu Phe Pro Leu Val Pro Arg His Asn Leu Pro Lys Val Asn Val
                405                 410                 415

Leu Ile Lys Ser Leu Cys Lys Glu Phe Asp Ile Pro Phe His Glu Thr
            420                 425                 430

Gly Phe Trp Glu Gly Ile Tyr Glu Val Val Asp His Leu Ala Asp Ile
        435                 440                 445

Ser Lys Glu Phe Ile Thr Glu Phe Pro Ala Met
        450                 455

<210> SEQ ID NO 4
<211> LENGTH: 448
<212> TYPE: PRT
<213> ORGANISM: Borago officinalis

<400> SEQUENCE: 4

Met Ala Ala Gln Ile Lys Lys Tyr Ile Thr Ser Asp Glu Leu Lys Asn
1               5                   10                  15

His Asp Lys Pro Gly Asp Leu Trp Ile Ser Ile Gln Gly Lys Ala Tyr
            20                  25                  30

Asp Val Ser Asp Trp Val Lys Asp His Pro Gly Gly Ser Phe Pro Leu
        35                  40                  45

Lys Ser Leu Ala Gly Gln Glu Val Thr Asp Ala Phe Val Ala Phe His
    50                  55                  60

Pro Ala Ser Thr Trp Lys Asn Leu Asp Lys Phe Phe Thr Gly Tyr Tyr
65                  70                  75                  80

Leu Lys Asp Tyr Ser Val Ser Glu Val Ser Lys Asp Tyr Arg Lys Leu
                85                  90                  95

Val Phe Glu Phe Ser Lys Met Gly Leu Tyr Asp Lys Lys Gly His Ile
            100                 105                 110

Met Phe Ala Thr Leu Cys Phe Ile Ala Met Leu Phe Ala Met Ser Val
        115                 120                 125

Tyr Gly Val Leu Phe Cys Glu Gly Val Leu Val His Leu Phe Ser Gly
    130                 135                 140
```

Cys Leu Met Gly Phe Leu Trp Ile Gln Ser Gly Trp Ile Gly His Asp
145                 150                 155                 160

Ala Gly His Tyr Met Val Val Ser Asp Ser Arg Leu Asn Lys Phe Met
            165                 170                 175

Gly Ile Phe Ala Ala Asn Cys Leu Ser Gly Ile Ser Ile Gly Trp Trp
        180                 185                 190

Lys Trp Asn His Asn Ala His His Ile Ala Cys Asn Ser Leu Glu Tyr
    195                 200                 205

Asp Pro Asp Leu Gln Tyr Ile Pro Phe Leu Val Val Ser Ser Lys Phe
    210                 215                 220

Phe Gly Ser Leu Thr Ser His Phe Tyr Glu Lys Arg Leu Thr Phe Asp
225                 230                 235                 240

Ser Leu Ser Arg Phe Phe Val Ser Tyr Gln His Trp Thr Phe Tyr Pro
                245                 250                 255

Ile Met Cys Ala Ala Arg Leu Asn Met Tyr Val Gln Ser Leu Ile Met
            260                 265                 270

Leu Leu Thr Lys Arg Asn Val Ser Tyr Arg Ala Gln Glu Leu Leu Gly
        275                 280                 285

Cys Leu Val Phe Ser Ile Trp Tyr Pro Leu Leu Val Ser Cys Leu Pro
290                 295                 300

Asn Trp Gly Glu Arg Ile Met Phe Val Ile Ala Ser Leu Ser Val Thr
305                 310                 315                 320

Gly Met Gln Gln Val Gln Phe Ser Leu Asn His Phe Ser Ser Ser Val
                325                 330                 335

Tyr Val Gly Lys Pro Lys Gly Asn Asn Trp Phe Glu Lys Gln Thr Asp
            340                 345                 350

Gly Thr Leu Asp Ile Ser Cys Pro Pro Trp Met Asp Trp Phe His Gly
        355                 360                 365

Gly Leu Gln Phe Gln Ile Glu His Leu Phe Pro Lys Met Pro Arg
    370                 375                 380

Cys Asn Leu Arg Lys Ile Ser Pro Tyr Val Ile Glu Leu Cys Lys Lys
385                 390                 395                 400

His Asn Leu Pro Tyr Asn Tyr Ala Ser Phe Ser Lys Ala Asn Glu Met
                405                 410                 415

Thr Leu Arg Thr Leu Arg Asn Thr Ala Leu Gln Ala Arg Asp Ile Thr
            420                 425                 430

Lys Pro Leu Pro Lys Asn Leu Val Trp Glu Ala Leu His Thr His Gly
        435                 440                 445

<210> SEQ ID NO 5
<211> LENGTH: 446
<212> TYPE: PRT
<213> ORGANISM: Anemone leveillei

<400> SEQUENCE: 5

Met Ala Glu Lys Arg Arg Ser Ile Ser Ser Asp Asp Leu Arg Ser His
1               5                   10                  15

Asn Lys Pro Gly Asp Val Trp Ile Ser Ile Gln Gly Lys Ile Tyr Asp
            20                  25                  30

Val Thr Glu Trp Gly Lys Asp His Pro Gly Glu Gly Pro Leu Leu
        35                  40                  45

Asn Leu Ala Gly Gln Asp Val Thr Asp Ala Phe Val Ala Phe His Pro
    50                  55                  60

Gly Ser Ala Trp Lys Asn Leu Asp Lys Phe His Ile Gly Tyr Leu Gln
65                  70                  75                  80

```
Asp Tyr Val Val Ser Asp Val Ser Lys Asp Tyr Arg Lys Leu Val Ser
                85                  90                  95

Glu Phe Ser Lys Ala Gly Leu Tyr Glu Lys Lys Gly His Gly His Leu
            100                 105                 110

Ile Arg Leu Leu Val Met Ser Leu Val Phe Ile Ala Ser Val Ser Gly
        115                 120                 125

Val Val Leu Ser Asp Lys Thr Ser Val His Val Gly Ser Ala Val Leu
    130                 135                 140

Leu Ala Val Ile Trp Met Gln Phe Gly Phe Ile Gly His Asp Ser Gly
145                 150                 155                 160

His Tyr Asn Ile Met Thr Ser Pro Glu Leu Asn Arg Tyr Met Gln Ile
                165                 170                 175

Phe Ser Val Asn Val Val Ser Gly Val Ser Val Gly Trp Trp Lys Arg
            180                 185                 190

Tyr His Asn Ala His His Ile Ala Val Asn Ser Leu Glu Tyr Asp Pro
        195                 200                 205

Asp Leu Gln Tyr Val Pro Phe Leu Val Val Ser Thr Ala Ile Phe Asp
    210                 215                 220

Ser Leu Thr Ser His Phe Tyr Arg Lys Lys Met Thr Phe Asp Ala Val
225                 230                 235                 240

Ala Arg Phe Leu Val Ser Phe Gln His Trp Thr Phe Tyr Pro Leu Met
                245                 250                 255

Ala Ile Gly Arg Val Ser Phe Leu Ala Gln Ser Ile Gly Val Leu Leu
            260                 265                 270

Ser Lys Lys Pro Leu Pro Asp Arg His Leu Glu Trp Phe Gly Leu Val
        275                 280                 285

Val Phe Trp Ala Trp Tyr Ser Leu Leu Ile Ser Cys Leu Pro Asn Trp
    290                 295                 300

Trp Glu Arg Val Ile Phe Ile Ala Val Asn Phe Ala Val Thr Gly Ile
305                 310                 315                 320

Gln His Val Gln Phe Cys Leu Asn His Tyr Ser Ala Gln Thr Tyr Ile
                325                 330                 335

Gly Ala Pro Cys Ala Asn Asp Trp Phe Glu Lys Gln Thr Lys Gly Ser
            340                 345                 350

Ile Asp Ile Ser Cys Ser Pro Trp Thr Asp Trp Phe His Gly Gly Leu
        355                 360                 365

Gln Phe Gln Ile Glu His His Leu Phe Pro Arg Met Pro Arg Cys Asn
    370                 375                 380

Leu Arg Lys Ile Ser Pro Phe Val Lys Glu Leu Cys Arg Lys His Asn
385                 390                 395                 400

Leu Val Tyr Thr Ser Val Ser Phe Phe Glu Gly Asn Arg Arg Thr Leu
                405                 410                 415

Ala Thr Leu Lys Asn Ala Ala Leu Lys Ala Arg Asp Leu Thr Ser Pro
            420                 425                 430

Ile Pro Lys Asn Leu Val Trp Glu Ala Val His Thr His Gly
        435                 440                 445

<210> SEQ ID NO 6
<211> LENGTH: 520
<212> TYPE: PRT
<213> ORGANISM: Ceratodon purpureus

<400> SEQUENCE: 6

Met Val Ser Gln Gly Gly Gly Leu Ser Gln Gly Ser Ile Glu Glu Asn
```

-continued

```
1               5                   10                  15
Ile Asp Val Glu His Leu Ala Thr Met Pro Leu Val Ser Asp Phe Leu
                20                  25                  30

Asn Val Leu Gly Thr Thr Leu Gly Gln Trp Ser Leu Ser Thr Thr Phe
                35                  40                  45

Ala Phe Lys Arg Leu Thr Thr Lys Lys His Ser Ser Asp Ile Ser Val
    50                  55                  60

Glu Ala Gln Lys Glu Ser Val Ala Arg Gly Pro Val Glu Asn Ile Ser
65                  70                  75                  80

Gln Ser Val Ala Gln Pro Ile Arg Arg Trp Val Gln Asp Lys Lys
                85                  90                  95

Pro Val Thr Tyr Ser Leu Lys Asp Val Ala Ser His Asp Met Pro Gln
                100                 105                 110

Asp Cys Trp Ile Ile Lys Glu Lys Val Tyr Asp Val Ser Thr Phe
                115                 120                 125

Ala Glu Gln His Pro Gly Gly Thr Val Ile Asn Thr Tyr Phe Gly Arg
                130                 135                 140

Asp Ala Thr Asp Val Phe Ser Thr Phe His Ala Ser Thr Ser Trp Lys
145                 150                 155                 160

Ile Leu Gln Asn Phe Tyr Ile Gly Asn Leu Val Arg Glu Glu Pro Thr
                165                 170                 175

Leu Glu Leu Leu Lys Glu Tyr Arg Glu Leu Arg Ala Leu Phe Leu Arg
                180                 185                 190

Glu Gln Leu Phe Lys Ser Ser Lys Ser Tyr Tyr Leu Phe Lys Thr Leu
                195                 200                 205

Ile Asn Val Ser Ile Val Ala Thr Ser Ile Ala Ile Ser Leu Tyr
    210                 215                 220

Lys Ser Tyr Arg Ala Val Leu Leu Ser Ala Ser Leu Met Gly Leu Phe
225                 230                 235                 240

Ile Gln Gln Cys Gly Trp Leu Ser His Asp Phe Leu His His Gln Val
                245                 250                 255

Phe Glu Thr Arg Trp Leu Asn Asp Val Val Gly Tyr Val Val Gly Asn
                260                 265                 270

Val Val Leu Gly Phe Ser Val Ser Trp Trp Lys Thr Lys His Asn Leu
        275                 280                 285

His His Ala Ala Pro Asn Glu Cys Asp Gln Lys Tyr Thr Pro Ile Asp
        290                 295                 300

Glu Asp Ile Asp Thr Leu Pro Ile Ile Ala Trp Ser Lys Asp Leu Leu
305                 310                 315                 320

Ala Thr Val Glu Ser Lys Thr Met Leu Arg Val Leu Gln Tyr Gln His
                325                 330                 335

Leu Phe Phe Leu Val Leu Leu Thr Phe Ala Arg Ala Ser Trp Leu Phe
                340                 345                 350

Trp Ser Ala Ala Phe Thr Leu Arg Pro Glu Leu Thr Leu Gly Glu Lys
                355                 360                 365

Leu Leu Glu Arg Gly Thr Met Ala Leu His Tyr Ile Trp Phe Asn Ser
                370                 375                 380

Val Ala Phe Tyr Leu Leu Pro Gly Trp Lys Pro Val Val Trp Met Val
385                 390                 395                 400

Val Ser Glu Leu Met Ser Gly Phe Leu Gly Tyr Val Phe Val Leu
                405                 410                 415

Ser His Asn Gly Met Glu Val Tyr Asn Thr Ser Lys Asp Phe Val Asn
                420                 425                 430
```

```
Ala Gln Ile Ala Ser Thr Arg Asp Ile Lys Ala Gly Val Phe Asn Asp
            435                 440                 445

Trp Phe Thr Gly Gly Leu Asn Arg Gln Ile Glu His His Leu Phe Pro
    450                 455                 460

Thr Met Pro Arg His Asn Leu Asn Lys Ile Ser Pro His Val Glu Thr
465                 470                 475                 480

Leu Cys Lys Lys His Gly Leu Val Tyr Glu Asp Val Ser Met Ala Ser
                485                 490                 495

Gly Thr Tyr Arg Val Leu Lys Thr Leu Lys Asp Val Ala Asp Ala Ala
            500                 505                 510

Ser His Gln Gln Leu Ala Ala Ser
            515                 520

<210> SEQ ID NO 7
<211> LENGTH: 525
<212> TYPE: PRT
<213> ORGANISM: Physcomitrella patens

<400> SEQUENCE: 7

Met Val Phe Ala Gly Gly Gly Leu Gln Gln Gly Ser Leu Glu Glu Asn
1               5                   10                  15

Ile Asp Val Glu His Ile Ala Ser Met Ser Leu Phe Ser Asp Phe Phe
            20                  25                  30

Ser Tyr Val Ser Ser Thr Val Gly Ser Trp Ser Val His Ser Ile Gln
        35                  40                  45

Pro Leu Lys Arg Leu Thr Ser Lys Lys Arg Val Ser Glu Ser Ala Ala
    50                  55                  60

Val Gln Cys Ile Ser Ala Glu Val Gln Arg Asn Ser Ser Thr Gln Gly
65                  70                  75                  80

Thr Ala Glu Ala Leu Ala Glu Ser Val Val Lys Pro Thr Arg Arg Arg
                85                  90                  95

Ser Ser Gln Trp Lys Lys Ser Thr His Pro Leu Ser Glu Val Ala Val
            100                 105                 110

His Asn Lys Pro Ser Asp Cys Trp Ile Val Val Lys Asn Lys Val Tyr
        115                 120                 125

Asp Val Ser Asn Phe Ala Asp Glu His Pro Gly Gly Ser Val Ile Ser
    130                 135                 140

Thr Tyr Phe Gly Arg Asp Gly Thr Asp Val Phe Ser Ser Phe His Ala
145                 150                 155                 160

Ala Ser Thr Trp Lys Ile Leu Gln Asp Phe Tyr Ile Gly Asp Val Glu
                165                 170                 175

Arg Val Glu Pro Thr Pro Glu Leu Leu Lys Asp Phe Arg Glu Met Arg
            180                 185                 190

Ala Leu Phe Leu Arg Glu Gln Leu Phe Lys Ser Ser Lys Leu Tyr Tyr
        195                 200                 205

Val Met Lys Leu Leu Thr Asn Val Ala Ile Phe Ala Ala Ser Ile Ala
    210                 215                 220

Ile Ile Cys Trp Ser Lys Thr Ile Ser Ala Val Leu Ala Ser Ala Cys
225                 230                 235                 240

Met Met Ala Leu Cys Phe Gln Gln Cys Gly Trp Leu Ser His Asp Phe
                245                 250                 255

Leu His Asn Gln Val Phe Glu Thr Arg Trp Leu Asn Glu Val Val Gly
            260                 265                 270

Tyr Val Ile Gly Asn Ala Val Leu Gly Phe Ser Thr Gly Trp Trp Lys
```

```
            275                 280                 285
Glu Lys His Asn Leu His His Ala Ala Pro Asn Glu Cys Asp Gln Thr
    290                 295                 300

Tyr Gln Pro Ile Asp Glu Asp Ile Asp Thr Leu Pro Leu Ile Ala Trp
305                 310                 315                 320

Ser Lys Asp Ile Leu Ala Thr Val Glu Asn Lys Thr Phe Leu Arg Ile
                325                 330                 335

Leu Gln Tyr Gln His Leu Phe Phe Met Gly Leu Leu Phe Phe Ala Arg
            340                 345                 350

Gly Ser Trp Leu Phe Trp Ser Trp Arg Tyr Thr Ser Thr Ala Val Leu
        355                 360                 365

Ser Pro Val Asp Arg Leu Leu Glu Lys Gly Thr Val Leu Phe His Tyr
    370                 375                 380

Phe Trp Phe Val Gly Thr Ala Cys Tyr Leu Leu Pro Gly Trp Lys Pro
385                 390                 395                 400

Leu Val Trp Met Ala Val Thr Glu Leu Met Ser Gly Met Leu Leu Gly
                405                 410                 415

Phe Val Phe Val Leu Ser His Asn Gly Met Glu Val Tyr Asn Ser Ser
            420                 425                 430

Lys Glu Phe Val Ser Ala Gln Ile Val Ser Thr Arg Asp Ile Lys Gly
        435                 440                 445

Asn Ile Phe Asn Asp Trp Phe Thr Gly Gly Leu Asn Arg Gln Ile Glu
    450                 455                 460

His His Leu Phe Pro Thr Met Pro Arg His Asn Leu Asn Lys Ile Ala
465                 470                 475                 480

Pro Arg Val Glu Val Phe Cys Lys Lys His Gly Leu Val Tyr Glu Asp
                485                 490                 495

Val Ser Ile Ala Thr Gly Thr Cys Lys Val Leu Lys Ala Leu Lys Glu
            500                 505                 510

Val Ala Glu Ala Ala Glu Gln His Ala Thr Thr Ser
        515                 520                 525

<210> SEQ ID NO 8
<211> LENGTH: 457
<212> TYPE: PRT
<213> ORGANISM: Mortierella alpina

<400> SEQUENCE: 8

Met Ala Ala Ala Pro Ser Val Arg Thr Phe Thr Arg Ala Glu Ile Leu
1               5                   10                  15

Asn Ala Glu Ala Leu Asn Glu Gly Lys Lys Asp Ala Glu Ala Pro Phe
            20                  25                  30

Leu Met Ile Ile Asp Asn Lys Val Tyr Asp Val Arg Glu Phe Val Pro
        35                  40                  45

Asp His Pro Gly Gly Ser Val Ile Leu Thr His Val Gly Lys Asp Gly
    50                  55                  60

Thr Asp Val Phe Asp Thr Phe His Pro Glu Ala Ala Trp Glu Thr Leu
65                  70                  75                  80

Ala Asn Phe Tyr Val Gly Asp Ile Asp Glu Ser Asp Arg Ala Ile Lys
                85                  90                  95

Asn Asp Asp Phe Ala Ala Glu Val Arg Lys Leu Arg Thr Leu Phe Gln
            100                 105                 110

Ser Leu Gly Tyr Tyr Asp Ser Ser Lys Ala Tyr Tyr Ala Phe Lys Val
        115                 120                 125
```

```
Ser Phe Asn Leu Cys Ile Trp Gly Leu Ser Thr Phe Ile Val Ala Lys
    130                 135                 140

Trp Gly Gln Thr Ser Thr Leu Ala Asn Val Leu Ser Ala Ala Leu Leu
145                 150                 155                 160

Gly Leu Phe Trp Gln Gln Cys Gly Trp Leu Ala His Asp Phe Leu His
            165                 170                 175

His Gln Val Phe Gln Asp Arg Phe Trp Gly Asp Leu Phe Gly Ala Phe
        180                 185                 190

Leu Gly Gly Val Cys Gln Gly Phe Ser Ser Trp Trp Lys Asp Lys
            195                 200                 205

His Asn Thr His His Ala Ala Pro Asn Val His Gly Glu Asp Pro Asp
    210                 215                 220

Ile Asp Thr His Pro Leu Leu Thr Trp Ser Glu His Ala Leu Glu Met
225                 230                 235                 240

Phe Ser Asp Val Pro Asp Glu Glu Leu Thr Arg Met Trp Ser Arg Phe
                245                 250                 255

Met Val Leu Asn Gln Thr Trp Phe Tyr Phe Pro Ile Leu Ser Phe Ala
            260                 265                 270

Arg Leu Ser Trp Cys Leu Gln Ser Ile Met Phe Val Leu Pro Asn Gly
        275                 280                 285

Gln Ala His Lys Pro Ser Gly Ala Arg Val Pro Ile Ser Leu Val Glu
    290                 295                 300

Gln Leu Ser Leu Ala Met His Trp Thr Trp Tyr Leu Ala Thr Met Phe
305                 310                 315                 320

Leu Phe Ile Lys Asp Pro Val Asn Met Ile Val Tyr Phe Leu Val Ser
                325                 330                 335

Gln Ala Val Cys Gly Asn Leu Leu Ala Ile Val Phe Ser Leu Asn His
            340                 345                 350

Asn Gly Met Pro Val Ile Ser Lys Glu Glu Ala Val Asp Met Asp Phe
        355                 360                 365

Phe Thr Lys Gln Ile Ile Thr Gly Arg Asp Val His Pro Gly Leu Phe
    370                 375                 380

Ala Asn Trp Phe Thr Gly Gly Leu Asn Tyr Gln Ile Glu His His Leu
385                 390                 395                 400

Phe Pro Ser Met Pro Arg His Asn Phe Ser Lys Ile Gln Pro Ala Val
                405                 410                 415

Glu Thr Leu Cys Lys Lys Tyr Gly Val Arg Tyr His Thr Thr Gly Met
            420                 425                 430

Ile Glu Gly Thr Ala Glu Val Phe Ser Arg Leu Asn Gly Val Ser Lys
        435                 440                 445

Ala Ala Ser Lys Met Gly Lys Ala Gln
    450                 455

<210> SEQ ID NO 9
<211> LENGTH: 443
<212> TYPE: PRT
<213> ORGANISM: Caenorhabditis elegans

<400> SEQUENCE: 9

Met Val Val Asp Lys Asn Ala Ser Gly Leu Arg Met Lys Val Asp Gly
1               5                   10                  15

Lys Trp Leu Tyr Leu Ser Glu Glu Leu Val Lys Lys His Pro Gly Gly
            20                  25                  30

Ala Val Ile Glu Gln Tyr Arg Asn Ser Asp Ala Thr His Ile Phe His
        35                  40                  45
```

Ala Phe His Glu Gly Ser Ser Gln Ala Tyr Lys Gln Leu Asp Leu Leu
 50                  55                  60

Lys Lys His Gly Glu His Asp Glu Phe Leu Glu Lys Gln Leu Glu Lys
 65                  70                  75                  80

Arg Leu Asp Lys Val Asp Ile Asn Val Ser Ala Tyr Asp Val Ser Val
                     85                  90                  95

Ala Gln Glu Lys Lys Met Val Glu Ser Phe Glu Lys Leu Arg Gln Lys
             100                 105                 110

Leu His Asp Asp Gly Leu Met Lys Ala Asn Glu Thr Tyr Phe Leu Phe
         115                 120                 125

Lys Ala Ile Ser Thr Leu Ser Ile Met Ala Phe Ala Phe Tyr Leu Gln
 130                 135                 140

Tyr Leu Gly Trp Tyr Ile Thr Ser Ala Cys Leu Leu Ala Leu Ala Trp
 145                 150                 155                 160

Gln Gln Phe Gly Trp Leu Thr His Glu Phe Cys His Gln Gln Pro Thr
                 165                 170                 175

Lys Asn Arg Pro Leu Asn Asp Thr Ile Ser Leu Phe Phe Gly Asn Phe
             180                 185                 190

Leu Gln Gly Phe Ser Arg Asp Trp Trp Lys Asp Lys His Asn Thr His
         195                 200                 205

His Ala Ala Thr Asn Val Ile Asp His Asp Gly Asp Ile Asp Leu Ala
 210                 215                 220

Pro Leu Phe Ala Phe Ile Pro Gly Asp Leu Cys Lys Tyr Lys Ala Ser
225                  230                 235                 240

Phe Glu Lys Ala Ile Leu Lys Ile Val Pro Tyr Gln His Leu Tyr Phe
                 245                 250                 255

Thr Ala Met Leu Pro Met Leu Arg Phe Ser Trp Thr Gly Gln Ser Val
             260                 265                 270

Gln Trp Val Phe Lys Glu Asn Gln Met Glu Tyr Lys Val Tyr Gln Arg
         275                 280                 285

Asn Ala Phe Trp Glu Gln Ala Thr Ile Val Gly His Trp Ala Trp Val
 290                 295                 300

Phe Tyr Gln Leu Phe Leu Pro Thr Trp Pro Leu Arg Val Ala Tyr
305                  310                 315                 320

Phe Ile Ile Ser Gln Met Gly Gly Leu Leu Ile Ala His Val Val
                 325                 330                 335

Thr Phe Asn His Asn Ser Val Asp Lys Tyr Pro Ala Asn Ser Arg Ile
             340                 345                 350

Leu Asn Asn Phe Ala Ala Leu Gln Ile Leu Thr Thr Arg Asn Met Thr
         355                 360                 365

Pro Ser Pro Phe Ile Asp Trp Leu Trp Gly Gly Leu Asn Tyr Gln Ile
 370                 375                 380

Glu His His Leu Phe Pro Thr Met Pro Arg Cys Asn Leu Asn Ala Cys
385                  390                 395                 400

Val Lys Tyr Val Lys Glu Trp Cys Lys Glu Asn Asn Leu Pro Tyr Leu
                 405                 410                 415

Val Asp Asp Tyr Phe Asp Gly Tyr Ala Met Asn Leu Gln Gln Leu Lys
             420                 425                 430

Asn Met Ala Glu His Ile Gln Ala Lys Ala Ala
         435                 440

<210> SEQ ID NO 10
<211> LENGTH: 448

<212> TYPE: PRT
<213> ORGANISM: Echium plantagineum

<400> SEQUENCE: 10

```
Met Ala Asn Ala Ile Lys Lys Tyr Ile Thr Ala Glu Glu Leu Lys Lys
1               5                   10                  15

His Asp Lys Ala Gly Asp Leu Trp Ile Ser Ile Gln Gly Lys Ile Tyr
            20                  25                  30

Asp Val Ser Asp Trp Leu Lys Asp His Pro Gly Gly Asn Phe Pro Leu
        35                  40                  45

Leu Ser Leu Ala Gly Gln Glu Val Thr Asp Ala Phe Val Ala Phe His
    50                  55                  60

Ser Gly Thr Thr Trp Lys Leu Leu Glu Lys Phe Phe Thr Gly Tyr Tyr
65                  70                  75                  80

Leu Lys Asp Tyr Ser Val Ser Glu Val Ser Lys Asp Tyr Arg Lys Leu
                85                  90                  95

Val Phe Glu Phe Asn Lys Met Gly Leu Phe Asp Lys Lys Gly His Ile
            100                 105                 110

Val Leu Val Thr Val Leu Phe Ile Ala Met Leu Phe Gly Met Ser Val
        115                 120                 125

Tyr Gly Val Leu Phe Cys Glu Gly Val Leu Val His Leu Leu Ala Gly
    130                 135                 140

Gly Leu Met Gly Phe Val Trp Ile Gln Ser Gly Trp Ile Gly His Asp
145                 150                 155                 160

Ala Gly His Tyr Ile Val Met Pro Asp Ala Arg Leu Asn Lys Leu Met
                165                 170                 175

Gly Ile Val Ala Ala Asn Cys Leu Ser Gly Ile Ser Ile Gly Trp Trp
            180                 185                 190

Lys Trp Asn His Asn Ala His His Ile Ala Cys Asn Ser Leu Asp Tyr
        195                 200                 205

Asp Pro Asp Leu Gln Tyr Ile Pro Phe Leu Val Val Ser Ser Lys Leu
    210                 215                 220

Phe Ser Ser Leu Thr Ser His Phe Tyr Glu Lys Lys Leu Thr Phe Asp
225                 230                 235                 240

Ser Leu Ser Arg Phe Phe Val Ser His Gln His Trp Thr Phe Tyr Pro
                245                 250                 255

Val Met Cys Met Ala Arg Val Asn Met Phe Val Gln Ser Leu Ile Met
            260                 265                 270

Leu Leu Thr Lys Arg Asn Val Phe Tyr Arg Ser Gln Glu Leu Leu Gly
        275                 280                 285

Leu Val Val Phe Trp Ile Trp Tyr Pro Leu Leu Val Ser Cys Leu Pro
    290                 295                 300

Asn Trp Gly Glu Arg Val Met Phe Val Val Ala Ser Leu Ser Val Thr
305                 310                 315                 320

Gly Met Gln Gln Val Gln Phe Ser Leu Asn His Phe Ser Ser Ser Val
                325                 330                 335

Tyr Val Gly Gln Pro Lys Gly Asn Asp Trp Phe Glu Lys Gln Thr Cys
            340                 345                 350

Gly Thr Leu Asp Ile Ser Cys Pro Ser Trp Met Asp Trp Phe His Gly
        355                 360                 365

Gly Leu Gln Phe Gln Val Glu His His Leu Phe Pro Lys Leu Pro Arg
    370                 375                 380

Cys His Leu Arg Lys Ile Ser Pro Phe Val Met Glu Leu Cys Lys Lys
385                 390                 395                 400
```

```
His Asn Leu Ser Tyr Asn Cys Ala Ser Phe Ser Glu Ala Asn Asn Met
                405                 410                 415

Thr Leu Arg Thr Leu Arg Asp Thr Ala Leu Gln Ala Arg Asp Leu Thr
            420                 425                 430

Lys Pro Leu Pro Lys Asn Leu Val Trp Glu Ala Leu Asn Thr His Gly
        435                 440                 445

<210> SEQ ID NO 11
<211> LENGTH: 448
<212> TYPE: PRT
<213> ORGANISM: Echium gentianoides

<400> SEQUENCE: 11

Met Ala Asn Ala Ile Lys Lys Tyr Ile Thr Ala Glu Glu Leu Lys Lys
1               5                   10                  15

His Asp Lys Glu Gly Asp Leu Trp Ile Ser Ile Gln Gly Lys Val Tyr
            20                  25                  30

Asp Val Ser Asp Trp Leu Lys Asp His Pro Gly Gly Lys Phe Pro Leu
        35                  40                  45

Leu Ser Leu Ala Gly Gln Glu Val Thr Asp Ala Phe Val Ala Phe His
    50                  55                  60

Ser Gly Ser Thr Trp Lys Phe Leu Asp Ser Phe Phe Thr Gly Tyr Tyr
65                  70                  75                  80

Leu Lys Asp Tyr Ser Val Ser Glu Val Ser Lys Asp Tyr Arg Lys Leu
                85                  90                  95

Val Phe Glu Phe Asn Lys Met Gly Leu Phe Asp Lys Lys Gly His Ile
            100                 105                 110

Val Leu Val Thr Val Leu Phe Ile Ala Met Met Phe Ala Met Ser Val
        115                 120                 125

Tyr Gly Val Leu Phe Cys Glu Gly Val Leu Val His Leu Leu Ala Gly
    130                 135                 140

Gly Leu Met Gly Phe Val Trp Ile Gln Ser Gly Trp Ile Gly His Asp
145                 150                 155                 160

Ala Gly His Tyr Ile Val Met Pro Asn Pro Arg Leu Asn Lys Leu Met
                165                 170                 175

Gly Ile Val Ala Gly Asn Cys Leu Ser Gly Ile Ser Ile Gly Trp Trp
            180                 185                 190

Lys Trp Asn His Asn Ala His His Ile Ala Cys Asn Ser Leu Asp Tyr
        195                 200                 205

Asp Pro Asp Leu Gln Tyr Ile Pro Phe Leu Val Val Ser Ser Lys Leu
    210                 215                 220

Phe Ser Ser Leu Thr Ser His Phe Tyr Glu Lys Lys Leu Thr Phe Asp
225                 230                 235                 240

Ser Leu Ser Arg Phe Phe Val Ser His Gln His Trp Thr Phe Tyr Pro
                245                 250                 255

Val Met Cys Ser Ala Arg Val Asn Met Phe Val Gln Ser Leu Ile Met
            260                 265                 270

Leu Leu Thr Lys Arg Asn Val Phe Tyr Arg Ser Gln Glu Leu Leu Gly
        275                 280                 285

Leu Val Val Phe Trp Ile Trp Tyr Pro Leu Leu Val Ser Cys Leu Pro
    290                 295                 300

Asn Trp Gly Glu Arg Ile Met Phe Val Val Ala Ser Leu Ser Val Thr
305                 310                 315                 320

Gly Met Gln Gln Val Gln Phe Ser Leu Asn His Phe Ser Ala Ser Val
```

```
                  325                 330                 335
Tyr Val Gly Gln Pro Lys Gly Asn Asp Trp Phe Glu Lys Gln Thr Cys
            340                 345                 350

Gly Thr Leu Asp Ile Ser Cys Pro Ser Trp Met Asp Trp Phe His Gly
            355                 360                 365

Gly Leu Gln Phe Gln Val Glu His His Leu Phe Pro Lys Leu Pro Arg
            370                 375                 380

Cys His Leu Arg Lys Ile Ser Pro Phe Val Met Glu Leu Cys Lys Lys
385                 390                 395                 400

His Asn Leu Ser Tyr Asn Cys Ala Ser Phe Ser Glu Ala Asn Glu Met
            405                 410                 415

Thr Leu Arg Thr Leu Arg Asp Thr Ala Leu Gln Ala Arg Asp Leu Thr
            420                 425                 430

Lys Pro Leu Pro Lys Asn Leu Val Trp Glu Ala Leu Asn Thr His Gly
            435                 440                 445

<210> SEQ ID NO 12
<211> LENGTH: 448
<212> TYPE: PRT
<213> ORGANISM: Echium pitardii

<400> SEQUENCE: 12

Met Ala Asn Ala Ile Lys Lys Tyr Ile Thr Ala Glu Glu Leu Lys Lys
1               5                   10                  15

His Asp Lys Glu Gly Asp Leu Trp Ile Ser Ile Gln Gly Lys Val Tyr
            20                  25                  30

Asp Val Ser Asp Trp Leu Lys Asp His Pro Gly Gly Lys Phe Pro Leu
        35                  40                  45

Leu Ser Leu Ala Gly Gln Glu Val Thr Asp Ala Phe Val Ala Phe His
    50                  55                  60

Ser Gly Ser Thr Trp Lys Leu Leu Asp Ser Phe Phe Thr Gly Tyr Tyr
65                  70                  75                  80

Leu Lys Asp Tyr Ser Val Ser Glu Val Ser Lys Asp Tyr Arg Lys Leu
                85                  90                  95

Val Phe Glu Phe Asn Lys Met Gly Leu Phe Asp Lys Lys Gly His Ile
            100                 105                 110

Val Leu Val Thr Val Phe Phe Ile Ala Met Met Phe Ala Met Ser Val
        115                 120                 125

Tyr Gly Val Leu Phe Cys Glu Gly Val Leu Val His Leu Leu Ala Gly
    130                 135                 140

Gly Leu Met Gly Phe Val Trp Ile Gln Ser Gly Trp Ile Gly His Asp
145                 150                 155                 160

Ala Gly His Tyr Ile Val Met Pro Asn Pro Lys Leu Asn Lys Leu Met
                165                 170                 175

Gly Ile Val Ala Ser Asn Cys Leu Ser Gly Ile Ser Ile Gly Trp Trp
            180                 185                 190

Lys Trp Asn His Asn Ala His His Ile Ala Cys Asn Ser Leu Asp Tyr
        195                 200                 205

Asp Pro Asp Leu Gln Tyr Ile Pro Phe Leu Val Val Ser Ser Lys Leu
    210                 215                 220

Phe Ser Ser Leu Thr Ser His Phe Tyr Glu Lys Lys Leu Thr Phe Asp
225                 230                 235                 240

Ser Leu Ser Arg Phe Phe Val Ser His Gln His Trp Thr Phe Tyr Pro
                245                 250                 255
```

Val Met Cys Ser Ala Arg Val Asn Met Phe Val Gln Ser Leu Ile Met
        260                 265                 270

Leu Leu Thr Lys Arg Asn Val Phe Tyr Arg Ser Gln Glu Leu Leu Gly
            275                 280                 285

Leu Val Val Phe Trp Ile Trp Tyr Pro Leu Leu Val Ser Cys Leu Pro
        290                 295                 300

Asn Trp Gly Glu Arg Ile Met Phe Val Val Ala Ser Leu Ser Val Thr
305                 310                 315                 320

Gly Leu Gln Gln Val Gln Phe Ser Leu Asn His Phe Ala Ala Ser Val
            325                 330                 335

Tyr Val Gly Gln Pro Lys Gly Ile Asp Trp Phe Glu Lys Gln Thr Cys
        340                 345                 350

Gly Thr Leu Asp Ile Ser Cys Pro Ser Trp Met Asp Trp Phe His Gly
            355                 360                 365

Gly Leu Gln Phe Gln Val Glu His His Leu Phe Pro Lys Leu Pro Arg
        370                 375                 380

Cys His Leu Arg Lys Ile Ser Pro Phe Val Met Glu Leu Cys Lys Lys
385                 390                 395                 400

His Asn Leu Ser Tyr Asn Cys Ala Ser Phe Ser Gln Ala Asn Glu Met
            405                 410                 415

Thr Leu Arg Thr Leu Arg Asp Thr Ala Leu Gln Ala Arg Asp Leu Thr
        420                 425                 430

Lys Pro Leu Pro Lys Asn Leu Val Trp Glu Ala Leu Asn Thr His Gly
            435                 440                 445

<210> SEQ ID NO 13
<211> LENGTH: 444
<212> TYPE: PRT
<213> ORGANISM: Danio rerio

<400> SEQUENCE: 13

Met Gly Gly Gly Gly Gln Gln Thr Asp Arg Ile Thr Asp Thr Asn Gly
1               5                   10                  15

Arg Phe Ser Ser Tyr Thr Trp Glu Glu Val Gln Lys His Thr Lys His
            20                  25                  30

Gly Asp Gln Trp Val Val Glu Arg Lys Val Tyr Asn Val Ser Gln
        35                  40                  45

Trp Val Lys Arg His Pro Gly Gly Leu Arg Ile Leu Gly His Tyr Ala
    50                  55                  60

Gly Glu Asp Ala Thr Glu Ala Phe Thr Ala Phe His Pro Asn Leu Gln
65                  70                  75                  80

Leu Val Arg Lys Tyr Leu Lys Pro Leu Leu Ile Gly Glu Leu Glu Ala
                85                  90                  95

Ser Glu Pro Ser Gln Asp Arg Gln Lys Asn Ala Ala Leu Val Glu Asp
            100                 105                 110

Phe Arg Ala Leu Arg Glu Arg Leu Glu Ala Glu Gly Cys Phe Lys Thr
        115                 120                 125

Gln Pro Leu Phe Phe Ala Leu His Leu Gly His Ile Leu Leu Leu Glu
    130                 135                 140

Ala Ile Ala Phe Met Met Val Trp Tyr Phe Gly Thr Gly Trp Ile Asn
145                 150                 155                 160

Thr Leu Ile Val Ala Val Ile Leu Ala Thr Ala Gln Ser Gln Ala Gly
                165                 170                 175

Trp Leu Gln His Asp Phe Gly His Leu Ser Val Phe Lys Thr Ser Gly
            180                 185                 190

-continued

```
Met Asn His Leu Val His Lys Phe Val Ile Gly His Leu Lys Gly Ala
        195                 200                 205

Ser Ala Gly Trp Trp Asn His Arg His Phe Gln His Ala Lys Pro
    210                 215                 220

Asn Ile Phe Lys Lys Asp Pro Asp Val Asn Met Leu Asn Ala Phe Val
225                 230                 235                 240

Val Gly Asn Val Gln Pro Val Glu Tyr Gly Val Lys Lys Ile Lys His
                245                 250                 255

Leu Pro Tyr Asn His Gln His Lys Tyr Phe Phe Ile Gly Pro Pro
            260                 265                 270

Leu Leu Ile Pro Val Tyr Phe Gln Phe Gln Ile Phe His Asn Met Ile
        275                 280                 285

Ser His Gly Met Trp Val Asp Leu Leu Trp Cys Ile Ser Tyr Tyr Val
    290                 295                 300

Arg Tyr Phe Leu Cys Tyr Thr Gln Phe Tyr Gly Val Phe Trp Ala Ile
305                 310                 315                 320

Ile Leu Phe Asn Phe Val Arg Phe Met Glu Ser His Trp Phe Val Trp
                325                 330                 335

Val Thr Gln Met Ser His Ile Pro Met Asn Ile Asp Tyr Glu Lys Asn
            340                 345                 350

Gln Asp Trp Leu Ser Met Gln Leu Val Ala Thr Cys Asn Ile Glu Gln
        355                 360                 365

Ser Ala Phe Asn Asp Trp Phe Ser Gly His Leu Asn Phe Gln Ile Glu
    370                 375                 380

His His Leu Phe Pro Thr Val Pro Arg His Asn Tyr Trp Arg Ala Ala
385                 390                 395                 400

Pro Arg Val Arg Ala Leu Cys Glu Lys Tyr Gly Val Lys Tyr Gln Glu
                405                 410                 415

Lys Thr Leu Tyr Gly Ala Phe Ala Asp Ile Ile Arg Ser Leu Glu Lys
            420                 425                 430

Ser Gly Glu Leu Trp Leu Asp Ala Tyr Leu Asn Lys
        435                 440

<210> SEQ ID NO 14
<211> LENGTH: 8
<212> TYPE: PRT
<213> ORGANISM: Artificial
<220> FEATURE:
<223> OTHER INFORMATION: Conserved motif of d6 desaturases

<400> SEQUENCE: 14

Met Ala Asn Ala Ile Lys Lys Tyr
1               5

<210> SEQ ID NO 15
<211> LENGTH: 7
<212> TYPE: PRT
<213> ORGANISM: Artificial
<220> FEATURE:
<223> OTHER INFORMATION: Conserved motif of d6 desaturases

<400> SEQUENCE: 15

Glu Ala Leu Asn Thr His Gly
1               5

<210> SEQ ID NO 16
<211> LENGTH: 4
<212> TYPE: PRT
```

-continued

<213> ORGANISM: Artificial
<220> FEATURE:
<223> OTHER INFORMATION: Conserved motif of d6 desaturases

<400> SEQUENCE: 16

His Pro Gly Gly
1

<210> SEQ ID NO 17
<211> LENGTH: 29
<212> TYPE: DNA
<213> ORGANISM: Artificial
<220> FEATURE:
<223> OTHER INFORMATION: Oligonucleotide primer

<400> SEQUENCE: 17
actcgagcca ccatggctaa tgcaatcaa                                   29

<210> SEQ ID NO 18
<211> LENGTH: 28
<212> TYPE: DNA
<213> ORGANISM: Artificial
<220> FEATURE:
<223> OTHER INFORMATION: Oligonucleotide primer

<400> SEQUENCE: 18
cctcgagctc aaccatgagt attaagag                                    28

<210> SEQ ID NO 19
<211> LENGTH: 21
<212> TYPE: DNA
<213> ORGANISM: Artificial
<220> FEATURE:
<223> OTHER INFORMATION: Oligonucleotide primer

<400> SEQUENCE: 19
actctgtttc tgaggtgtcc a                                           21

<210> SEQ ID NO 20
<211> LENGTH: 24
<212> TYPE: DNA
<213> ORGANISM: Artificial
<220> FEATURE:
<223> OTHER INFORMATION: Oligonucleotide primer

<400> SEQUENCE: 20
catattaacc ctagccatac acat                                        24

<210> SEQ ID NO 21
<211> LENGTH: 22
<212> TYPE: DNA
<213> ORGANISM: Artificial
<220> FEATURE:
<223> OTHER INFORMATION: Oligonucleotide primer

<400> SEQUENCE: 21
ctccagcgat ggttgttgct at                                          22

<210> SEQ ID NO 22
<211> LENGTH: 20
<212> TYPE: DNA
<213> ORGANISM: Artificial
<220> FEATURE:
<223> OTHER INFORMATION: Oligonucleotide primer

<400> SEQUENCE: 22
aatgtctctg gtgacgtagc                                                  20

<210> SEQ ID NO 23
<211> LENGTH: 2070
<212> TYPE: DNA
<213> ORGANISM: Linum usitatissimum

<400> SEQUENCE: 23

```
ctagactcaa gcatacggac aagggtaaat aacatagtca ccagaacata ataaacaaaa      60
agtgcagaag caagactaaa aaaattagct atggacattc aggttcatat tggaaacatc     120
attatcctag tcttgtgacc atccttcctc ctgctctagt tgagaggcct tgggactaac     180
gagaggtcag ttgggatagc agatccttat cctggactag cctttctggt gtttcagagt     240
cttcgtgccg ccgtctacat ctatctccat taggtctgaa gatgactctt cacaccaacg     300
acgtttaagg tctctatcct actcctagct tgcaatacct ggcttgcaat acctggagca     360
tcgtgcacga tgattggata ctgtggagga ggagtgtttg ctgatttaga gctcccggtt     420
gggtgatttg acttcgattt cagtttaggc ttgttgaaat ttttcaggtt ccattgtgaa     480
gcctttagag cttgagcttc cttccatgtt aatgccttga tcgaattctc ctagagaaaa     540
gggaagtcga tctctgagta ttgaaatcga agtgcacatt tttttttcaac gtgtccaatc     600
aatccacaaa caaagcagaa gacaggtaat ctttcatact tatactgaca agtaatagtc     660
ttaccgtcat gcataataac gtctcgttcc ttcaagaggg gttttccgac atccataacg     720
acccgaagcc tcatgaaagc attagggaag aacttttggt tcttcttgtc atggccttta     780
taggtgtcag ccgagctcgc caattcccgt ccgactggcc ccgcaaaata ttcgaacggc     840
aagttatgga cttgcaacca taactccacg gtattgagca ggaccctattg tgaagactca     900
tctcatggag cttcagaatg tggttgtcag caaaccaatg accgaaatcc atcacatgac     960
ggacgtccag tgggtgagcg aaacgaaaca ggaagcgcct atctttcaga gtcgtgagct    1020
ccacaccgga ttccggcaac tacgtgttgg gcaggcttcg ccgtattaga gatatgttga    1080
ggcagaccca tctgtgccac tcgtacaatt acgagagttg tttttttttgt gattttccta    1140
gtttctcgtt gatggtgagc tcatattcta catcgtatgg tctctcaacg tcgtttcctg    1200
tcatctgata tcccgtcatt tgcatccacg tgcgccgcct cccgtgccaa gtccctaggt    1260
gtcatgcacg ccaaattggt ggtggtgcgg gctgccctgt gcttcttacc gatgggtgga    1320
ggttgagttt gggggtctcc gcggcgatgg tagtgggttg acggtttggt gtgggttgac    1380
ggcattgatc aatttacttc ttgcttcaaa ttctttggca gaaaacaatt cattagatta    1440
gaactggaaa ccagagtgat gagacggatt aagtcagatt ccaacagagt tacatctctt    1500
aagaaataat gtaacccctt tagactttat atatttgcaa ttaaaaaaat aatttaactt    1560
ttagactttta tatatagtttt taataactaa gtttaaccac tctattattt atatcgaaac    1620
tatttgtatg tctcccctct aaataaactt ggtattgtgt ttacagaacc tataatcaaa    1680
taatcaatac tcaactgaag tttgtgcagt taattgaagg gattaacggc caaaatgcac    1740
tagtattatc aaccgaatag attcacacta gatggccatt tccatcaata tcatcgccgt    1800
tcttcttctg tccacatatc ccctctgaaa cttgagagac acctgcactt cattgtcctt    1860
attacgtgtt acaaaatgaa acccatgcat ccatgcaaac tgaagaatgg cgcaagaacc    1920
cttccccctcc atttcttatg tggcgaccat ccatttcacc atctcccgct ataaaacacc    1980
cccatcactt cacctagaac atcatcacta cttgcttatc catccaaaag atacccacca    2040
tggatccctg cagtaaatcc cgggctcgag                                    2070
```

<210> SEQ ID NO 24
<211> LENGTH: 476
<212> TYPE: DNA
<213> ORGANISM: Linum usitatissimum

<400> SEQUENCE: 24

```
ctcgagcaag cttatgtgac gtgaaataat aacggtaaaa tatatgtaat aataataata      60
ataaagccac aaagtgagaa tgaggggaag gggaaatgtg taatgagcca gtagccggtg     120
gtgctaattt tgtatcgtat tgtcaataaa tcatgaattt tgtggttttt atgtgttttt     180
ttaaatcatg aattttaaat tttataaaat aatctccaat cggaagaaca acattccata     240
tccatgcatg gatgtttctt tacccaaatc tagttcttga gaggcgttcc aaagatccca     300
aacgaaacat attatctata ctaatactat attattaatt actactgccc ggaatcacaa     360
tccctgaatg attcctatta actacaagcc ttgttggcgg cggagaagtg atcggcgcgg     420
cgagaagcag cggactcgga gacgaggcct tggaagatct gagtcgacac gggccc         476
```

<210> SEQ ID NO 25
<211> LENGTH: 1425
<212> TYPE: DNA
<213> ORGANISM: Echium plantagineum

<400> SEQUENCE: 25

```
atgaagcatc accgaacagt tctgcaacta tccctcaaaa gctttaaaat gaacaacaag      60
gaacagagca accaccatgg ctaatgcaat caagaagtac attactgcag aggagctgaa     120
gaagcatgat aaagcagggg atctctggat ctccattcaa ggaaaaatct atgatgtttc     180
agattggttg aaggaccatc caggtgggaa cttcccttg ctgagccttg ctggccaaga     240
ggtaactgat gcatttgttg catttcattc tggtacaact tggaagcttc ttgaaaaatt     300
cttcactggt tattacctta agattactc tgtttctgag gtgtccaaag attacaggaa     360
gcttgtgttt gagtttaata aaatgggctt gtttgacaaa aagggtcata ttgttcttgt     420
gactgtcttg tttatagcta tgttgtttgg tatgagtgtt tatggggttt tgttttgtga     480
gggtgttttg gtacatttgc ttgctggggg gttgatgggt tttgtctgga ttcagagtgg     540
ttggattggt catgatgctg gcattatat tgttatgcct gatgctaggc ttaataagct     600
tatgggtatt gttgctgcca attgtttatc tggaataagc attggttggt ggaaatggaa     660
ccataatgca catcacattg cctgtaatag cctcgattac gacccggatt gcagtacat     720
tccgtttctt gttgtgtcgt ccaagttgtt tagctcgctc acctctcatt tctatgaaaa     780
gaaactgaca tttgactctt tatcgagatt cttt gtaagc catcagcatt ggacgtttta     840
cccggttatg tgtatggcta gggttaatat gtttgtgcag tctctgataa tgttgttgac     900
taagcgaaat gtgttctata gaagtcaaga actgttggga ttggtggtgt tttggatttg     960
gtacccgttg cttgtttctt gcttgcctaa tggggagaa cgagtaatgt tcgttgttgc    1020
tagtctctcg gtgactggaa tgcaacaagt gcagttctct ttgaaccatt tctcgtcgag    1080
tgtttatgtt ggtcagccta aagggaacga ttggttcgag aaacaaacat gtgggacgct    1140
cgacatttct tgcccttcgt ggatggattg gtttcatggt ggattgcaat ccaagttga    1200
gcatcatttg ttccctaagc tgcccagatg ccaccttcgg aaaatctccc cgttcgtgat    1260
ggagttatgc aagaagcata attttgtctta caattgtgca tctttctccg aggccaacaa    1320
tatgacactc agaacattaa gggacacagc attgcaagct cgcgatttaa ccaagccgct    1380
```
ccccaagaat ttggtatggg aagctcttaa tactcatggt tgagc    1425

<210> SEQ ID NO 26
<211> LENGTH: 390
<212> TYPE: PRT
<213> ORGANISM: Perilla frutescens

<400> SEQUENCE: 26

Met Ala Val Ser Ser Gly Ala Arg Leu Ser Lys Ser Gly Ala Asp Gly
1               5                   10                  15

Glu Val Phe Asp Gly Gln Gln Gln Tyr Glu Gly Ile Gly Lys Arg Ala
            20                  25                  30

Ala Asp Lys Phe Asp Pro Ala Ala Pro Pro Phe Lys Ile Ala Asp
        35                  40                  45

Ile Arg Ala Ala Ile Pro Ala His Cys Trp Val Lys Ser Pro Trp Arg
50                  55                  60

Ser Leu Ser Tyr Val Val Trp Asp Val Ala Ala Val Ser Ala Arg Pro
65                  70                  75                  80

Ala Ala Val Tyr Ile Asn Ser Trp Ala Phe Trp Pro Val Tyr Trp Ile
                85                  90                  95

Ala Gln Gly Thr Met Phe Trp Ala Leu Phe Val Leu Gly His Asp Cys
            100                 105                 110

Gly His Gly Ser Phe Ser Asp Asn Thr Thr Leu Asn Asn Val Val Gly
        115                 120                 125

His Val Leu His Ser Ser Ile Leu Val Pro Tyr His Gly Trp Arg Ile
130                 135                 140

Ser His Arg Thr His His Gln Asn His Gly His Val Glu Lys Asp Glu
145                 150                 155                 160

Ser Trp Val Pro Leu Pro Glu Asn Leu Tyr Lys Lys Leu Asp Phe Ser
                165                 170                 175

Thr Lys Phe Leu Arg Tyr Lys Ile Pro Phe Pro Met Phe Ala Tyr Pro
            180                 185                 190

Leu Tyr Leu Trp Tyr Arg Ser Pro Gly Lys Thr Gly Ser His Phe Asn
        195                 200                 205

Pro Tyr Ser Asp Leu Phe Lys Pro Asn Glu Arg Gly Leu Ile Val Thr
210                 215                 220

Ser Thr Met Cys Trp Ala Ala Met Gly Val Phe Leu His Tyr Ala Thr
225                 230                 235                 240

Thr Ile Val Gly Pro Asn Met Met Phe Lys Leu Tyr Gly Val Pro Tyr
                245                 250                 255

Leu Ile Phe Val Met Trp Leu Asp Thr Val Thr Tyr Leu His His
            260                 265                 270

Gly Tyr Asp Lys Lys Leu Pro Trp Tyr Arg Ser Lys Glu Trp Ile Tyr
        275                 280                 285

Leu Arg Gly Gly Leu Thr Thr Val Asp Gln Asp Tyr Gly Phe Phe Asn
290                 295                 300

Lys Ile His His Asp Ile Gly Thr His Val Ile His His Leu Phe Pro
305                 310                 315                 320

Gln Ile Pro His Tyr His Leu Val Glu Ala Thr Arg Glu Ala Lys Arg
                325                 330                 335

Val Leu Gly Asn Tyr Tyr Arg Glu Pro Arg Lys Ser Gly Pro Val Pro
            340                 345                 350

Leu His Leu Ile Pro Ala Leu Leu Lys Ser Leu Gly Arg Asp His Tyr
        355                 360                 365

Val Ser Asp Asn Gly Asp Ile Val Tyr Tyr His Thr Val Asp Glu Leu
370                 375                 380

Phe Pro Ser Lys Lys Ile
385                 390

<210> SEQ ID NO 27
<211> LENGTH: 383
<212> TYPE: PRT
<213> ORGANISM: Brassica napus

<400> SEQUENCE: 27

Met Val Val Ala Met Asp Gln Arg Ser Asn Val Asn Gly Asp Ser Gly
1               5                   10                  15

Ala Arg Lys Glu Glu Gly Phe Asp Pro Ser Ala Gln Pro Pro Phe Lys
            20                  25                  30

Ile Gly Asp Ile Arg Ala Ala Ile Pro Lys His Cys Trp Val Lys Ser
        35                  40                  45

Pro Leu Arg Ser Met Ser Tyr Val Thr Arg Asp Ile Phe Ala Val Ala
    50                  55                  60

Ala Leu Ala Met Ala Ala Val Tyr Phe Asp Ser Trp Phe Leu Trp Pro
65                  70                  75                  80

Leu Tyr Trp Val Ala Gln Gly Thr Leu Phe Trp Ala Ile Phe Val Leu
                85                  90                  95

Gly His Asp Cys Gly His Gly Ser Phe Ser Asp Ile Pro Leu Leu Asn
            100                 105                 110

Ser Val Val Gly His Ile Leu His Ser Phe Ile Leu Val Pro Tyr His
        115                 120                 125

Gly Trp Arg Ile Ser His Arg Thr His His Gln Asn His Gly His Val
    130                 135                 140

Glu Asn Asp Glu Ser Trp Val Pro Leu Pro Glu Lys Leu Tyr Lys Asn
145                 150                 155                 160

Leu Pro His Ser Thr Arg Met Leu Arg Tyr Thr Val Pro Leu Pro Met
                165                 170                 175

Leu Ala Tyr Pro Ile Tyr Leu Trp Tyr Arg Ser Pro Gly Lys Glu Gly
            180                 185                 190

Ser His Phe Asn Pro Tyr Ser Ser Leu Phe Ala Pro Ser Glu Arg Lys
        195                 200                 205

Leu Ile Ala Thr Ser Thr Thr Cys Trp Ser Ile Met Leu Ala Thr Leu
    210                 215                 220

Val Tyr Leu Ser Phe Leu Val Asp Pro Val Thr Val Leu Lys Val Tyr
225                 230                 235                 240

Gly Val Pro Tyr Ile Ile Phe Val Met Trp Leu Asp Ala Val Thr Tyr
                245                 250                 255

Leu His His His Gly His Asp Glu Lys Leu Pro Trp Tyr Arg Gly Lys
            260                 265                 270

Glu Trp Ser Tyr Leu Arg Gly Gly Leu Thr Thr Ile Asp Arg Asp Tyr
        275                 280                 285

Gly Ile Phe Asn Asn Ile His His Asp Ile Gly Thr His Val Ile His
    290                 295                 300

His Leu Phe Pro Gln Ile Pro His Tyr His Leu Val Asp Ala Thr Arg
305                 310                 315                 320

Ala Ala Lys His Val Leu Gly Arg Tyr Tyr Arg Glu Pro Lys Thr Ser
                325                 330                 335

Gly Ala Ile Pro Ile His Leu Val Glu Ser Leu Val Ala Ser Ile Lys
            340                 345                 350

Lys Asp His Tyr Val Ser Asp Thr Gly Asp Ile Val Phe Tyr Glu Thr
            355                 360                 365

Asp Pro Asp Leu Tyr Val Tyr Ala Ser Asp Lys Ser Lys Ile Asn
370                 375                 380

<210> SEQ ID NO 28
<211> LENGTH: 386
<212> TYPE: PRT
<213> ORGANISM: Betula pendula

<400> SEQUENCE: 28

Met Lys Glu Pro Val Leu Glu Met Glu Asn Ala Gly Gly Phe Gly
1               5                   10                  15

Asn Gly Phe His Gly Val Val Glu Lys Asp Asp Phe Asp Pro Ser Ala
                20                  25                  30

Pro Pro Pro Phe Lys Ile Ala Glu Ile Arg Ala Ala Ile Pro Lys His
            35                  40                  45

Cys Trp Ala Lys Asn Pro Trp Arg Ser Leu Ser Tyr Ala Leu Arg Asp
50                  55                  60

Val Phe Val Val Ile Ala Leu Ala Ala Ala Ile Tyr Phe Lys Ala
65                  70                  75                  80

Trp Ile Phe Trp Pro Leu Tyr Trp Ala Ala Gln Gly Thr Met Phe Trp
                85                  90                  95

Ala Leu Phe Val Leu Gly His Asp Cys Gly His Gly Ser Phe Ser Asp
            100                 105                 110

Asn Pro Glu Leu Asn Asn Leu Val Gly His Val Leu His Ser Ala Ile
        115                 120                 125

Leu Val Pro Tyr His Gly Trp Arg Ile Ser His Arg Thr His His Gln
    130                 135                 140

Asn His Gly Asn Val Glu Asn Asp Glu Ser Trp Val Pro Leu Thr Glu
145                 150                 155                 160

Lys Leu Tyr Lys Ser Leu Gly Tyr Ser Thr Arg Leu Leu Arg Phe Thr
                165                 170                 175

Val Pro Phe Pro Leu Phe Ala Tyr Pro Ile Tyr Leu Trp Ser Arg Ser
            180                 185                 190

Pro Gly Lys Glu Gly Ser His Phe Asn Pro Tyr Ser Asn Leu Phe Ser
        195                 200                 205

Pro Asn Glu Arg Lys Asp Val Ile Thr Ser Thr Leu Cys Trp Ser Leu
    210                 215                 220

Met Ala Ala Leu Leu Ile Tyr Ser Ser Cys Ala Ile Gly Pro Ile Gln
225                 230                 235                 240

Met Leu Lys Leu Tyr Gly Val Pro His Leu Ile Phe Val Met Trp Leu
                245                 250                 255

Asp Leu Val Thr Tyr Leu His His His Gly Tyr Glu Gln Lys Leu Pro
            260                 265                 270

Trp Tyr Arg Gly Lys Glu Trp Ser Tyr Leu Arg Gly Gly Leu Thr Thr
        275                 280                 285

Val Asp Arg Asp Tyr Gly Trp Phe Asn Asn Ile His His Asp Ile Gly
    290                 295                 300

Thr His Val Ile His His Leu Phe Pro Gln Ile Pro His Tyr His Leu
305                 310                 315                 320

Val Glu Ala Thr Asn Ala Ala Lys Pro Val Leu Gly Lys Tyr Tyr Arg
                325                 330                 335

Glu Pro Lys Arg Ser Gly Pro Phe Pro Ile His Leu Ile Lys Asn Leu

```
                  340                 345                 350
Val Arg Ser Ile Ser Glu Asp His Tyr Val Asn Asp Asn Gly Asp Ile
            355                 360                 365

Val Tyr Tyr Gln Thr Asp Pro Glu Leu Tyr Lys Ser Ser Asn Thr Lys
            370                 375                 380

Ser Asp
385

<210> SEQ ID NO 29
<211> LENGTH: 386
<212> TYPE: PRT
<213> ORGANISM: Arabidopsis thaliana

<400> SEQUENCE: 29

Met Val Val Ala Met Asp Gln Arg Thr Asn Val Asn Gly Asp Pro Gly
1               5                   10                  15

Ala Gly Asp Arg Lys Lys Glu Glu Arg Phe Asp Pro Ser Ala Gln Pro
            20                  25                  30

Pro Phe Lys Ile Gly Asp Ile Arg Ala Ala Ile Pro Lys His Cys Trp
            35                  40                  45

Val Lys Ser Pro Leu Arg Ser Met Ser Tyr Val Arg Asp Ile Ile
    50                  55                  60

Ala Val Ala Ala Leu Ala Ile Ala Ala Val Tyr Val Asp Ser Trp Phe
65                  70                  75                  80

Leu Trp Pro Leu Tyr Trp Ala Ala Gln Gly Thr Leu Phe Trp Ala Ile
                85                  90                  95

Phe Val Leu Gly His Asp Cys Gly His Gly Ser Phe Ser Asp Ile Pro
            100                 105                 110

Leu Leu Asn Ser Val Val Gly His Ile Leu His Ser Phe Ile Leu Val
            115                 120                 125

Pro Tyr His Gly Trp Arg Ile Ser His Arg Thr His His Gln Asn His
    130                 135                 140

Gly His Val Glu Asn Asp Glu Ser Trp Val Pro Leu Pro Glu Arg Val
145                 150                 155                 160

Tyr Lys Lys Leu Pro His Ser Thr Arg Met Leu Arg Tyr Thr Val Pro
                165                 170                 175

Leu Pro Met Leu Ala Tyr Pro Leu Tyr Leu Cys Tyr Arg Ser Pro Gly
            180                 185                 190

Lys Glu Gly Ser His Phe Asn Pro Tyr Ser Ser Leu Phe Ala Pro Ser
            195                 200                 205

Glu Arg Lys Leu Ile Ala Thr Ser Thr Cys Trp Ser Ile Met Phe
    210                 215                 220

Val Ser Leu Ile Ala Leu Ser Phe Val Phe Gly Pro Leu Ala Val Leu
225                 230                 235                 240

Lys Val Tyr Gly Val Pro Tyr Ile Ile Phe Val Met Trp Leu Asp Ala
                245                 250                 255

Val Thr Tyr Leu His His His Gly His Asp Glu Lys Leu Pro Trp Tyr
            260                 265                 270

Arg Gly Lys Glu Trp Ser Tyr Leu Arg Gly Gly Leu Thr Thr Ile Asp
            275                 280                 285

Arg Asp Tyr Gly Ile Phe Asn Asn Ile His His Asp Ile Gly Thr His
    290                 295                 300

Val Ile His His Leu Phe Pro Gln Ile Pro His Tyr His Leu Val Asp
305                 310                 315                 320
```

```
Ala Thr Lys Ala Ala Lys His Val Leu Gly Arg Tyr Tyr Arg Glu Pro
            325                 330                 335

Lys Thr Ser Gly Ala Ile Pro Ile His Leu Val Glu Ser Leu Val Ala
            340                 345                 350

Ser Ile Lys Lys Asp His Tyr Val Ser Asp Thr Gly Asp Ile Val Phe
            355                 360                 365

Tyr Glu Thr Asp Pro Asp Leu Tyr Val Tyr Ala Ser Asp Lys Ser Lys
    370                 375                 380

Ile Asn
385

<210> SEQ ID NO 30
<211> LENGTH: 46
<212> TYPE: DNA
<213> ORGANISM: Artificial
<220> FEATURE:
<223> OTHER INFORMATION: Oligonucleotide primer

<400> SEQUENCE: 30
atccccgggt accggtcgcc accatggcta atgcaatcaa gaagta                    46

<210> SEQ ID NO 31
<211> LENGTH: 31
<212> TYPE: DNA
<213> ORGANISM: Artificial
<220> FEATURE:
<223> OTHER INFORMATION: Oligonucleotide primer

<400> SEQUENCE: 31
ttggagctca accatgagta ttaagagctt c                                    31
```

FEEDSTUFFS FOR AQUACULTURE COMPRISING STEARIDONIC ACID

CROSS-REFERENCE TO RELATED APPLICATIONS

This application is a divisional of U.S. Ser. No. 14/298,399, filed Jun. 6, 2014, which is a continuation of U.S. Ser. No. 12/085,261, filed Jun. 23, 2009, which is a § 371 national stage of PCT International Application No. PCT/AU2006/001737, filed Nov. 17, 2006, claiming the benefit of U.S. Provisional Application No. 60/737,946, filed Nov. 18, 2005, the contents of each of which are hereby incorporated by reference in their entirety.

REFERENCE TO SEQUENCE LISTING

This application incorporates-by-reference nucleotide and/or amino acid sequences which are present in the file named "171206_75520-AAA-PCT-US_Substitute_Sequence_Listing_DH.txt," which is 71.3 kilobytes in size, and which was created Dec. 6, 2017 in the IBM-PC machine format, having an operating system compatibility with MS-Windows, which is contained in the text file filed Dec. 6, 2017 as part of this application.

FIELD OF THE INVENTION

The present invention relates to feedstuffs for use in aquaculture, as well as methods for producing said feedstuffs. The invention also provides methods for rearing fish and/or crustaceans.

BACKGROUND OF THE INVENTION

Global production of farmed fish and crustacea has more than doubled in the last 15 years and its expansion places an increasing demand on global supplies of wild fish harvested to provide protein and oil as ingredients for aquafeeds (Naylor et al., 2000). The supply of seafood from global capture fisheries sources is around 100 million tones per annum (FAO, 2001). This amount has not increased since the mid-1980's and will not increase in the future as most fisheries are at or above sustainable levels of production, and are further subjected to sharp, periodic declines, due to climatic factors such as El Niño (FAO, 2001; Barlow 2000). Fish oil stocks are also under increasing demand not only from aquaculture, but from the agriculture and nutraceutical/biomedical industries.

Replacement oils for the aquaculture industry have been sourced from a variety of commercial terrestrial plant sources including sunflower (Bransden et al, 2003; Bell et al., 1993), canola/rapeseed (Bell et al, 2003; Polvi and Ackman, 1992), olive, palm (Fonseca-Madrigal et al, 2005; Bell et al, 2002) and linseed (Bell et al., 1993; Bell et al., 2004). The inclusion of vegetable oil to replace part or all of the fish oil in fish diets resulted in the same growth rates and feed conversion ratios (Bransden et al., 2003; Polvi and Ackman, 1992; Torstensen et al., 2004; Fonseca-Magrigal et al., 2005; Bell et al., 2002; Bell et al., 2004). However, since these plant oils had essentially no ω3 long-chain (≥C20) polyunsaturated fatty acids (ω3 LC-PUFA) and had high levels of monounsaturated fatty acids (MUFA), ω6 PUFA and low ω3/ω6 ratios, fish fed such diets displayed reduced levels of ω3 LC-PUFA. This is thought to be associated with reduced health benefits to the consumer compared to fish fed a diet high in fish oil containing greater levels of ω3 LC-PUFA (Seierstad et al., 2005). Therefore, raising fish or crustacea on diets high in vegetable oil has the potential to dilute the important cardiovascular and other benefits which are associated with eating fish.

Pathways of LC-PUFA Synthesis

Biosynthesis of LC-PUFA from linoleic and α-linolenic fatty acids in organisms such as microalgae, mosses and fungi may occur by a series of alternating oxygen-dependent desaturations and elongation reactions as shown schematically in FIG. 1. In one pathway (FIG. 1, II), the desaturation reactions are catalysed by Δ6, Δ5, and Δ4 desaturases, each of which adds an additional double bond into the fatty acid carbon chain, while each of a Δ6 and a Δ5 elongase reaction adds a two-carbon unit to lengthen the chain. The conversion of ALA to DHA in these organisms therefore requires three desaturations and two elongations. Genes encoding the enzymes required for the production of DHA in this aerobic pathway have been cloned from various microorganisms and lower plants including microalgae, mosses, fungi.

Alternative routes have been shown to exist for two sections of the ALA to DHA pathway in some groups of organisms. The conversion of ALA to ETA may be carried out by a combination of a Δ9 elongase and a Δ8 desaturase (the so-called Δ8 desaturation route, see FIG. 1, IV) in certain protists and thraustochytrids, as evidenced by the isolated of genes encoding such enzymes (Wallis and Browse, 1999; Qi et al., 2002). In mammals, the so-called "Sprecher" pathway converts DPA to DHA by three reactions, independent of a Δ4 desaturase (Sprecher et al., 1995).

Besides these desaturase/elongase systems, EPA and DHA can also be synthesized through an anaerobic pathway in a number of organisms such as *Shewanella, Mortiella* and *Schizochytrium* (Abbadi et al., 2001). The operons encoding these polyketide synthase (PKS) enzyme complexes have been cloned from some bacteria (Morita et al., 2000; Metz et al., 2001; Tanaka et al., 1999; Yazawa, 1996; Yu et al., 2000; WO 00/42195). The EPA PKS operon isolated from *Shewanella* spp has been expressed in *Synechococcus* allowing it to synthesize EPA (Takeyama et al., 1997). The genes encoding these enzymes are arranged in relatively large operons, and their expression in transgenic plants has not been reported. Therefore it remains to be seen if the anaerobic PKS-like system is a possible alternative to the more classic aerobic desaturase/elongase for the transgenic synthesis of LC-PUFA.

The biosynthetic pathways for PUFA are well known (Sargent et al., 2002). Vertebrates lack ω12 and ω15 (ω3) lipid desaturases and cannot produce linoleic acid (18:2 ω6, LA) and α-linolenic acid (18:3ω3, ALA) from oleic acid (18:1ω9, OA) (see FIG. 1). The conversion from ALA to eicosapentaenoic acid (20:5ω3, EPA) and docosahexaenoic acid (22:6ω3, DHA) is inefficient in marine fish, which have high levels of LC-PUFA in their natural diet, but is greater in freshwater fish, which have high levels of LA and ALA and limited DHA in their natural diet. High levels of ω3 LC-PUFA, which are found in salmon, cannot be biosynthesised from ALA and LA and therefore must be provided to the fish in their diet.

Desaturases

The desaturase enzymes that have been shown to participate in LC-PUFA biosynthesis all belong to the group of so-called "front-end" desaturases which are characterised by the presence of a cytochrome $b_5$ domain at the N-terminus of each protein. The cyt $b_5$ domain presumably acts as a receptor of electrons required for desaturation (Sperling and Heinz, 2001). The enzyme Δ6 desaturase catalyses the desaturation of linoleic acid (LA) to form gamma-linoleic acid (GLA, 18:3 ω6) and linolenic acid (ALA) to form stearidonic acid (SDA, 18:4 ω3) (FIG. 1). Genes encoding this enzyme have been isolated from a number of organisms, including plants, mammals, nematodes, fungi and marine microalgae. The C18 fatty acid substrate for Δ6 desaturases from plants, fungi and microalgae has desaturation in at least the Δ9 and Δ12 positions and is generally covalently linked to a phosphatidylcholine headgroup (acyl-PC).

The enzyme Δ5 desaturase catalyses the desaturation of C20 LC-PUFA leading to arachidonic acid (ARA, 20:4 ω6) and EPA (20:5ω3). Genes encoding this enzyme have been isolated from a number of organisms, including algae (*Thraustochytrium* sp. Qiu et al., 2001), fungi (M alpine, *Pythium irregulare*, Michaelson et al., 1998; Hong et al., 2002), *Caenorhabditis elegans* and mammals. A gene encoding a bifunctional Δ5-/Δ6-desaturase has also been identified from zebrafish (Hasting et al., 2001). The gene encoding this enzyme might represent an ancestral form of the "front-end desaturase" which later duplicated and evolved distinct functions.

The last desaturation step to produce DHA is catalysed by a Δ4 desaturase and a gene encoding this enzyme has been isolated from the freshwater protist species *Euglena gracilis* and the marine species *Thraustochytrium* sp. (Qiu et al., 2001; Meyer et al., 2003).

Elongases

Several genes encoding PUFA-elongation enzymes have also been isolated (Sayanova and Napier, 2004). The members of this gene family were unrelated to the elongase genes present in higher plants, such as FAE1 of *Arabidopsis*, that are involved in the extension of saturated and monounsaturated fatty acids. An example of the latter is erucic acid (22:1) in *Brassicas*. In some protist species, LC-PUFA are synthesized by elongation of linoleic or α-linolenic acid with a C2 unit, before desaturation with Δ8 desaturase (FIG. 1 part IV; "Δ8-desaturation" pathway). Δ6 desaturase and Δ6 elongase activities were not detected in these species. Instead, a Δ9-elongase activity would be expected in such organisms, and in support of this, a C18 Δ9-elongase gene has recently been isolated from *Isochrysis galbana* (Qi et al., 2002).

Transgenic Plants

Transgenic oilseed crops that are engineered to produce major LC-PUFA by the insertion of various genes encoding desaturases and/or elongases have been suggested as a sustainable source of nutritionally important fatty acids. However, the requirement for coordinate expression and activity of five new enzymes encoded by genes from possibly diverse sources has made this goal difficult to achieve and only low yields have generally been obtained (reviewed by Sayanova and Napier, 2004; Drexler et al., 2003; Abbadi et al., 2001).

A gene encoding a Δ6-fatty acid desaturase isolated from borage (*Borago* officinal's) was expressed in transgenic tobacco and *Arabidopsis*, resulting in the production of GLA (18:3ω6) and SDA (18:4 ω3), the direct precursors for LC-PUFA, in the transgenic plants (Sayanova et al., 1997 and 1999). However, this provides only a single, first step.

Feedstuffs for Aquaculture

Research in feedstuffs for aquaculture have largely focused on enriching salmon diets by increasing the dietary supply of ALA (Bell et al., 1993) and EPA/DHA (Harel et al., 2002; Carter et al., 2003).

There is a need for further diets for aquaculture which, upon consumption, enhance the production of omega-3 long chain polyunsaturated fatty acids in aquatic animals.

SUMMARY OF THE INVENTION

The present inventors have determined that fish and crustaceans can be produced with appropriate levels of LC-PUFA, such as EPA, DPA and/or DHA, without the need to feed these organisms diets which are rich in LC-PUFA. In particular, the LC-PUFA precursor stearidonic acid (SDA) can be provided to the fish or crustaceans whilst still producing fish or crustaceans with desirable levels of LC-PUFA.

Thus, in a first aspect, the present invention provides a method of rearing a fish or crustacean, the method comprising feeding the fish or crustacean a feedstuff comprising lipid, the fatty acid of said lipid comprising at least 5.5% (w/w) stearidonic acid (SDA).

In a preferred embodiment, the lipid comprises a phytosterol.

In a particularly preferred embodiment, at least 1% of the SDA in the feedstuff was obtained from a plant. The plant may be non-transgenic, such as an *Echium* sp., *Oenothera biennis, Borago officinalis* or *Ribes nigrum*, or transgenic. In an embodiment, at least some of the SDA is from oil obtained from seed of the plant.

In a preferred embodiment, the transgenic plant comprises an exogenous nucleic acid encoding a Δ6 desaturase. The transgenic plant may further comprise an exogenous nucleic acid encoding a ω3 desaturase or Δ15 desaturase, which increases the production of ALA in the plant. The transgenic plant may further comprise an exogenous nucleic acid encoding a Δ12 desaturase. Examples of suitable transgenic plants include, but are not limited to, canola, soybean, flax, other oilseed plants, cereals or grain legumes.

In a particularly preferred embodiment, the fish is a salmon.

In one embodiment, the fish or crustacean is fed predominantly the feedstuff over a period of at least 6 weeks, preferably at least 7 weeks and even more preferably at least 12 weeks. In an embodiment, after having been fed the feedstuff for at least 6 weeks, the fish or crustacean has similar weight, specific growth rate, weight gain, total feed consumption, feed efficiency ratio, hepatosomatic index and/or survival when compared with the same species of fish or crustacean fed the same feedstuff but which substantially lacks SDA.

In another embodiment, the fish or crustacean, after having been fed the feedstuff for at least 6 weeks, has higher SDA and/or ETA levels in muscle tissue when compared with the same species of fish or crustacean fed the same feedstuff but which substantially lacks SDA.

In a further embodiment, the fish or crustacean, after having been fed the feedstuff for at least 6 weeks, has lower SDA levels in muscle tissue when compared with the same species of fish or crustacean fed the same feedstuff but which comprises fish oil instead of the plant oil comprising at least 5.5% SDA. In preferred embodiments, the levels of 14:0 and 16:0 are reduced, for example by at least 10% or at least 20%.

In another aspect, the present invention provides a feedstuff for a fish or crustacean, the feedstuff comprising lipid, the fatty acid of said lipid comprising at least 5.5% (w/w) stearidonic acid (SDA, 18:4Δ6,9,12,15, ω33). The feedstuff may have any of the characteristics as described herein in the context of the methods.

In a further aspect, the present invention provides a fish or crustacean produced using a method of the invention.

In yet another aspect, the present invention provides a fish, wherein the fatty acid of the white muscle lipid of said fish comprises less than 29.6% SFA and at least 18.3% DHA. In certain embodiments, the white muscle lipid of the fish comprises fatty acid comprising less than 28%, less than 27%, or more preferably less than 26% SFA. In other embodiments, the white muscle lipid of the fish comprises fatty acid comprising at least 19%, at least 20%, at least 21%, or more preferably at least 22% DHA.

In another aspect, the present invention provides a fish, wherein the fatty acid of the red muscle lipid of said fish comprises fatty acid comprising less than 28.2% SFA and at least 9.6% DHA. In certain embodiments, the red muscle lipid of the fish comprises fatty acid comprising less than 27%, less than 26%, or more preferably less than 25% SFA. In other embodiments, the muscle lipid of the fish comprises fatty acid comprising at least 10%, at least 11%, or more preferably at least 12% DHA.

In a further aspect, the present invention provides a fish or crustacean, wherein the fatty acid of the muscle lipid of said fish or crustacean comprises at least 2.7% SDA. In embodiments of this aspect, the muscle lipid of said fish or crustacean comprises at least 3%, at least 3.5%, or more preferably at least 4% SDA.

In a further aspect, the present invention provides a fish, wherein the fatty acid of the white muscle lipid of said fish comprises at least 2.1% SDA. In embodiments of this aspect, the white muscle lipid of said fish comprises at least 2.5%, at least 3%, or more preferably at least 3.5% SDA.

Preferably, a fish of the invention is a salmon.

In yet a further aspect, the present invention provides a method for producing a feedstuff for fish and/or crustaceans, the method comprising admixing oil obtained from a plant with at least one other ingredient, wherein the fatty acid of said oil comprises at least 5.5% (w/w) SDA. In a preferred embodiment, the other ingredient comprises fish meal, a high protein source other than fishmeal, a starch source or a combination of these. Other ingredients may include vitamins, minerals, choline, or pigments such as, for example, carotenoids or carophyll pink.

Preferably, the plant is transgenic.

Preferably, the oil is obtained from the seed of the plant.

In certain embodiments, it is preferred that the fatty acid of said oil comprises at least 6%, at least 7%, at least 8%, at least 9%, at least 10%, at least 11.0%, at least 15%, at least 20%, or at least 30% (w/w) SDA.

In another aspect, the present invention provides a method for producing a feedstuff for fish and/or crustaceans, the method comprising admixing a transgenic organism, or extract or portion thereof, with at least one other ingredient, wherein the organism is genetically modified such that it produces SDA and/or produces higher levels of SDA than when compared to a corresponding non-transgenic wild-type organism. The method may comprise the step of extracting the oil from the organism, for example from the seed of a plant. The extraction may comprise physical means such as crushing of seed, chemical means such as extraction with a solvent, heating or other processes, or any combination of these. The oil may be further purified before mixing with other ingredients. The method preferably includes preparation of an extruded product from the mixed ingredients by an extrusion process, suitable for providing to fish or crustacean. The method may comprise the step of analysing the feedstuff such as for example measuring the level of lipid or the level of SDA in the fatty acid, or other measurements.

Preferably, the organism is a plant or yeast.

In another aspect, the present invention provides a feedstuff produced using a method of the invention. The feedstuff may have the characteristics as described above. Other ingredients that may be included in the feedstuff include fish meal, a high protein source other than fishmeal, a starch source, vitamins, minerals, pigments such as, for example, carotenoids or carophyll pink, or any combination of these. Fishmeal is a preferred protein source for the major carnivorous fish such as salmon, trout, tuna, flatfish, barramundi, particularly for Atlantic salmon. Fishmeal, typically about 65% protein, may be added in an amount from 20 to 700 g per kg dryweight. A high protein source other than fishmeal may be from a plant or animal source such as, for example, wheat or other cereal gluten, soymeal, meal from other legumes, casein, protein concentrates, protein isolates, meat, meat and bone, blood, feathers. These are typically at least 30% protein and may be milled with or without extraction of oil. Starch may be added, typically at 10-150 g/kg, and may be in the form of cereal grain or meal. For crustaceans, krill meal, mussel meal or other similar components may be added at 1-200 g/kg, cholesterol and/or lecithin at 0-100 g/kg. The mixture may comprise a binding agent such as sodium alginate, for example Manucol from Kelco International.

In a further aspect, the present invention provides oil extracted from a fish or crustacean of the invention, comprising SDA, EPA, DPA, DHA or any combinations thereof.

In yet another aspect, the present invention provides a cotton or flax plant capable of producing seed, wherein the oil of said seed comprises fatty acid comprising at least 5.5% SDA on a weight basis.

Furthermore, the present inventors have found that expressing a Δ6 desaturase gene in a fibre producing plant results in surprisingly high levels of Δ6 desaturase PUFA products.

Thus, in a further aspect the present invention provides a cotton or flax plant capable of producing seed, wherein the seed synthesizes GLA that is the product of Δ6-desaturation of LA and/or SDA that is the product of Δ6-desaturation of ALA, and wherein the efficiency of conversion of LA to GLA and/or ALA to SDA in the seed is at least 25%, at least 35%, or at least 45%. For example, at least 25%, preferably at least 45% of the polyunsaturated fatty acid in the cotton or flax seed that has a carbon chain of C18 or longer is desaturated at the Δ6 position.

Preferably, the cotton plant is *Gossypium hirstum* or *Gossypium barbadense*.

Preferably, the flax plant is *Linum usitatissimum*.

Preferably, the fatty acid of the oil comprises at least 8% SDA, or at least 10% SDA, at least 11% SDA, at least 15% SDA, at least 20% SDA, at least 25% SDA, at least 30% SDA, at least 35% SDA, at least 40% SDA, at least 45% SDA or at least 50% SDA.

In one preferred embodiment, the plant comprises a transgenic Δ6 desaturase gene. In another preferred embodiment, the plant comprises a transgenic Δ15 desaturase or ω3 desaturase gene which may be in additional to the transgenic Δ6 desaturase gene. In an embodiment, the protein coding region of said gene is from a plant, microalgal, fungal or vertebrate source.

Also provided is the seed of a plant of the invention, wherein the oil of said seed comprises fatty acid comprising at least 5.5% SDA on a weight basis.

In a further aspect, the present invention provides a method of producing a plant of the invention, comprising the introduction of a Δ6 desaturase gene into a cotton or flax plant cell and the regeneration of a plant therefrom.

In an embodiment, the method comprises the step of determining the fatty acid composition of seedoil obtained from seed of said plant and/or the step of selecting a plant on the basis of its seed oil composition.

In another embodiment, the method further comprises the introduction of a Δ15 desaturase or ω3 desaturase gene into said plant.

In yet a further aspect, the present invention provides a method of producing the seed of the invention, comprising growing said plant and harvesting seed from said plant.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

BRIEF DESCRIPTION OF THE ACCOMPANYING DRAWINGS

FIG. 1. Possible pathways of ω3 and ω6 LC-PUFA synthesis. The sectors labelled I, II, III, and IV correspond to the ω6 (Δ6), ω3 (Δ6), ω6 (Δ8), and ω3 (Δ8) pathways, respectively. Compounds in sectors I and III are ω6 compounds, while those in sectors II and IV are ω3 compounds. "Des" refers to desaturase steps in the pathway catalysed by desaturases as indicated, while "Elo" refers to elongase steps catalysed by elongases as indicated. The thickened arrow indicates the Δ5 elongase step. The dashed arrows indicate the steps in the "Sprecher" pathway that operates in mammalian cells for the production of DHA from DPA.

Figure 2:
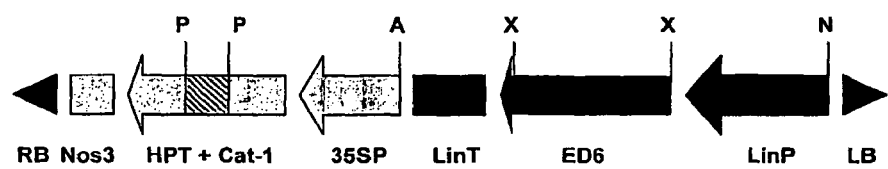

FIG. 2. Schematic representation of the construct, pVLin-Ed6, used to transform flax. RB, right border of T-DNA; HPT+Cat-1, hygromycin resistance gene interrupted by Cat-1 intron; 35SP, Cauliflower mosaic virus 35S promoter; LinT, Linin terminator; ED6, full length coding sequence of Δ6 fatty acid desaturase from Echium; LinP, linin promoter; LB, left border of T-DNA. P, PstI; A, ApaI; X, XhoI; N, NotI.

KEY TO THE SEQUENCE LISTING

SEQ ID NO:1—Δ6 desaturase from humans (Genbank Accession No: AAD20018).

SEQ ID NO:2—Δ6 desaturase from mouse (Genbank Accession No: NP_Δ62673).

SEQ ID NO:3—Δ6 desaturase from Pythium irregulare (Genbank Accession No: AAL13310).

SEQ ID NO:4—Δ6 desaturase from Borago officinalis (Genbank Accession No: AAD01410).

SEQ ID NO:5—Δ6 desaturase from Anemone leveillei (Genbank Accession No: AAQ10731).

SEQ ID NO:6—Δ6 desaturase from Ceratodon purpureus (Genbank Accession No: CAB94993).

SEQ ID NO:7—Δ6 desaturase from Physcomitrella patens (Genbank Accession No: CAA11033).

SEQ ID NO:8—Δ6 desaturase from Mortierella alpina (Genbank Accession No: BAC82361).

SEQ ID NO:9—Δ6 desaturase from Caenorhabditis elegans (Genbank Accession No: AAC15586).

SEQ ID NO:10—Δ6 desaturase from Echium plantagineum.

SEQ ID NO:11—Δ6 desaturase from Echium gentianoides (Genbank Accession No: AY055117).

SEQ ID NO:12—Δ6 desaturase from Echium pitardii (Genbank Accession No: AY055118).

SEQ ID NO:13—Δ5/Δ6 bifunctional desaturase from Danio rerio (zebrafish).

SEQ ID NO's 14 to 16—Conserved motifs of Echium sp. Δ6 desaturases.

SEQ ID NO's 17 to 22, 30 and 31—Oligonucleotide primers.

SEQ ID NO:23—Linin promoter from Linum usitatissimum.

SEQ ID NO:24—Linin terminator from Linum usitatissimum.

SEQ ID NO:25—cDNA sequence encoding Δ6 desaturase from Echium plantagineum.

SEQ ID NO:26—Δ15 desaturase from Perilla frutescens (Genbank Accession No: AF213482).

SEQ ID NO:27—Δ15 desaturase from Brassica napus (Genbank Accession No: L01418).

SEQ ID NO:28—Δ15 desaturase from Betula pendula (Genbank Accession No: AAN17504).

SEQ ID NO:29—Δ15 desaturase from Arabidposis thaliana (Genbank Accession No:AAC31854).

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, plant biology, molecular genetics, immunology, immunohistochemistry, fatty acid synthesis, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present), and are incorporated herein by reference.

As used herein, the term "lipid" generally refers to an organic molecule, typically containing a hydrocarbon chain(s), that is insoluble in water but dissolves readily in nonpolar organic solvents. Feedstuffs of the invention are defined herein relative to the composition of their lipid component. This lipid component includes fatty acids (either free or esterified, for example in the form of triacylglycerols), sterols and polar lipids.

As used herein, the term "fatty acids" refers to a large group of organic acids made up of molecules containing a carboxyl group at the end of a hydrocarbon chain; the carbon content may vary from C2 to C34. The fatty acids may be saturated (contain no double bonds in the carbon chain)

(SFA), monounsaturated (contain a single double bond in the carbon chain) (MUFA), or polyunsaturated (contain a two, three, four or more double bonds in the carbon chain) (PUPA). Unless stated to the contrary, the fatty acids may be in a free state (non-esterified) or in an esterified form such as part of a triacylglycerol, diacylglyceride, monoacylglyceride, acyl-CoA bound or other bound form, or mixture thereof. The fatty acid may be esterified as a phospholipid such as a phosphatidylcholine, phosphatidylethanolamine, phosphatidylserine, phosphatidylglycerol, phosphatidylinositol or diphosphatidylglycerol forms.

As used herein, the terms "long-chain polyunsaturated fatty acid", "LC-PUFA" or "C20+ polyunsaturated fatty acid" refer to a fatty acid which comprises at least 20 carbon atoms in its carbon chain and at least three carbon-carbon double bonds. Ordinarily, the number of carbon atoms in the carbon chain of the fatty acids refers to an unbranched carbon chain. If the carbon chain is branched, the number of carbon atoms excludes those in side groups. Generally, the long-chain polyunsaturated fatty acid is an ω3 fatty acid, that is, having a desaturation (carbon-carbon double bond) in the third carbon-carbon bond from the methyl end of the fatty acid. Preferably, the long-chain polyunsaturated fatty acid is selected from the group consisting of; eicosatetraenoic acid (ETA, 20:4Δ8,11,14,17, ω3) eicosapentaenoic acid (EPA, 20:5Δ5,8,11,14,17; ω3), docosapentaenoic acid (DPA, 22:5Δ7,10,13,16,19, ω3), or docosahexaenoic acid (DHA, 22:6Δ4,7,10,13,16,19, ω3). It would readily be apparent that the LC-PUFA that is in (or limited in amount or even excluded from) a feedstuff of the invention, or produced by a fish or crustacean fed a feedstuff of the invention, may be a mixture of any or all of the above and may include other LC-PUFA or derivatives of any of these LC-PUFA.

Use of the term "fish" includes all vertebrate fish, which may be bony or cartilaginous fish. The present invention may be practiced with any of the considerable variety of fresh, brackish, or salt water fish species including, but not limited to, salmon, trout, carp, bass, bream, turbot, sole, milkfish, grey mullet, grouper, flounder, sea bass, cod, haddock, Japanese flounder, catfish, char, whitefish, sturgeon, tench, roach, pike, pike-perch, yellowtail, tilapia, eel or tropical fish (such as the fresh, brackish, and salt water tropical fish). In an embodiment, the fish is not hybrid striped bass. In a further embodiment, if the fish is hybrid striped bass, the fatty acid of said lipid comprises at least 11.0%, at least 12% or at least 15% (w/w) SDA. In another embodiment, if the fish is hybrid striped bass, the SDA content of the feedstuff is at least 2.1% (w/w). Yet other species with which the present invention can be practiced will be apparent to those skilled in the art, including those species outlined in Table 1. The invention may be practised with any, all, or any combination of the listed fish.

TABLE 1

Fish that can be fed feedstuffs of the invention.

| Family | Scientific name | Common name |
|---|---|---|
| ACIPENSERIDAE | Acipenser baeri | Siberian sturgeon |
| | Acipenser ruthenus | Sterlet sturgeon |
| | Acipenser stellatus | Starry sturgeon |
| | Acipenser transmontanus | White sturgeon |
| | Huso huso | Beluga |
| OSTEOGLOSSIDAE | Arapaima gigas | Arapaima |
| | Anguilla japonica | Japanese eel |
| | Anguilla rostrata | American eel |
| | Anguilla australis | Short-finned eel |

TABLE 1-continued

Fish that can be fed feedstuffs of the invention.

| Family | Scientific name | Common name |
|---|---|---|
| | Anguilla reinhardtii | Long-finned eel |
| | Anguilla anguilla | European eel |
| CHANIDAE | Chanos chanos | Milkfish |
| CYPRINIDAE | Abramis brama | Freshwater bream |
| | Aspius aspius | Asp |
| | Catla catla | Catla |
| | Carassius auratus | Goldfish |
| | Carassius carassius | Crucian carp |
| | Cirrhinus molitorella | Mud carp |
| | Cirrhinus mrigala | Mrigal carp |
| | Ctenopharyngodon idellus | Grass carp |
| | Cyprinus carpio | Common carp |
| | Hypophthalmichthys molitrix | Silver carp |
| | Hypophthalmichthys nobilis | Bighead carp |
| | Labeo calbasu | Orangefin labeo |
| | Labeo rohita | Roho labeo |
| | Leptobarbus hoeveni | Hoven's carp |
| | Megalobrama amblycephala | Wuchang bream |
| | Mylopharyngodon piceus | Black carp |
| | Notemigonus crysoleucas | Golden shiner |
| | Osteochilus hasselti | Nilem carp |
| | Parabramis pekinensis | White amur bream |
| | Puntius gonionotus | Thai silver barb |
| | Puntius javanicus | Java |
| | Rutilus rutilus | Roach |
| | Tinca tinca | Tench |
| COBITIDAE | Misgurnus anguillicaudatus | Pond loach |
| CURIMATIDAE | Ichthyoelephas humeralis | Bocachico |
| | Prochilodus reticulatus | Bocachico |
| CHARACIDAE | Brycon moorei | Dorada |
| | Colossoma macropomum | Cachama |
| | Piaractus brachypomus | Cachama blanca |
| | Piaractus mesopotamicus | Paco |
| ICTALURIDAE | Ictalurus melas | Black bullhead |
| | Ictalurus punctatus | Channel catfish |
| BAGRIDAE | Chrysichthys nigrodigitatus | Bagrid catfish |
| SILURIDAE | Siluris glanis | Wels catfish |
| PANGASIIDAE | Pangasius pangasius | Pangas catfish |
| | Pangasius sutchi | Striped catfish |
| CLARIIDAE | Clarias anguillaris | Mudfish |
| | Clarias batrachus | Philippine catfish |
| | Clarias fuscus | Hong Kong catfish |
| | Clarias gariepinus | North African catfish |
| | Clarias macrocephalus | Bighead catfish |
| | Heterobranchus bidorsalis | African catfish |
| | Heterobranchus longifilis | Sampa |
| PIMELODIDAE | Rhamdia sapo | South American catfish |
| CALLICHTHYIDAE | Hoplosternum littorale | Atipa |
| ESOCIDAE | Esox lucius | Northern pike |
| PLECOGLOSSIDAE | Plecoglossus altivelis | Ayu sweetfish |
| SALMONIDAE | Coregonus albula | Vendace |
| | Coregonus lavaretus | Whitefish |
| | Oncorhynchus gorbuscha | Pink salmon |
| | Oncorhynchus keta | Chum salmon |
| | Oncorhynchus kisutch | Coho salmon |

TABLE 1-continued

Fish that can be fed feedstuffs of the invention.

| Family | Scientific name | Common name |
|---|---|---|
| | Oncorhynchus masou | Masu salmon |
| | Oncorhynchus mykiss | Rainbow trout |
| | Oncorhynchus nerka | Sockeye salmon |
| | Oncorhynchus tshawytscha | Chinook salmon |
| | Salmo salar | Atlantic salmon |
| | Salmo trutta | Sea trout |
| | Salvelinus alpinus | Arctic char |
| | Salvelinus fontinalis | Brook trout |
| | Salvelinus namaycush | Lake trout |
| GADIDAE | Gadus morhua | Atlantic cod |
| ATHERINIDAE | Odontesthes bonariensis | Pejerrey |
| SYNBRANCHIDAE | Monopterus albus | Lai |
| CENTROPOMIDAE | Centropomus undecimalis | Common snook |
| | Lates calcarifer | Barramundi/Asian sea bass |
| | Lates niloticus | Nile perch |
| PERCICHTHYIDAE | Maccullochella peeli | Murray cod |
| | Macquaria ambigua | Golden perch |
| | Morone saxatilis | Striped bass |
| MORONIDAE | Dicentrarchus labrax | European seabass |
| SERRANIDAE | Epinephelus akaara | Hong Kong grouper |
| | Epinephelus areolatus | Areolate grouper |
| | Epinephelus tauvina | Greasy grouper |
| | Plectropomus maculatus | Spotted coralgrouper |
| TERAPONTIDAE | Bidyanus bidyanus | Silver perch |
| CENTRARCHIDAE | Micropterus salmoides | Largemouth black bass |
| PERCIDAE | Perca fluviatilis | European perch |
| | Stizostedion lucioperca | Pike-perch |
| | Perca fluvescens | Yellow Perch |
| | Stizostedion canadense | Sauger |
| | Stizostedion vitreum | Walleye |
| POMATOMIDAE | Pomatomus saltatrix | Bluefish |
| CARANGIDAE | Seriola dumerili | Greater amberjack |
| | Seriola quinqueradiata | Japanese amberjack |
| | Trachinotus blochii | Snubnose pompano |
| | Trachinotus carolinus | Florida pompano |
| | Trachinotus goodei | Palometa pompano |
| | Trachurus japonicus | Japanese jack mackerel |
| RACHYCENTRIDAE | Rachycentron canadum | Cobia |
| LUTJANIDAE | Lutjanus argentimaculatus | Mangrove red snapper |
| | Ocyurus chrysurus | Yellowtail snapper |
| SPARIDAE | Acanthopagrus schlegeli | Dark seabream |
| | Diplodus sargus | White seabream |
| | Evynnis japonica | Crimson seabream |
| | Pagrus major | Red seabream |
| | Pagrus pagrus | Red porgy |
| | Rhandosargus sarba | Goldlined seabream |
| | Sparus aurata | Gilthead seabream |
| SCIAENIDAE | Sciaenops ocellatus | Red drum |
| CICHLIDAE | Aequidens rivulatus | Green terror |
| | Cichlasoma maculicauda | Blackbelt cichlid |
| | Cichlasoma managuense | Jaguar guapote |
| | Cichlasoma urophthalmus | Mexican mojarra |
| | Etroplus suratensis | Pearlspot |
| | Oreochromis andersonii | Three spotted tilapia |
| | Oreochromis aureus | Blue tilapia |
| | Oreochromis macrochir | Longfin tilapia |
| | Oreochromis mossambicus | Mozambique tilapia |
| | Oreochromis niloticus | Nile tilapia |
| | Oreochromis spilurus | Tilapia |
| | Oreochromis urolepis | Wami tilapia |
| | Sarotherodon melanotheron | Blackchin tilapia |
| | Tilapia guineensis | Tilapia |
| | Tilapia rendalli | Redbreast tilapia |
| | Tilapia zillii | Redbelly tilapia |
| MUGILIDAE | Liza aurata | Golden grey mullet |
| | Liza macrolepis | Largescale mullet |
| | Liza parsia | Gold-spot mullet |
| | Liza ramada | Thinlip grey mullet |
| | Liza saliens | Leaping mullet |
| | Liza tade | Tade mullet |
| | Mugil cephalus | Flathead grey mullet |
| | Mugil curema | White mullet |
| | Mugil liza | Lebranche mullet |
| ELEOTRIDAE | Dormitator latifrons | Pacific fat sleeper |
| | Oxyeleotris marmorata | Marble goby |
| SIGANIDAE | Siganus canaliculatus | White-spotted spinefoot |
| | Siganus guttatus | Goldlined spinefoot |
| | Siganus rivulatus | Marbled spinefoot |
| SCOMBRIDAE | Thunnus maccoyii | Southern bluefin tuna |
| | Thunnus thynnus | Northern bluefin tuna |
| ANABANTIDAE | Anabas testudineus | Climbing perch |
| BELONTIIDAE | Trichogaster pectoralis | Snakeskin gourami |
| HELOSTOMATIDAE | Helostoma temmincki | Kissing gourami |
| OSPHRONEMIDAE | Osphronemus goramy | Giant gourami |
| CHANNIDAE | Channa argus | Snakehead |
| | Channa micropeltes | Indonesian snakehead |
| | Channa punctatus | Spotted snakehead |
| | Channa striata | Striped snakehead |
| SCOPHTHALMIDAE | Psetta maxima | Turbot |
| PARALICHTHYIDAE | Paralichthys olivaceus | Bastard halibut (Japanese flounder) |
| | Paralichthys dentatus | Summer Flounder |
| | Paralichthys lethostigma | Southern flounder |
| | Paralichthys americanus | Winter flounder |
| | Hippoglossus hippoglossus | Atlantic Halibut |
| | Rhombosolea tapirina | Greenback flounder |
| SOLEIDAE | Solea vulgaris | Common sole |

\* And all hybrids between any of the above species.

As used herein, the term salmon refers to any species of the Family Salmonidae. Preferably, the salmon is a *Salmo* sp. or *Oncorhynchus* sp. More preferably, the salmon is a *Salmo* sp. Even more preferably, the salmon is Atlantic Salmon (*Salmo salar*).

In an embodiment, the fish, preferably salmon, is at a "larval" or "juvenile" stage. Fish development recognises 5 periods that occur in the following order: embryonic period; larval period; juvenile period; adult period; senescent period. The larval period occurs once the embryo has hatched and has the ability to feed independently of the egg yolk (or mother in rare cases), organ systems develop morphologically and gain physiological function. The juvenile period is when all organ systems are fully formed and functional (bar the gonads) and fish attain the appearance of miniature adults, the period lasts until the gonads become mature. Once the gonads mature the fish attain the adult period, and then senescence when growth ceases and gonads do not produce gametes (Adapted from Moyle, P. B. & Cech, J. J. 2004. Fishes An Introduction to Ichthyology, 5th Edition, Prentice Hall).

The "crustacean" may be any organism of the subphylum "Crustacea", and hence the crustacean may be obtained from marine sources and/or freshwater sources. Such crustacea include, but are not limited to, organisms such as krill, clams, shrimp (including prawns), crab, and lobster. Further examples of crustacea that can be reared on feedstuffs of the invention are provided in Table 2. The invention may be practised with any, all, or any combination of the listed crustacea.

TABLE 2

Crustacea that can be fed feedstuffs of the invention.

| Family | Scientific name | Common name |
|---|---|---|
| PENAEIDAE | Metapenaeus dobsoni | Kadal shrimp |
| | Metapenaeus endeavouri | Endeavour shrimp |
| | Metapenaeus ensis | Greasyback shrimp |
| | Metapenaeus monoceros | Speckled shrimp |
| | Penaeus aztecus | Northern brown shrimp |
| | Penaeus chinensis | Fleshy prawn |
| | Penaeus esculentus | Brown tiger prawn |
| | Penaeus indicus | Indian white prawn |
| | Penaeus japonicus | Kuruma prawn |
| | Penaeus kerathurus | Caramote prawn |
| | Penaeus merguiensis | Banana prawn |
| | Penaeus monodon | Giant tiger prawn |
| | Penaeus notialis | Southern pink shrimp |
| | enaeus paulensis | Sao Paulo shrimp |
| | Penaeus penicillatus | Redtail prawn |
| | Penaeus schmitti | Southern white shrimp |
| | Penaeus semisulcatus | Green tiger prawn |
| | Penaeus setiferus | Northern white shrimp |
| | Penaeus stylirostris | Blue shrimp |
| | Penaeus subtilis | Southern brown shrimp |
| | Penaeus vannamei | Whiteleg shrimp |
| | Xiphopenaeus kroyeri | Atlantic seabob |
| SERGESTIDAE | Acetes japonicus | Akiami paste shrimp |
| PALAEMONIDAE | Macrobrachium malcolmsonii | Monsoon river prawn |
| | Macrobrachium rosenbergii | Giant river prawn |
| | Palaemon serratus | Common prawn |
| NEPHROPIDAE | Homarus americanus | American lobster |
| | Homarus gammarus | European lobster |
| ASTACIDAE | Astacus astacus | Noble crayfish |
| | Astacus leptodactylus | Danube crayfish |
| | Jasus edwardsii | Southern rock lobster |
| | Jasus lalandii | Western rock lobster |
| | Pacifastacus leniusculus | Signal crayfish |
| CAMBARIDAE | Procambarus clarkii | Red swamp crawfish |
| PARASTACIDAE | Cherax destructor | Yabby crayfish |
| | Cherax quadricarinatus | Red claw crayfish |
| | Cherax tenuimanus | Marron crayfish |
| PALINURIDAE | Panulirus longipes | Longlegged spiny lobster |
| PORTUNIDAE | Portunus trituberculatus | Gazami crab |
| | Scylla serrata | Indo-Pacific swamp crab |
| POTAMIDAE | Eriocheir sinensis | Chinese river crab |

* And all hybrids between any of the above species.

Feedstuffs

For purposes of the present invention, "feedstuffs" include any food or preparation, for fish or crustacean consumption.

The present invention provides a feedstuff comprising lipid, the fatty acid of said lipid comprising at least 5.5% (w/w) stearidonic acid (SDA). The invention also provides methods of using said feedstuff for rearing a fish or crustacean.

In embodiments of the invention, the fatty acid of said lipid comprises at least 6%, at least 7%, at least 8%, at least 9%, at least 10%, at least 11.0%, at least 15%, at least 20%, or at least 30% (w/w) SDA.

In further embodiments, the fatty acid of said lipid comprises less than 30%, less than 25%, less than 20%, less than 15%, less than 10%, or more preferably less than 8% (w/w) total saturated fatty acids (SFA). In particular, the feedstuff comprises reduced levels of 14:0 and/or 16:0 compared to the corresponding feedstuff made with fishoil rather than plant oil comprising at least 5.5% SDA.

Although the level of SDA that may be produced in seedoil of transgenic plants may be in excess of 40% of the fatty acid, the invention may be practised with plant oil that has less SDA, such as for example at least 5.5% SDA. That is, not all of the ALA is converted to SDA in the plant, and the oil may contain both SDA and ALA. Therefore, in yet other embodiments, the fatty acid of said lipid comprises at least 10%, at least 15%, at least 16%, at least 17%, at least 18%, or at least 19% (w/w) α-linolenic acid (ALA 18:3Δ9, 12,15, ω3). In an embodiment, the ALA level is in the range 10-45% (w/w).

Preferably, the lipid of the feedstuff comprises phytosterol, which may provide additional benefit. In embodiments of the invention, the lipid comprises at least 0.025%, at least 0.05%, or at least 0.1% (w/w) phytosterol. It may comprise at least 0.2% phytosterol, typically in the range 0.2-0.8% (w/w) phytosterol. The phytosterol may be any plant derived sterol from plants such as, but not limited to, Echium sp., canola, soybean, flax, cereal or grain legume. Examples of phytosterols include, but are not limited to, brassicasterol, campesterol, stigmasterol, β-sitosterol or any combination of these.

In a further embodiment, the lipid is substantially free of cholesterol, which may be advantageous in limiting the cholesterol level in the fish or crustacean that is produced, in particular for fish. As used herein, the term "substantially free of cholesterol" refers to the lipid comprising less than 0.1% (w/w) cholesterol, preferably at an undetectable level. Typically, lipid obtained from plants is substantially free of cholesterol.

In other embodiments, at least 25%, at least 50%, at least 75% or at least 90% of the SDA is esterified in the form of triacylglycerol.

In yet further embodiments, the lipid content of the feedstuff is at least 10, at least 15, at least 20, at least 30, at least 50, at least 100, at least 200, or at least 250 g/kg dry matter. In another embodiment, the lipid content of the feedstuff is no more than 350 g/kg dry matter or any range between these figures.

In other embodiments, the feedstuff comprises at least 0.55, at least 1, at least 2.5, at least 5, at least 7.2, at least 10, at least 12.5, or more preferably at least 14.3 g/kg dry matter of SDA.

In yet another preferred embodiment, the fatty acid of the lipid content of the feedstuff comprises less than 2% EPA and/or DHA, more preferably less than 1% EPA and/or DHA.

The SDA can be from any source. In a preferred embodiment, the SDA is provided in the form of a transgenic organism, or extract or portion thereof, wherein the organism is genetically modified such that it produces SDA and/or produces higher levels of SDA than when compared to a wild-type organism. Preferably, the transgenic organism is a plant or yeast. In a particularly preferred embodiment, the SDA is provided in the form of oil extracted from a plant, especially a transgenic plant. Typically, such oil is extracted from the seed of the plant. However, in some embodiments, the SDA may be obtained from a non-transgenic organism which naturally produces SDA, for example, Echium plantagineum.

Fish and crustaceans can be fed feedstuffs of the present invention in any manner and amount, and according to any feeding schedule employed in fish or crustacean cultivation. Feeding rates typically vary according to abiotic factors, mainly seasonal such as temperature, and biotic, in particular the size of the animal. Juvenile fish are typically fed 5-10% of their body weight per day over about 4-6 feeds per day. Larger fish are typically fed at 2-5% of their body weight per day over about 1-2 feeds per day. Juvenile crustaceans may fed up to 5-10% of their body weight over about 6 feeds per day, while larger crustaceans may be fed a minimum of about 2% of their body weight per day over about 2-3 feeds per day. The fish or crustaceans may be allowed to feed to appetite.

Preferably, the fish or crustaceans are fed at least once per day, more preferably two or more times per day such as, for example, 2-6 or 4-6 times per day. It is preferred that any excess food be removed after the feeding period, e.g., by flushing out of a race-way system, or through removal out of the bottom of the sea-cage. Alternatively, a fish such as catfish can be added to the fish population to consume any excess food.

The benefits increase when fish or crustacean are fed over longer periods of time, for example over at least 6, 7 or 12 weeks. However, it would be appreciated that there is some benefit when the fish or crustacean is provided with the feedstuff over shorter time periods, relative to feeding the fish or crustacean feedstuff containing plant oil not comprising substantial SDA. Feedstuffs other than those described herein may also be used in the time period, however it is preferred that the feedstuff of the invention is used predominantly over the time period if not exclusively.

As used herein, "predominantly" means at least 50% of the time, occasions or in amount, as the context determines.

It is preferable that fish or crustaceans be fed SDA containing feedstuffs as a mixture with other well-known ingredients included in commercial fish or crustaceans food formulations so as to provide a nutritionally balanced complete food, including, but not limited to, plant matter, e.g., flour, meal, starch or cracked or processed grain produced from a crop plant such as wheat or other cereals, alfalfa, corn, oats, potato, rice, soybeans or other legumes; cellulose in a form that may be obtained from wood pulp, grasses, plant leaves, and waste plant matter such as rice or soy bean hulls, or corn cobs; animal matter, e.g., fish or crustacean meal, oil, protein or solubles and extracts, krill, meat meal, bone meal, feather meal, blood meal, or cracklings; algal matter; yeast; bacteria; vitamins, minerals, and amino acids; organic binders or adhesives; and chelating agents and preservatives. A wide variety of formulations are reported in both the patent and scientific literature. Alternatively, SDA is used to supplement other foods, e.g., commercial fish or crustacean foods.

In one embodiment, the feedstuff comprises fishmeal (which may or may not be defatted) but does not comprise, as a separate ingredient, fish oil. Alternatively, the feedstuff may comprise some fishoil as an added separate ingredient. However, the minimum level of SDA in the fatty acid of the total lipid of the feedstuff should remain at least 5.5%.

On a commercial scale feedstuffs may conveniently be provided in the form of pressed or extruded feed pellets.

The components utilized in the feedstuff compositions of the present invention can be of semi-purified or purified origin. By semi-purified or purified is meant a material which has been prepared by purification of a natural material or by de novo synthesis.

With respect to vitamins and minerals, the following may be added to the feedstuff compositions of the present invention: calcium, phosphorus, potassium, sodium, chloride, magnesium, manganese, iron, copper, zinc, selenium, iodine, and Vitamins A, E, D, C, and the B complex. Examples of these include Stay C which is a commercial stabilised vitamin C product, trisodium phosphate or Banox E which is an antioxidant. Other such vitamins and minerals may also be added.

Desaturases

Organisms useful for producing feedstuffs of the invention typically comprise a gene encoding a Δ6 desaturase, which may be a transgene or an endogenous gene. As used herein, a "Δ6 desaturase" is at least capable of converting ALA to SDA, and/or linoleic acid (LA, 18:2Δ9,12, ω6) to γ-linolenic acid (GLA, 18:2Δ6,9,12, ω6). Examples of suitable Δ6 desaturases include, but are not limited to, those which comprises (i) an amino acid sequence as provided as SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11 or SEQ ID NO:12, (ii) an amino acid sequence which is at least 50% identical to any one of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11 or SEQ ID NO:12, or (iii) a biologically active fragment of i) or ii). In a further embodiment, the Δ6 desaturase comprises an amino acid sequence which is at least 90% identical to any one of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11 or SEQ ID NO:12. In a further embodiment, the Δ6 desaturase is encoded by the protein coding region of one of the Δ6 desaturase genes listed in Table 3 or gene at least 75% identical thereto.

The Δ6 desaturase may also have other activities such as Δ5 desaturase activity. Such enzymes are known in the art as a "Δ5/Δ6 bifunctional desaturase" or a "Δ5/Δ6 desaturase". These enzymes are at least capable of i) converting ALA to SDA, and ii) converting eicosatetraenoic acid to eicosapentaenoic acid. A gene encoding a bifunctional Δ5-/Δ6-desaturase has been identified from zebrafish (Hasting et al., 2001). The gene encoding this enzyme might represent an ancestral form of the "front-end desaturase" which later duplicated and the copies evolved distinct Δ5- and Δ6-desaturase functions. In one embodiment, the Δ5/Δ6 bifunctional desaturase is naturally produced by a freshwater species of fish. In a particular embodiment, the Δ5/Δ6 bifunctional desaturase comprises i) an amino acid sequence as provided in SEQ ID NO:13,
ii) an amino acid sequence which is at least 50% identical to SEQ ID NO:13, or
iii) a biologically active fragment of i) or ii).

TABLE 3

Examples of Δ6 desaturases from different sources.

| Type of organism | Species | Accession Nos. | Protein size (aa's) | References |
|---|---|---|---|---|
| Mammals | Homo sapiens | NM_013402 | 444 | Cho et al., 1999; Leonard et al., 2000 |
| | Mus musculus | NM_019699 | 444 | Cho et al., 1999 |
| Nematode | Caenorhabditis elegans | Z70271 | 443 | Napier et al., 1998 |
| Plants | Borago officinales | U79010 | 448 | Sayanova et al., 1997 |
| | Echium | AY055117 AY055118 | | Garcia-Maroto et al., 2002 |
| | Primula vialii | AY234127 | 453 | Sayanova et al., 2003 |

TABLE 3-continued

Examples of Δ6 desaturases from different sources.

| Type of organism | Species | Accession Nos. | Protein size (aa's) | References |
|---|---|---|---|---|
| | Anemone leveillei | AF536525 | 446 | Whitney et al., 2003 |
| Mosses | Ceratodon purpureus | AJ250735 | 520 | Sperling et al., 2000 |
| | Marchantia polymorpha | AY583463 | 481 | Kajikawa et al., 2004 |
| | Physcomitrella patens | | | Girke et al., 1998 |
| Fungi | Mortierella alpina | AF110510 AB020032 | 457 | Huang et al., 1999; Sakuradani et al., 1999 |
| | Pythium irregulare | AF419296 | 459 | Hong et al., 2002 |
| | Mucor circinelloides | AB052086 | 467 | |
| | Rhizopus sp. | AY320288 | 458 | Zhang et al., 2004 |
| | Saprolegnia diclina | | 453 | WO02081668 |
| Diatom | Phaeodactylum tricornutum | AY082393 | 477 | Domergue et al., 2002 |
| Bacteria | Synechocystis | L11421 | 359 | Reddy et al., 1993 |
| Algae | Thraustochytrium aureum | | 456 | WO02081668 |
| Fish | Danio rerio | AF309556 | 444 | Hastings et al., 2001 |

Organisms useful in producing feedstuffs of the invention generally comprise a gene encoding an "ω3 desaturase", which may be a transgene or an endogenous gene. As used herein, an "ω3 desaturase" is at least capable of converting LA to ALA and/or GLA to SDA and are therefore able to introduce a desaturation at the third carbon-carbon bond from the ω end of the acyl substrate. Such desaturases may also be known in the art as Δ15 desaturases when active on a C18 substrate, for example 18:2 (LA), introducing a desaturation at the fifteenth carbon-carbon bond from the carboxy (Δ) end of the acyl chain. Examples of ω3 desaturase include those described by Pereira et al. (2004), Horiguchi et al. (1998), Berberich et al. (1998) and Spychalla et al. (1997) or as listed in Table 4. Examples of suitable Δ15 desaturases include, but are not limited to, those which comprise (i) an amino acid sequence as provided in SEQ ID NO:26, SEQ ID NO:27, SEQ ID NO:28 or SEQ ID NO:29, (ii) an amino acid sequence which is at least 50% identical to any one of SEQ ID NO:26, SEQ ID NO:27, SEQ ID NO:28 or SEQ ID NO:29, or (iii) a biologically active fragment of i) or ii). In a further embodiment, the Δ15 desaturase comprises an amino acid sequence which is at least 90% identical to any one of SEQ ID NO:26, SEQ ID NO:27, SEQ ID NO:28 or SEQ ID NO:29. In a further embodiment, the Δ15 desaturase has an amino acid sequence according to an Accession No listed in Table 4, or is encoded by the protein coding region of one of the Δ15 desaturase genes listed in Table 4, or a protein or gene at least 75% identical thereto.

TABLE 4

Examples of ω3/Δ15 desaturases.

| Type of organism | Species | Accession Nos. | Protein size | References |
|---|---|---|---|---|
| Plant | Arabidopsis thaliana | NP_850139.1 | 288 | NCBI |
| | | AY096462. | 386 | NCBI |
| | | AAL77744 | 435 | NCBI |
| | Brassica napus | P48642 | 383 | Arondel et al., 1992 |
| | | AY599884 | 383 | NCBI |
| | | JQ2337 | 377 | NCBI |
| | | AAT65204 | 378 | NCBI |
| | Brassica rapa subsp. oleifera | AAL08867 | 302 | Tanhuanpaa et al., 2002 |
| | Glycine max | BAB18135 | 380 | NCBI |
| | | AAO24263 | 376 | Bilyeu et al., 2003 |
| | | P48621 | 453 | Yadav et al., 1993 |
| | Linum usitatissimum | ABA02173 | 391 | Vrinten et al., 2005 |
| | | ABA02172 | 392 | Vrinten et al., 2005 |
| | Betula pendula | AAN17504 | 386 | NCBI |
| | Perilla frutescens | AAD15744 | 391 | Chung et al., 1999 |
| | | AAL36934 | 390 | NCBI |
| | | AAB39387 | 438 | NCBI |
| | Pelargonium x hortorum | AAC16443 | 407 | NCBI |
| | Malus x domestica | AAS59833 | 439 | NCBI |
| | Vernicia fordii | CAB45155 | 387 | NCBI |
| | | AAD13527 | 437 | Tang et al., 1999 |
| | Vigna radiata | P32291 | 380 | Yamamoto et al., 1992 |
| | Prunus persica | AAM77643 | 449 | NCBI |
| | Brassica juncea | CAB85467 | 429 | NCBI |
| | Nicotiana tabacum | P48626 | 379 | Hamada et al., 1994 |
| | | BAA11475 | 441 | Hamada et al., 1996 |
| | Betula pendula | AAN17503 | 444 | NCBI |
| | Zea mays | BAA22442 | 398 | Berberich et al., 1998 |
| | | BAA22441 | 443 | Berberich et al., 1998 |
| | Petroselinum crispum | AAB72241 | 438 | Kirsch et al., 1997 |
| | Sesamum indicum | P48620 | 447 | NCBI |
| | Helianthus annuus | AAP78965 | 443 | NCBI |
| | Capsicum annuum | AAF27933 | 438 | NCBI |
| | Ricinus communis | P48619 | 460 | VandeLoo et al., 1994 |
| | Sorghum bicolor | AAT72937 | 389 | Yang et al., 2004 |
| | Oryza sativa | XP_479619 | 387 | NCBI |
| | Solanum tuberosum | CAA07638 | 431 | NCBI |
| | Solanum lycopersicum | AAP82169 | 435 | Li et al., 2003 |
| | Triticum aestivum | BAA28358 | 383 | Horiguchi et al., 1998 |
| Algae | Chlorella vulgaris | BAB78717 | 418 | Suga et al., 2002 |
| | Synechococcus sp | AAB61352 | 350 | Sakamoto et al., 1997 |
| | Dunaliella salina | AAD48897 | 196 | NCBI |
| Fungi | Saprolegnia diclina | AAR20444 | 358 | Pereira et al., 2004 |

NCBI indicates sequences are available from http://www.ncbi.nlm.nih.gov/

The % identity of a polypeptide is determined by GAP (Needleman and Wunsch, 1970) analysis (GCG program) with a gap creation penalty=5, and a gap extension penalty=0.3. Unless stated otherwise, the query sequence is at least 15 amino acids in length, and the GAP analysis aligns the two sequences over a region of at least 15 amino acids.

More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence and a sequence defined herein are aligned over their entire length.

The term "polypeptide" is used interchangeably herein with the terms "protein" and "enzyme".

With regard to the defined polypeptides/enzymes, it will be appreciated that % identity figures higher than those provided above will encompass preferred embodiments. Thus, where applicable, in light of the minimum % identity figures, it is preferred that the polypeptide comprises an amino acid sequence which is at least 60%, more preferably at least 65%, more preferably at least 70%, more preferably at least 75%, more preferably at least 76%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

As used herein, the term "biologically active fragment" refers to a portion of the defined polypeptide/enzyme which still maintains desaturase activity. Such biologically active fragments can readily be determined by serial deletions of the full length protein, and testing the activity of the resulting fragment.

Cells

Suitable cells for use in feedstuffs of the invention, or which can be used to produce SDA for feedstuffs of the invention, include any cell containing SDA or that can be transformed with a polynucleotide encoding a polypeptide/enzyme described herein, and which is thereby capable of being used for producing SDA. Host cells into which the polynucleotide(s) are introduced can be either untransformed cells or cells that are already transformed with at least one nucleic acid molecule. Such nucleic acid molecule may be related to SDA synthesis, or unrelated. Host cells either can be endogenously (i.e., naturally) capable of producing proteins described herein or can be capable of producing such proteins only after being transformed with at least one nucleic acid molecule.

The cells may be prokaryotic or eukaryotic. Host cells can be any cell capable of producing SDA, and include fungal (including yeast), parasite, arthropod, animal and plant cells. Preferred host cells are yeast and plant cells. In a preferred embodiment, the plant cells are seed cells.

In one embodiment, the cell is an animal cell or an algal cell. The animal cell may be of any type of animal such as, for example, a non-human animal cell, a non-human vertebrate cell, a non-human mammalian cell, or cells of aquatic animals such as fish or crustacea, invertebrates, insects, etc.

The cells may be of an organism suitable for fermentation. Suitable fermenting cells, typically microorganisms are able to ferment, i.e., convert, sugars, such as glucose or maltose, directly or indirectly into the desired fermentation product. Examples of fermenting microorganisms include fungal organisms, such as yeast. As used herein, "yeast" includes *Saccharomyces* spp., *Saccharomyces cerevisiae*, *Saccharomyces carlbergensis*, *Candida* spp., *Kluveromyces* spp., *Pichia* spp., *Hansenula* spp., *Trichoderma* spp., *Lipomyces starkey*, and *Yarrowia lipolytica*.

Gene Constructs and Vectors

Transgenic organisms, and/or host cells, producing SDA are typically transformed with a recombinant vector. The vector can be either RNA or DNA, either prokaryotic or eukaryotic, and typically is a virus or a plasmid.

One type of recombinant vector comprises a nucleic acid molecule which encodes an enzyme useful for the purposes of the invention (such as a polynucleotide encoding a Δ6 desaturase or ω3 desaturase) operatively linked to an expression vector. As indicated above, the phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and effecting expression of a desired nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells, including in bacterial, fungal, endoparasite, arthropod, other animal, and plant cells. Preferred expression vectors of the present invention can direct gene expression in yeast, animal or plant cells.

In particular, expression vectors contain regulatory sequences such as transcription control sequences, translation control sequences, origins of replication, and other regulatory sequences that are compatible with the recombinant cell and that control the expression of desired nucleic acid molecules. In particular, recombinant molecules include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells. A variety of such transcription control sequences are known to those skilled in the art.

Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules can remain extrachromosomal or can integrate into one or more sites within a chromosome of the transformed (i.e., recombinant) cell in such a manner that their ability to be expressed is retained.

Transgenic Plants and Parts Thereof

The term "plant" as used herein as a noun refers to whole plants, but as used as an adjective refers to any substance which is present in, obtained from, derived from, or related to a plant, such as for example, plant organs (e.g. leaves, stems, roots, flowers), single cells (e.g. pollen), seeds, plant cells and the like. Plants provided by or contemplated for use in the practice of the present invention include both monocotyledons and dicotyledons. In preferred embodiments, plant useful for the production of feedstuffs of the present invention are crop plants (for example, cereals and pulses, maize, wheat, potatoes, tapioca, rice, sorghum, millet, cassava, barley, or pea), or other legumes. The plants may be grown for production of edible roots, tubers, leaves, stems, flowers or fruit. The plants of the invention may be: corn (*Zea mays*), canola (*Brassica napus, Brassica rapa* ssp.), flax (*Linum usitatissimum*), rice (*Oryza sativa*), rye (*Secale cerale*), sorghum (*Sorghum bicolour, Sorghum vulgare*), sunflower (*Helianthus annus*), wheat (*Tritium aestivum*), soybean (*Glycine max*), peanuts (*Arachis hypogaea*), cotton (*Gossypium hirsutum*), cassava (*Manihot esculenta*), coconut (*Cocos nucifera*), olive (*Olea europaea*), oats, or barley.

In one embodiment, the plant is an oilseed plant, preferably an oilseed crop plant. As used herein, an "oilseed plant" is a plant species used for the commercial production of oils from the seeds of the plant. The oilseed plant may be oil-seed rape (such as canola), maize, sunflower, soybean, sorghum, oil palm or flax (linseed). Furthermore, the oilseed plant may be other *Brassicas*, cotton, peanut, poppy, mustard, castor bean, sesame, safflower, or nut producing plants. The plant may produce high levels of oil in its fruit, such as olive or coconut.

Examples of cotton of the, and/or useful for, the present invention include any species of *Gossypium*, including, but not limited to, *Gossypium arboreum, Gossypium herbaceum, Gossypium barbadense* and *Gossypium hirsutum*.

When the production of SDA is desired it is preferable that the plant species which is to be transformed has an endogenous ratio of ALA to LA which is at least 1:1, more preferably at least 2:1. Examples include most, if not all, oilseeds such as linseed. This maximizes the amount of ALA substrate available for the production of SDA. This may be achieved by transgenic means; for example by introduction of a Δ15 deaturase gene into the plant to increase the levels of the ALA substrate for conversion into SDA.

The plants produced for use in feedstuffs of the invention may already be transgenic, and/or transformed with additional genes to those described in detail herein.

Grain plants that provide seeds of interest include oil-seed plants and leguminous plants. Seeds of interest include grain seeds, such as corn, wheat, barley, rice, sorghum, rye, etc. Leguminous plants include beans, peas, soybeans, lupins and the like. Beans include guar, locust bean, fenugreek, garden beans, cowpea, mungbean, lima bean, fava bean, lentils, chickpea, etc.

The term "extract or portion thereof" refers to any part of the plant. "Portion" generally refers to a specific tissue or organ such as a seed or root, whereas an "extract" typically involves the disruption of cell walls and possibly the partial purification of the resulting material. Naturally, the "extract or portion thereof" will comprise SDA. Extracts can be prepared using standard techniques of the art.

Transgenic plants, as defined in the context of the present invention include plants and their progeny which have been genetically modified using recombinant techniques. This would generally be to cause or enhance production of at least one protein/enzyme defined herein in the desired plant or plant organ. Transgenic plant parts include all parts and cells of said plants such as, for example, cultured tissues, callus, protoplasts. Transformed plants contain genetic material that they did not contain prior to the transformation. The genetic material is preferably stably integrated into the genome of the plant. Such plants are included herein in "transgenic plants". A "non-transgenic plant" is one which has not been genetically modified with the introduction of genetic material by recombinant DNA techniques. In a preferred embodiment, the transgenic plants are homozygous for each and every gene that has been introduced (transgene) so that their progeny do not segregate for the desired phenotype.

Several techniques exist for introducing foreign genetic material into a plant cell. Such techniques include acceleration of genetic material coated onto microparticles directly into cells (see, for example, U.S. Pat. Nos. 4,945,050 and 5,141,131). Plants may be transformed using *Agrobacterium* technology (see, for example, U.S. Pat. Nos. 5,177,010, 5,104,310, 5,004,863, 5,159,135). Electroporation technology has also been used to transform plants (see, for example, WO 87/06614, U.S. Pat. Nos. 5,472,869, 5,384,253, WO 92/09696 and WO 93/21335). In addition to numerous technologies for transforming plants, the type of tissue which is contacted with the foreign genes may vary as well. Such tissue would include but would not be limited to embryogenic tissue, callus tissue type I and II, hypocotyl, meristem, and the like. Almost all plant tissues may be transformed during development and/or differentiation using appropriate techniques known to those skilled in the art.

A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Gelvin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Examples of plant promoters include, but are not limited to ribulose-1,6-bisphosphate carboxylase small subunit, beta-conglycinin promoter, phaseolin promoter, high molecular weight glutenin (HMW-GS) promoters, starch biosynthetic gene promoters, ADH promoter, heat-shock promoters and tissue specific promoters. Promoters may also contain certain enhancer sequence elements that may improve the transcription efficiency. Typical enhancers include but are not limited to Adh-intron 1 and Adh-intron 6.

Constitutive promoters direct continuous gene expression in all cells types and at all times (e.g., actin, ubiquitin, CaMV 35S). Tissue specific promoters are responsible for gene expression in specific cell or tissue types, such as the leaves or seeds (e.g., zein, oleosin, napin, ACP, globulin and the like) and these promoters may also be used.

In a particularly preferred embodiment, the promoter directs expression in tissues and organs in which lipid and oil biosynthesis take place, particularly in seed cells such as endosperm cells and cells of the developing embryo. Promoters which are suitable are the oilseed rape napin gene promoter (U.S. Pat. No. 5,608,152), the *Vicia faba* USP promoter (Baumlein et al., 1991), the *Arabidopsis* oleosin promoter (WO 98/45461), the *Phaseolus vulgaris* phaseolin promoter (U.S. Pat. No. 5,504,200), the *Brassica* Bce4 promoter (WO 91/13980), the linin gene promoter from flax, or the legumin B4 promoter (Baumlein et al., 1992), and promoters which lead to the seed-specific expression in monocots such as maize, barley, wheat, rye, rice and the like. Notable promoters which are suitable are the barley lpt2 or lpt1 gene promoter (WO 95/15389 and WO 95/23230) or the promoters described in WO 99/16890 (promoters from the barley hordein gene, the rice glutelin gene, the rice oryzin gene, the rice prolamin gene, the wheat gliadin gene, the wheat glutelin gene, the maize zein gene, the oat glutelin gene, the sorghum kasirin gene, the rye secalin gene). Other promoters include those described by Broun et al. (1998) and US 20030159173.

Under certain circumstances it may be desirable to use an inducible promoter. An inducible promoter is responsible for expression of genes in response to a specific signal, such as: physical stimulus (heat shock genes); light (RUBP carboxylase); hormone (Em); metabolites; and stress. Other desirable transcription and translation elements that function in plants may be used.

In addition to plant promoters, promoters from a variety of sources can be used efficiently in plant cells to express foreign genes. For example, promoters of bacterial origin, such as the octopine synthase promoter, the nopaline synthase promoter, the mannopine synthase promoter; promoters of viral origin, such as the cauliflower mosaic virus (35S and 19S) and the like may be used.

EXAMPLES

Example 1. Materials and Methods

Lipid Extraction and Isolation

Samples were freeze dried and extracted using a modified Bligh and Dyer protocol (Bligh and Dyer, 1959). A single phase extraction, $CHCl_3/MeOH/H_2O$, (1:1:0.9, by vol), was used to yield a total lipid extract (TLE).

Lipid classes were analysed by an Iatroscan MK V thin-layer chromatography-flame ionization detector (TLC-FID) analyser (Iatron Laboratories, Japan). Samples were spotted onto silica gel SITE Chromarods (5 µm particles size) and developed in a glass tank lined with pre-extracted filter paper. The solvent system used for the lipid separation was hexane: diethyl ether: acetic acid (60:17:0.1, v/v/v) (Volkman and Nichols, 1991). After development for 25 minutes, the chromarods were oven-dried and analysed immediately to minimise adsorption of atmospheric contaminants. Lipid classes were quantified by DAPA software (Kalamunda, Wash., Australia). The FID was calibrated for each compound class: phosphatidylcholine; cholesterol; cholesteryl ester; oleic acid; hydrocarbon (squalene); wax ester (derived from fish oil); triacylglycerol (derived from fish oil); and DAGE (purified from shark liver oil).

An aliquot of the TLE was trans-methylated in methanol: chloroform:hydrochloric acid (10:1:1, v/v/v) for 1 hour at 100° C. After addition of water the mixture was extracted three times with hexane: chloroform (4:1, v/v) to produce fatty acid methyl esters (FAME). FAME were concentrated under nitrogen and treated with N,O-bis(trimethylsilyl)-trifloroacetamide (BSFTA, 50 µl, 60° C., 1 h) to convert hydroxyl groups to their corresponding trimethylsilyl ethers. Samples were made up to a known volume with an internal injection standard (23:0 or 19:0 FAME) and analysed by gas chromatography (GC) using an Agilent Technologies 6890N GC (Palo Alto, Calif., USA) equipped with an HP-5 cross-linked methyl silicone fused silica capillary column (50 m×0.32 mm i.d.), and an FID. Helium was used as the carrier gas. Samples were injected, by a split/splitless injector and an Agilent Technologies 7683 Series auto sampler in split-less mode, at an oven temperature of 50° C. After 1 min the oven temperature was raised to 150° C. at 30° C. $min^{-1}$, then to 250° C. at 2° C. per min and finally to 300° C. at 5° C. min. Peaks were quantified by Agilent Technologies GC ChemStation software (Palo Alto, Calif., USA). Individual components were identified by mass spectral data and by comparing retention time data with those obtained for authentic and laboratory standards. GC results are typically subject to an error of ±5% of individual component area. GC-mass spectrometric (GC-MS) analyses were performed on a Finnigan Thermoquest GCQ GC-mass spectrometer fitted with an on-column injector with Thermoquest Xcalibur software (Austin, Tex., USA). The GC was fitted with a capillary column similar to that described above.

A polar column was used to separate 18:1ω9 and 18:3ω3 which coeluted on the HP5 column. FAME were analysed with a Hewlett Packard 5890 gas chromatograph (GC) equipped with a flame ionisation detector (FID) at 250° C. FAME samples were injected using a split/splitless injector into a polar BPX-70 fused-silica column (50 m×0.32 mm i.d.). The carrier gas was helium. The GC oven temperature was initially held at 45° C. for 2 min after injection and then increased at 30° C./min to 120° C. and at 3° C./min to 240° C., then held isothermal for 10 min.

Statistical Analysis

Mean values were reported plus or minus standard error of the mean. Percentage data were arcsin transformed prior to analysis. Normality and homogeneity of variance were confirmed and a comparison between means was achieved by 1-way analysis of variance (ANOVA). Multiple comparisons were achieved by Turkey-Kramer HSD. Significance was accepted as probabilities of 0.05 or less. Statistical analysis was performed using SPSS for windows version 11.

*Brassica* Transformation

*Brassica napus* (Line BLN 1239) seeds were surface sterilized by soaking them in 70% (v/v) ethanol for 2 min and then rinsed for 10 min in tap water at 55° C. The seeds were sterilized for 20 min in 25% commercial bleach (10 $gl^{-1}$ sodium hypochlorite) containing 0.1% Tween-20. The seeds were washed thoroughly with sterile distilled $H_2O$, placed on GEM medium in tissue culture jars and kept in the cold room for two days for germination. The jars were transferred to low light (20 $\mu Mm^2 s^{-1}$) for about four to six days at 24° C. for growth of the cotyledons. Roots and apices were removed under aseptic conditions. Excised hypocotyl segments (10 mm) were washed with 50 ml CIM medium for about 30 min without agitation in the laminar flow cabinet. The CIM was removed and the segments transferred to a 250 ml flask with 50 ml of CIM, sealed with sterile aluminium foil and shaken for 48 hours at 24° C. under low light (10 $\mu Mm^2 s^{-1}$).

*Agrobacterium* strains containing plasmid transformation vectors were grown in 5 ml of LB media with appropriate antibiotics at 28° C. for about two days, transferred to a 250 ml Erlenmeyer flask with 45 ml of LB without antibiotics and cultured for four hours at 28° C. with shaking. The *Agrobacterium* cells were pelleted by centrifugation, washed, and gently re-suspended in about 20 ml BM. The optical density at 600 nm of the resultant *Agrobacterium* suspension was adjusted to 0.2 with BM. The cell suspension was added to the explants which had been drained of the CIM medium, mixed briefly and allowed to stand for 20 min. The *Agrobacterium* suspension was removed, the hypocotyl explants washed once with 50 ml CIM and co-cultivation continued for 48 hours on an orbital shaker. After this, the medium was slightly milky due to *Agrobacterium* growth. CIM was removed and the explants washed three times with 50 ml CIM for one minute and then twice for one hour on an orbital shaker at 140×g. Following the washes, 50 ml CIM containing 200 mg/l Timentin® was added and placed on an orbital shaker for 24 hours. Under sterile conditions, the CIM medium was clear at this stage.

Regeneration of transformed shoots on SIM was carried out on a two-stage selection process. Initially, the hygromycin concentration in the SIM medium used was 5 mg/l. After about two weeks, explants with developing calli were transferred to SIM containing 20 mg/l hygromycin. When the regenerating shoots had developed leaves longer than one cm, they were excised carefully and were transferred to SEM with 20 mg/l hygromycin. After two weeks, stems usually had elongated and apices were transferred to RIM containing 10 mg/l hygromycin. Non-elongating shoots were sub-cultured in SEM every two to three weeks until they were long enough to be transferred to RIM. When the roots were about two cm in length, the regenerated plantlets were removed from tissue culture pots and transferred to soil for further growth.

Media Recipes

Composition of the tissue culture media used in this procedure is given below. They contained MS salts (Murashige and Skoog, 1962), MS or B5 vitamins (Gamborg et al., 1968), sucrose and MES. The pH was adjusted to 5.8 with KOH prior to sterilization. For solid media, agar was added and then autoclaved. Media containing agar was allowed to cool to below 50° C. and filter-sterilized compounds were added to the melted media before pouring it into either plastic Petri dishes or 250 ml polycarbonate tissue culture jars (Sarstedt, No 75.9922519). The composition of various media with all additives are given below: germination medium (GEM); basal medium (BM); callus-inducing medium (CIM, modified from Radke et al., 1988); washing medium (WM); shoot-inducing medium (SIM, modified from Radke et al., 1988); shoot-elongation medium (SEM) and root-inducing medium (RIM, modified from De Block et al., 1989).

GEM: 1×MS salts, 1×MS vitamins, Sucrose (20 $gl^{-1}$), MES (500 $mgl^{-1}$), Agar (8 $gl^{-1}$), pH to 5.8.

BM: 1×MS salts, 1×B5 vitamins, Sucrose (30 $gl^{-1}$), MES (500 $mgl^{-1}$), pH to 5.8.

CIM: 2,4-D (1.0 $mgl^{-1}$) and Kinetin (1.0 $mgl^{-1}$) added to BM.

WM 2,4-D (1.0 $mgl^{-1}$), Kinetin (1.0 $mgl^{-1}$) and Timentin® (200 $mgl^{-1}$) added to BM.

SIM: $AgNO_3$ (500 $mgl^{-1}$), Zeatin riboside (0.5 $mgl^{-1}$), BAP (2.0 $mgl^{-1}$), $GA_3$ (0.01 $mgl^{-1}$), Timentin® (200 $mgl^{-1}$), Hygromycin (5 to 30 $mgl^{-1}$), and Agar (8 $gl^{-1}$) added to BM.

SEM: 0.5×MS salts, 0.5×B5 vitamins, Sucrose (10 $gl^{-1}$), MES (500 $mgl^{-1}$), Timentin® (200 $mgl^{-1}$), Hygromycin (20 to 30 $mgl^{-1}$), Agar (8 $gl^{-1}$), pH to 5.8.

RIM: 0.5×MS salts, 0.5×B5 vitamins, Sucrose (10 $gl^{-1}$), MES (500 $mgl^{-1}$), IBA (0.1 $mgl^{-1}$), Timentin® (200 $mgl^{-1}$), Hygromycin (20 to 30 $mgl^{-1}$), Agar (8 $gl^{-1}$), pH to 5.8.

Example 2. Fish Fed with Food Compositions Including Plant-Derived SDA

Stearidonic acid (SDA, 18:4 ω3) is an LC-PUFA precursor, derived by desaturation of ALA by Δ6 desaturase (FIG. 1). The Δ6 desaturase is also involved other steps in the biosynthesis of LC-PUFA in the formation of DHA from EPA in vertebrates (Yamazaki et al., 1992) and 18:2 ω6 to 20:4 ω6. Therefore it is possible that the Δ6 desaturation of ALA is out-competed by the ω6 pathway in fish and crustacea when diets contain high levels of 18:2 ω6, present in vegetable oils such as canola and sunflower.

Oil from a few plant sources such as *Echium plantagineum* have SDA in the fatty acid profile, up to about 15-20% as a percentage of the fatty acid in the oil. To determine whether SDA-rich oil might serve as an efficient substrate for ω3 LC-PUFA accumulation in fish, a feeding trial was conducted in vivo using salmon (*Salmo salar* L.). Diets including an equivalent level of canola oil were used as a control source of ALA, as described in Tables 5 and 6.

TABLE 5

Ingredient and lipid composition (g/kg dry matter) of experimental diets.

| | Diet | | | |
|---|---|---|---|---|
| | CO oil (g) | SO oil (g) | Mix oil (g) | FO oil (g) |
| Ingredient composition (g $kg^{-1}$) | | | | |
| Fishmeal (defatted) | 150 | 150 | 150 | 150 |
| Casein | 150 | 150 | 150 | 150 |
| Wheat Gluten | 100 | 100 | 100 | 100 |
| Hipro soy | 226 | 226 | 226 | 226 |
| Fish oil | 0 | 0 | 0 | 130 |
| Canola oil | 130 | 0 | 65 | 0 |
| SDA oil | 0 | 130 | 65 | 0 |
| Pre Gel Starch | 150 | 150 | 150 | 150 |
| Vitamin Mix[a] | 3 | 3 | 3 | 3 |
| Mineral Mix[b] | 5 | 5 | 5 | 5 |
| Stay C[c] | 3 | 3 | 3 | 3 |
| Choline chloride | 2 | 2 | 2 | 2 |
| Bentontie | 50 | 50 | 50 | 50 |
| CMC | 10 | 10 | 10 | 10 |
| Sodium Mono P | 20 | 20 | 20 | 20 |
| Yttrium Oxide | 10 | 10 | 10 | 10 |
| FAME | | | | |
| Total SFA | 6.7 | 10.8 | 12.2 | 44.9 |
| Total MUFA | 81.2 | 41.3 | 56.2 | 32.9 |
| 18:3ω3 ALA | 13.1 | 25.4 | 20.9 | 3.1 |
| 18:4ω3 SDA | 0.0 | 14.3 | 7.2 | 4.2 |
| 20:5ω3 EPA | 0.1 | 0.1 | 0.0 | 18.0 |
| 22:6ω3 DHA | 0.6 | 0.4 | 0.0 | 10.7 |
| Total ω3 | 13.9 | 40.2 | 28.6 | 39.6 |
| 18:2ω6 | 28.2 | 25.8 | 27.0 | 8.0 |
| Total ω6 | 28.2 | 26.1 | 27.0 | 9.3 |
| Other PUFA | 0.0 | 11.6 | 5.9 | 3.3 |
| Total PUFA | 42.1 | 77.9 | 61.5 | 52.2 |

SO, stearidonic rich oil crossential SA14 from Croda chemicals;

CO, canola oil diet;

Mix, 1:1 mix diet of canola oil and stearidonic acid oil;

FO, fish oil diet,

SFA, Saturated fatty acids;

MUFA, monounsaturated fatty acids;

PUFA, polyunsaturated fatty acids;

CMC, Carboxymethyl cellulose;

DHA, Docosahexaenoic Acid;

EPA, SDA, Stearidonic acid; Eicosapentaenoic Acid.

[a]Vitamin mix (ASV4) to supply per kilogram feed: 2.81 mg thiamin HCL, 1.0 mg riboflavin, 9.15 mg pyridoxine HCL, 25 mg nicotinic acid, 54.35 mg calcium D-pantothenate, 750 mg myo-inositol, 0.38 mg D-biotin, 2.5 mg folic acid, 0.03 mg cyanocobalamin, 6350 IU retinol acetate, 2800 IU cholecalciferol, 100 IU DL ☐-tocopherol acetate, 5 mg menadone sodium bisulphate, 100 mg Roche rovimix E50.

[b]Mineral mix (TMV4) to supply per kilogram feed: 117 mg $CuSO_4 \cdot 5H_2O$, 7.19 mg KI, 1815 mg $FeSO_4 \cdot 7H_2O$, 307 mg $MnSO_4 \cdot H_2O$, 659 mg $ZnSO_4 \cdot 7H_2O$, 3.29 mg $Na_2SeO_3$, 47.7 mg $CoSO_4 \cdot 7H_2O$

[c]L-Ascorbyl-2-polyphosphate (Stay-C, Roche Vitamins Australia, French Forest, NSW, Australia).

Four diets were formulated to compare canola oil (CO), two different levels of stearidonic acid oil (100% (SO), 1:1 SO:CO (Mix)), and fish oil (FO) (Tables 5 and 6). Fish meal was defattened three times using a 2:1 mixture of hexane and ethanol (400 ml 100 g$^{-1}$ fish meal). Soybean (Hamlet Protein A/S, Horsens, Denmark), casein (MP Biomedcals Australasia Pty Ltd, Seven Hills NSW, Australia), wheat gluten (Starch Australasia, Land Cove, NSW, Australia) and BOIIC pre-gelatinised maize starch (Penford Australia Limited, Lane Cove, NSW, Australia) were used. Stearidonic acid rich oil was provided as Crossential SΔ14 (Croda Chemicals, East Yorkshire, UK). Fish oil was from jack mackerel (Skretting Australia, Cambridge, Tasmania Australia). Stay-C and Rovimix E50 were supplied from Roche Vitamins Australia (Frenchs Forest, NSW, Australia), and the remaining ingredients were supplied by Sigma-Aldrich (Castle Hill, NSW, Australia). Yttrium Oxide was used as a digestibility marker. The diets were manufactured into 3 mm diameter pellets using a California Pellet Mill (CL-2), dried and stored at −5° C.

The feeding experiment was conducted at the School of Aquaculture, University of Tasmania, Launceston, Australia. Atlantic salmon (*Salmo salar*) parr were obtained from Wayatinah Salmon hatchery (SALTAS, Tasmania, Australia) and randomly stocked into 300 l tanks at 25 fish per tank. They were acclimated for 10 days. The tanks were held at a constant temperature of 15.0° C. and a photoperiod of 16:8 (light:dark). The fish were held in a partial freshwater recirculation system. Water was treated through physical, UV and biofilters, with a continuous replacement of approximately 15% per day. Dissolved oxygen, pH, ammonia, nitrate, nitrite, and chlorine were monitored daily to ensure water quality remained within parameters recommended for Atlantic salmon (Wedemeyer, 1996).

TABLE 6

Fatty acid composition of the lipid in the diets (% of total fatty acid).

| FA | CO | SE | SO | SE | Mix | SE | FO | SE |
|---|---|---|---|---|---|---|---|---|
| 14:0 | 0.23 | 0.00 | 0.13 | 0.02 | 0.21 | 0.01 | 6.38 | 0.08 |
| 16:0 | 1.58 | 0.79 | 4.30 | 1.24 | 5.57 | 0.93 | 19.23 | 0.20 |
| 18:0 | 2.58 | 0.01 | 3.83 | 0.02 | 3.19 | 0.01 | 3.90 | 0.04 |
| Other Sat | 0.75 | 0.01 | 0.06 | 0.00 | 0.44 | 0.00 | 5.02 | 0.01 |
| Total Sat | 5.13 | | 8.33 | | 9.40 | | 34.53 | |
| 16:1ω7 | 0.28 | 0.00 | 0.17 | 0.03 | 0.25 | 0.00 | 7.06 | 0.05 |
| 18:1ω9 | 52.03 | 0.17 | 24.45 | 0.06 | 37.54 | 0.06 | 10.88 | 0.19 |
| 18:1ω7 | 3.28 | 0.02 | 1.04 | 0.02 | 2.18 | 0.02 | 2.69 | 0.01 |
| 20:1ω9 | 0.96 | 0.00 | 0.74 | 0.01 | 0.87 | 0.00 | 1.66 | 0.01 |
| Other Mono | 5.92 | 0.06 | 5.32 | 0.17 | 2.42 | 0.12 | 3.02 | 0.03 |
| Total Mono | 62.47 | | 31.73 | | 43.26 | | 25.31 | |
| 18:3ω3 | 10.07 | 0.03 | 19.57 | 0.04 | 16.04 | 0.03 | 2.39 | 0.04 |
| 18:4ω3 | 0.00 | 0.00 | 11.01 | 0.09 | 5.57 | 0.03 | 3.20 | 0.06 |
| 20:4ω3 | 0.00 | 0.00 | 0.00 | 0.00 | 0.00 | 0.00 | 0.73 | 0.01 |
| 20:5ω3 | 0.05 | 0.02 | 0.05 | 0.02 | 0.00 | 0.00 | 13.85 | 0.12 |
| 22:5ω3 | 0.14 | 0.04 | 0.00 | 0.00 | 0.00 | 0.00 | 1.46 | 0.02 |
| 22:6ω3 | 0.43 | 0.01 | 0.33 | 0.06 | 0.41 | 0.01 | 8.26 | 0.08 |
| Other ω3 | 0.00 | 0.00 | 0.00 | 0.00 | 0.00 | 0.00 | 0.59 | 0.00 |
| Total ω3 | 10.68 | | 30.96 | | 22.01 | | 30.46 | |
| 18:2ω6 | 21.71 | 0.04 | 19.82 | 0.03 | 20.81 | 0.01 | 6.18 | 0.10 |
| 18:3ω6 | 0.00 | 0.00 | 8.20 | 0.06 | 4.33 | 0.02 | 0.64 | 0.06 |
| 20:3ω6 | 0.00 | 0.00 | 0.00 | 0.00 | 0.00 | 0.00 | 0.00 | 0.00 |
| 20:4ω6 | 0.00 | 0.00 | 0.00 | 0.00 | 0.00 | 0.00 | 0.80 | 0.01 |
| 22:5ω6 | 0.00 | 0.00 | 0.00 | 0.00 | 0.00 | 0.00 | 0.19 | 0.03 |
| Other ω6 | 0.00 | 0.00 | 0.23 | 0.04 | 0.00 | 0.00 | 0.00 | 0.00 |
| Total ω6 | 21.71 | | 28.25 | | 25.13 | | 7.82 | |
| Other PUFA | 0.00 | 0.00 | 0.00 | 0.00 | 0.00 | 0.00 | 0.00 | 0.00 |
| Total PUFA | 32.40 | | 59.21 | | 47.15 | | 38.28 | |

Fish were initially anaesthetized (50 mg l$^{-1}$, benzocaine) and weights and lengths were recorded. Four fish were killed and assessed for initial lipid content and composition. Twenty five fish were randomly allotted into twelve 300 l tanks. Fish weights were not significantly different between tanks (43.6 g±0.7). The four diets were fed in triplicate on a ration of 1.1% body weight per day (% BW d$^{-1}$), in two equal feeds at 0900 and 1700 hrs by automatic belt feeders. Every three weeks all fish were anaesthetized (50 mg l$^{-1}$, benzocaine) and weighed. Fish were starved the day prior to measuring. Every 7 days the total feed consumption (kg DM) was estimated from the amount of feed that was not eaten by collection in sediment collectors. The amount of uneaten feed was estimated from the number of uneaten pellets using the average weight of a pellet from each feed (Helland et al., 1996).

Specific growth rates (SGR) were calculated as $$SGR(\% \text{ day}^{-1}) = 100 \times (\ln(W_2/W_1)) \times d^{-1}$$

where $W_1$ and $W_2$ were the weights (g) at the two times and d was the number of days.

At the end of the experiment fish were starved for one day prior to being anaesthetized (50 mg l$^{-1}$, benzocaine) and their weight and fork length measured. Three fish per tank were killed by a blow to the head after immersion in anaesthetic. Samples of tissue were dissected with red muscle and white muscle sampled below the dorsal fin. Samples were frozen at −80° C. until analysis.

Results

No significant difference was found between fish fed the four diets with respect to initial and final weight, weight gain, specific growth rate (SPR), total feed consumption (FC), feed efficiency ratio (FER), hepatosomatic index (HSI) or survival as determined using ANOVA (Table 7).

After 42 days there was no statistical difference in the composition of flesh lipid with respect to the lipid classes for the different dietary groups, in either red or white muscle (Tables 8 and 9). The predominant lipid class in red muscle was TAG (94.0-96.7%). There was significantly (p>0.02) less TAG in the fed fish (42.0-67.0%) compared to the initial measurement (82.0%) for the white muscle.

For fatty acid composition, there were significantly (p>0.01) higher levels of 18:3ω3 and 18:4ω3, in both white and red muscle tissues, in the fish fed SO than in fish fed the Mix diet. Both 18:3 ω3 and 18:4 ω3 levels were significantly higher than in the FO and CO fed fish (Tables 8 and 9). There were significantly (p>0.01) higher levels in both muscle tissues of 22:6 ω3 and total ω3 in the FO and SO diets compared to the Mix and CO diets. There were significantly (p>0.01) higher levels of 20:5 ω3 in the FO and SO fed fish compared to the CO fed fish in both the red and white muscle. The ratio of ω3/ω6 was significantly (p>0.01) lower in the CO and Mix diet fed fish compared to the SO and FO diets.

TABLE 7

Growth and efficiencies of Atlantic salmon fed experimental feeds with Canola oil (CO), Stearidonic acid rich oil (SO), 1:1 CO:SO (Mix) and Fish oil (FO) (mean ± SE).

| | Feed | | | |
|---|---|---|---|---|
| | CO | Mix | SO | FO |
| Initial weight (g) | 46.2 ± 2.5 | 44.6 ± 1.1 | 44.8 ± 1.1 | 42.3 ± 1.2 |
| Final Weight (g) | 81.4 ± 8.4 | 80.1 ± 1.9 | 76.9 ± 2.2 | 76.5 ± 3.3 |
| Weight gain (g) | 35.1 ± 5.9 | 35.5 ± 0.8 | 32.1 ± 2.0 | 34.1 ± 3.1 |
| SGR (% day$^{-1}$) | 1.2 ± 0.2 | 1.3 ± 0.0 | 1.2 ± 0.1 | 1.2 ± 0.1 |
| Total FC (g DM) | 41.4 ± 2.0 | 41.9 ± 0.8 | 40.5 ± 0.7 | 38.0 ± 1.8 |
| PER (g/g DM) | 0.8 ± 0.1 | 0.8 ± 0.0 | 0.8 ± 0.1 | 0.9 ± 0.0 |

TABLE 7-continued

Growth and efficiencies of Atlantic salmon fed experimental feeds with Canola oil (CO), Stearidonic acid rich oil (SO), 1:1 CO:SO (Mix) and Fish oil (FO) (mean ± SE).

| | Feed | | | |
|---|---|---|---|---|
| | CO | Mix | SO | FO |
| HSI (%) | 1.0 ± 0.1 | 1.0 ± 0.1 | 0.9 ± 0.2 | 0.9 ± 0.1 |
| Survival | 98.7 ± 1.4 | 98.7 ± 1.4 | 100.0 ± 0.0 | 100.0 ± 0.0 |

SO, stearidonic rich oil diet;
CO, canola oil diet;
Mix, 1:1 mix diet of canola oil and Stearidonic acid rich oils;
FO, fish oil diet;
DM, Dry matter
[1] SGR, Specific growth rate = 100 × (ln ($W_{final(g)}/W_{initial(g)}$)) × number of days (d)$^{-1}$
[2] FC, Total feed consumption = Total amount (g DM) consumed by an individual over 42 days.
[3] FER, feed efficiency ratio = total weight gain (g)/total feed consumption (g DM).
[4] HSI, hepatosomatic index = 100 (liver weight (g WW)/Total body weight (g WW)).
Survival during growth experiment.

In both muscle tissues, the FO diet surprisingly provided significantly (p>0.01) higher levels of 14:0, 16:0 and total saturates compared with CO and Mix fed. The FO diet also provided significantly (p>0.01) higher levels of 14:0 in both muscle tissues and 16:0 and total saturates in the red muscle compared with the SO fed fish. In both muscle tissues, FO and SO fed salmon had significantly (p>0.01) lower levels of 18:1 ω9 and total MUFA compared to the fish fed CO and Mix diets. There was significantly (p>0.01) higher levels of 18:2 ω6 and total ω6 in the fish fed CO and Mix diets compared with FO fed fish.

TABLE 8

FAME Content and lipid class composition of total lipid of Red muscle samples of Atlantic salmon fed Canola Oil (CO) 1:1 mix of Canola Oil:Stearidonic oil (Mix), Stearidonic oil (SO) diets and Fish oil (FO)

| FAME | Initial | SE | CO | SE | Mix | SE | SO | SE | FO | SE | Sig | f |
|---|---|---|---|---|---|---|---|---|---|---|---|---|
| 14:0 | 4.0 ± | 0.3b | 3.3 ± | 0.2a | 3.0 ± | 0.2a | 3.9 ± | 0.1a | 5.2 ± | 0.2b | 0.01 | 21.9 |
| 16:0 | 16.7 ± | 0.4b,c | 12.9 ± | 0.2a | 12.7 ± | 0.3a | 14.4 ± | 0.4a,b | 16.7 ± | 0.3c | 0.01 | 14.8 |
| 18:0 | 4.7 ± | 0.3 | 4.2 ± | 0.0 | 4.6 ± | 0.1 | 4.5 ± | 0.0 | 4.3 ± | 0.1 | | |
| Other SFA [e] | 2.0 ± | 0.0c | 1.7 ± | 0.0b | 1.4 ± | 0.0a | 1.8 ± | 0.0b | 1.9 ± | 0.0b,c | 0.01 | 11.1 |
| Total SFA | 27.3 ± | 0.7b,c | 22.2 ± | 0.9a | 21.7 ± | 0.4a | 24.6 ± | 1.0a,b | 28.2 ± | 0.4c | 0.01 | 13.9 |
| 16:1ω7c | 5.9 ± | 0.4c,d | 5.0 ± | 0.2b,c | 4.3 ± | 0.4a | 5.8 ± | 0.2b,c | 7.4 ± | 0.4d | 0.01 | 16.3 |
| 18:1ω9c | 13.4 ± | 0.6a | 30.5 ± | 1.3b | 27.9 ± | 1.1b | 16.1 ± | 0.5a | 14.9 ± | 0.2a | 0.01 | 26.5 |
| 18:1ω7c | 3.3 ± | 0.1c,d | 3.3 ± | 0.0b,c | 2.9 ± | 0.1a | 3.0 ± | 0.1a,b | 3.5 ± | 0.1d | 0.01 | 9.3 |
| 20:1ω9c | 1.4 ± | 0.1b | 2.0 ± | 0.0b | 1.3 ± | 0.4a,b | 1.7 ± | 0.0b | 0.4 ± | 0.4a | 0.01 | 5.0 |
| Other MUFA [f] | 2.5 ± | 0.0a | 2.3 ± | 0.0a | 2.5 ± | 0.0a | 2.5 ± | 0.0a | 4.2 ± | 0.0b | 0.01 | 10.2 |
| Total MUFA | 26.4 ± | 0.5a | 43.2 ± | 2.2b | 38.9 ± | 1.1b | 29.1 ± | 0.6a | 30.5 ± | 0.5a | 0.01 | 28.2 |
| 18:3ω3 ALA | 0.7 ± | 0.0a | 2.0 ± | 0.1b | 3.9 ± | 0.2c | 5.7 ± | 0.2d | 2.0 ± | 0.0b | 0.01 | 65.8 |
| 18:4ω3 SDA | 2.3 ± | 0.2a | 2.2 ± | 0.1a | 3.7 ± | 0.b | 4.3 ± | 0.3c | 2.6 ± | 0.1a | 0.01 | 92.2 |
| 20:4ω3 | 1.1 ± | 0.0a | 1.0 ± | 0.0a,b | 1.2 ± | 0.0b | 1.4 ± | 0.0c | 1.2 ± | 0.0a,b | 0.01 | 10.4 |
| 20:5ω3 EPA | 8.6 ± | 0.2b | 4.8 ± | 0.3a | 4.4 ± | 0.3a | 6.2 ± | 0.2b | 7.6 ± | 0.3b | 0.01 | 25.2 |
| 22:5ω3 DPA | 3.2 ± | 0.1c | 2.3 ± | 0.1a,b | 2.2 ± | 0.2a | 3.1 ± | 0.1b,c | 3.7 ± | 0.1c | 0.01 | 11.0 |
| 22:6ω3 DHA | 19.2 ± | 1.0c | 9.6 ± | 0.5a | 9.0 ± | 0.7a | 12.5 ± | 0.6b | 14.4 ± | 0.7b | 0.01 | 13.6 |
| Other ω3 [g] | 1.0 ± | 0.0 | 0.8 ± | 0.0 | 0.7 ± | 0.0 | 1.1 ± | 0.0 | 1.3 ± | 0.0 | | |
| Total ω3 | 36.2 ± | 0.6b | 22.6 ± | 1.9a | 25.0 ± | 1.1a | 34.3 ± | 1.1b | 32.8 ± | 0.6b | 0.01 | 16.3 |
| 18:2ω6 LA | 2.8 ± | 0.1a | 7.6 ± | 0.4b | 9.1 ± | 0.7b | 6.2 ± | 0.6a,b | 3.9 ± | 0.7a | 0.01 | 12.7 |
| 18:3ω6 | 0.2 ± | 0.0a | 0.5 ± | 0.0b | 0.5 ± | 0.0b | 1.5 ± | 0.2c | 0.8 ± | 0.2a,b | 0.01 | 8.1 |
| 20:3ω6 | 0.2 ± | 0.0a | 0.6 ± | 0.0b,c | 1.0 ± | 0.1c | 0.7 ± | 0.1b | 0.2 ± | 0.1a,b | 0.01 | 12.5 |
| 20:4ω6 | 1.3 ± | 0.2a,b | 0.5 ± | 0.0a | 0.5 ± | 0.0a | 0.6 ± | 0.0a,b | 0.6 ± | 0.0b | 0.01 | 5.3 |
| 22:5ω6 | 0.3 ± | 0.0b | 0.2 ± | 0.0a,b | 0.2 ± | 0.0a | 0.3 ± | 0.0a,b | 0.3 ± | 0.0b | 0.01 | 5.5 |
| Other ω6 [h] | 0.8 ± | 0.0 | 1.0 ± | 0.0 | 0.8 ± | 0.0 | 0.8 ± | 0.0 | 0.9 ± | 0.0 | | |
| Total ω6 | 5.3 ± | 0.2a | 9.9 ± | 0.9c | 11.6 ± | 0.8c | 8.5 ± | 1.2b,c | 5.8 ± | 0.1a,b | 0.01 | 12.8 |
| Other PUFA [i] | 4.8 ± | 0.2 | 2.0 ± | 0.0 | 2.8 ± | 0.1 | 3.4 ± | 0.1 | 2.7 ± | 0.1 | | |
| Total PUFA | 46.3 ± | 1.3b | 34.6 ± | 2.1a | 39.4 ± | 1.3a,b | 46.3 ± | 1.2b | 41.3 ± | 0.9b | 0.01 | 15.1 |
| Ratios | | | | | | | | | | | | |
| ω3/ω6 | 6.8 ± | 0.3b | 2.3 ± | 0.4a | 2.2 ± | 0.2a | 4.0 ± | 0.1b | 5.6 ± | 0.2b | 0.01 | 54.5 |

TABLE 8-continued

FAME Content and lipid class composition of total lipid of Red muscle samples of Atlantic salmon fed Canola Oil (CO) 1:1 mix of Canola Oil:Stearidonic oil (Mix), Stearidonic oil (SO) diets and Fish oil (FO)

| FAME | Initial | SE | CO | SE | Mix | SE | SO | SE | FO | SE | Sig | f |
|---|---|---|---|---|---|---|---|---|---|---|---|---|
| Lipid Class | | | | | | | | | | | | |
| TAG | 96.7 ± | 0.4 | 96.7 ± | 0.3 | 95.4 ± | 0.2 | 96.6 ± | 0.4 | 94.0 ± | 0.9 | | |
| FFA | 0.7 ± | 0.1a | 0.7 ± | 0.1a | 1.8 ± | 0.1a,b | 0.5 ± | 0.1a | 2.5 ± | 0.6b | 0.01 | 8.0 |
| ST | 0.8 ± | 0.2 | 1.1 ± | 0.0 | 1.0 ± | 0.1 | 1.0 ± | 0.0 | 0.9 ± | 0.4 | | |
| PL | 1.8 ± | 0.2 | 1.5 ± | 0.2 | 1.7 ± | 0.2 | 1.8 ± | 0.3 | 2.6 ± | 0.3 | | |
| mg/g Wet[j] | 17.8 ± | 1.0 | 22.9 ± | 0.7 | 22.2 ± | 1.1 | 24.5 ± | 1.8 | 28.1 ± | 5.5 | | |
| mg/g Dry[j] | 44.3 ± | 2.8 | 53.6 ± | 0.9 | 57.0 ± | 7.7 | 54.1 ± | 2.9 | 56.6 ± | 7.1 | | |

SFA, Saturated fatty acids;
MUFA, monounsaturated fatty acids;
PDFA, polyunsaturated fatty acids;
DHA, Docosahexaenoic Acid;
DPA, Docosapentaenoic Acid;
EPA, Eicosapentaenoic Acid;
SDA, Stearidonic acid;
LA, Linoleic acid;
ALA, α- Linolenic acid;
TAG; Triacylglycerol;
FFA, free fatty acid;
ST, sterol;
PL, polar lipid;
WW, wet weight;
Sig, Significance;
f, Mean sum of squares.
a,b,c,d Mean values across the row not sharing a common letter were significantly different as determined by Turkey-Kramer HSD; df = 4.15.
[e] Other SFA includes 15:0, 17:0, 20:0, 22:0 and 24:0
[f] Other MUFA includes 16:1ω9, 16:1ω5, 18:1ω5, 20:1ω7, 22:1ω9, 22:1ω11 and 24:1ω9
[g] Other ω3 PUFA include 21:5ω3 and 24:6ω3
[h] Other ω6 PUFA include 20:2ω6, 20:3ω6, 22:4ω6 and 24:5ω6
[i] Other PUFA include 16:2ω4, 16:3ω4 and 18:2ω9
[j] Determined by TLC-FID

TABLE 9

FAME Content and lipid class composition of the total lipid of white muscle samples of Atlantic salmon

| FAME | Initial | SE | CO | SE | Mix | SE | SO | SE | FO | SE | Sig | f |
|---|---|---|---|---|---|---|---|---|---|---|---|---|
| 14:0 | 3.9 ± | 0.4b | 2.3 ± | 0.1a | 1.9 ± | 0.2a | 2.3 ± | 0.1a | 3.6 ± | 0.2b | 0.01 | 13.0 |
| 16:0 | 18.3 ± | 0.4a,b | 14.8 ± | 0.3a | 15.2 ± | 0.3a | 16.8 ± | 0.6a,b | 19.7 ± | 0.3b | 0.01 | 5.0 |
| 18:0 | 5.7 ± | 0.3 | 4.8 ± | 0.0 | 5.6 ± | 0.1 | 5.6 ± | 0.1 | 5.0 ± | 0.1 | | |
| Other SFA[e] | 1.8 ± | 0.0 | 1.0 ± | 0.0 | 0.8 ± | 0.0 | 1.0 ± | 0.0 | 1.4 ± | 0.0 | | |
| Total SFA | 29.7 ± | 1.1a,b | 22.9 ± | 0.9a | 23.5 ± | 1.7a | 25.7 ± | 1.4a,b | 29.6 ± | 0.5b | 0.01 | 5.1 |
| 16:1ω7c | 5.6 ± | 0.5b | 3.1 ± | 0.2a | 2.7 ± | 0.4a | 3.1 ± | 0.1a | 5.1 ± | 0.4b | 0.01 | 14.1 |
| 18:1ω9c | 14.2 ± | 0.7b | 27.2 ± | 1.3c | 22.2 ± | 1.3b,c | 11.3 ± | 0.8a | 11.0 ± | 6.7a | 0.01 | 5.9 |
| 18:1ω7c | 3.2 ± | 0.1c | 2.9 ± | 0.0b,c | 2.5 ± | 0.1a,b | 2.2 ± | 0.1a | 3.1 ± | 0.1c | 0.01 | 18.0 |
| 20:1ω9c | 1.1 ± | 0.2 | 1.5 ± | 0.0 | 0.9 ± | 0.4 | 1.0 ± | 0.0 | 0.5 ± | 0.4 | | |
| Other MUFA[f] | 3.3 ± | 0.1 | 2.1 ± | 0.0 | 2.0 ± | 0.0 | 1.7 ± | 0.0 | 2.4 ± | 0.0 | | |
| Total MUFA | 27.3 ± | 0.7b | 36.8 ± | 2.3c | 30.2 ± | 2.1b | 19.3 ± | 2.4a | 22.0 ± | 1.1a | 0.01 | 4.7 |
| 18:3ω3 ALA | 1.0 ± | 0.0a | 2.1 ± | 0.1b | 3.5 ± | 0.7c | 6.3 ± | 0.4d | 1.7 ± | 0.1b | 0.01 | 30.1 |
| 18:4ω3 SDA | 2.0 ± | 0.2a | 1.6 ± | 0.0a | 2.8 ± | 0.3a | 3.9 ± | 0.1b | 2.0 ± | 0.1a | 0.01 | 10.8 |
| 20:4ω3 | 1.1 ± | 0.0a,b | 0.8 ± | 0.0a | 1.2 ± | 0.0a,b | 1.3 ± | 0.1b | 1.0 ± | 0.0a,b | 0.01 | 4.7 |
| 20:5ω3 EPA | 7.4 ± | 0.2b,c | 4.8 ± | 0.3a | 5.4 ± | 0.3a,b | 7.3 ± | 0.5b,c | 8.6 ± | 0.3c | 0.01 | 7.0 |
| 22:5ω3 DPA | 3.0 ± | 0.1b,c | 2.1 ± | 0.1a | 2.2 ± | 0.2a | 2.6 ± | 0.1a,b | 3.6 ± | 0.2c | 0.01 | 10.3 |
| 22:6ω3 DHA | 20.0 ± | 1.2a,b | 16.2 ± | 0.9a | 18.3 ± | 0.7a | 22.2 ± | 0.6b | 24.2 ± | 0.7b | 0.01 | 8.0 |
| Other ω3[g] | 0.8 ± | 0.1 | 0.5 ± | 0.0 | 0.3 ± | 0.0 | 0.6 ± | 0.0 | 0.9 ± | 0.0 | | |
| Total ω3 | 35.4 ± | 0.2b | 28.2 ± | 2.1a | 33.7 ± | 1.1a,b | 44.2 ± | 2.6c | 42.0 ± | 2.4b,c | 0.01 | 14.4 |
| 18:2ω6LA | 2.9 ± | 0.2a | 7.6 ± | 0.4b | 7.5 ± | 0.7b | 5.6 ± | 0.6b | 3.2 ± | 0.7a | 0.02 | 4.0 |
| 18:3ω6 | 0.6 ± | 0.2a | 0.5 ± | 0.0a | 0.9 ± | 0.4a,b | 1.5 ± | 0.2b | 0.4 ± | 0.3a | 0.01 | 12.0 |
| 20:3ω6 | 0.1 ± | 0.0a | 1.0 ± | 0.1b | 1.1 ± | 0.1b | 0.9 ± | 0.2b | 0.1 ± | 0.1a | 0.02 | 4.5 |
| 20:4ω6 | 1.3 ± | 0.2 | 1.0 ± | 0.0 | 1.3 ± | 0.0 | 1.0 ± | 0.1 | 0.9 ± | 0.0 | | |
| 22:5ω6 | 0.2 ± | 0.0 | 0.4 ± | 0.0 | 0.2 ± | 0.0 | 0.3 ± | 0.0 | 0.2 ± | 0.0 | | |
| Other ω6[h] | 1.3 ± | 0.2 | 0.9 ± | 0.0 | 0.6 ± | 0.0 | 0.5 ± | 0.0 | 0.4 ± | 0.0 | | |
| Total ω6 | 5.9 ± | 0.1a | 10.8 ± | 1.3b | 10.6 ± | 1.8b | 8.3 ± | 1.4a,b | 4.7 ± | 0.2a | 0.02 | 6.2 |
| Other PUFA[i] | 1.7 ± | 0.0 | 1.4 ± | 0.0 | 1.9 ± | 0.1 | 2.5 ± | 0.1 | 1.7 ± | 0.1 | | |
| Total PUFA | 43.0 ± | 1.2a | 40.4 ± | 1.4a | 46.3 ± | 2.3a,b | 55.0 ± | 1.1c | 48.4 ± | 0.9b | | |

TABLE 9-continued

FAME Content and lipid class composition of the total lipid of white muscle samples of Atlantic salmon

| FAME | Initial | SE | CO | SE | Mix | SE | SO | SE | FO | SE | Sig | f |
|---|---|---|---|---|---|---|---|---|---|---|---|---|
| Ratios | | | | | | | | | | | | |
| ω3/ω6 | 6.0 ± | 0.1b,c | 2.6 ± | 0.5a | 3.2 ± | 0.1a | 5.3 ± | 0.1b | 8.8 ± | 0.2c | 0.02 | 16.2 |
| Lipid Class | | | | | | | | | | | | |
| TAG | 82.0 ± | 2.6c | 46.2 ± | 4.9a | 67.0 ± | 4.6a | 59.9 ± | 2.0a | 50.5 ± | 12.7a | 0.02 | 3.1 |
| FFA | 1.7 ± | 0.3b,c | 1.9 ± | 0.2c | 0.4 ± | 0.1a | 1.8 ± | 0.1b,c | 0.5 ± | 0.2a,b | 0.02 | 5.9 |
| ST | 2.1 ± | 0.4 | 4.0 ± | 0.2 | 2.1 ± | 0.2 | 3.8 ± | 0.3 | 2.2 ± | 0.3 | | |
| PL | 14.2 ± | 2.1 | 47.6 ± | 4.9 | 30.5 ± | 4.7 | 34.6 ± | 1.9 | 46.8 ± | 12.4 | | |
| mg/g Wet$^i$ | 8.4 ± | 0.3 | 9.1 ± | 0.1 | 9.0 ± | 0.2 | 9.2 ± | 0.1 | 8.2 ± | 0.3 | | |
| mg/g Dry$^j$ | 10.1 ± | 1.0a | 15.2 ± | 0.4b | 14.2 ± | 0.6b | 14.9 ± | 0.2b | 15.1 ± | 1.0b | 0.02 | 8.9 |

Abbreviations and other footnote definitions, see Table 8.

Discussion

The inclusion of SO at 130 or 65 g/kg of diet for Atlantic salmon parr did not significantly influence growth or feed conversion rates compared to other experimental diets during the 42 day growth trial in freshwater (Table 7). There was little effect between diets in the lipid class profiles (Tables 8 and 9). There was significantly less TAG in the white muscle of the fed fish compared to the diet due to the inclusion of oil in the diet at a level of 130 g/kg compared to the commercial diet (approx. 300 g/kg) they were fed pre-experiment.

Fish muscle FA profiles were closely related to the FA profile of their diet. It has been shown previously for salmon fed using canola, sunflower and linseed oils, i.e. diets rich in ALA and without EPA and DHA, that there was a significant reduction in total ω3 and ω3 LC-PUFA, in particular DHA and EPA (Bransden et al., 2003; Bell et al., 2003; Polvi and Ackman, 1992; Bell et al., 2004). Therefore, minimal conversion to, or negligible accumulation of, LC-PUFA occurred when fish were fed vegetable oil. In those studies growth rates and the health of fish fed vegetable oils were not affected.

In the study described here, Atlantic salmon parr sizes were initially 43.6 g±0.7 g to a final weight of 72.4 g±1.9 g. The fish were at an important stage of the growth. Pre-smoltification Atlantic salmon store FA, in particular ω3 LC-PUFA, prior to the energy requiring transfer to salt water, during which salmon undergo major changes in their lipid metabolism.

The inclusion of SDA at 14.3 or 7.2 g/kg significantly influenced the FA profiles of the salmon (Tables 8 and 9). Fish fed on the diet containing the higher level of SDA had significantly higher levels of EPA, DPA, DHA and total ω3 in the muscle samples than fish fed on the CO diet. In some respects, the fatty acid composition of the fish tissues was improved over that of fish fed the FO diet. For example, the level of saturated fat was reduced. The SO diet was also advantageous for this feature in combination with the high levels of LC-PUFA.

Neither the CO diet nor the SO diet contained EPA or DHA at substantial levels, being <0.7% of the fatty acid present in the lipid, the trace level probably originating with the fishmeal component. Therefore the increased accumulation of EPA; DPA and DHA in the fish tissues must have represented increased biosynthesis of the fatty acids from SDA in the fish.

This experiment showed that high levels of total ω3, DHA and EPA could be maintained in fish such as salmon without their inclusion as dietary FA. This experiment also demonstrated that the levels of fatty acids achieved, as reported in Tables 8 and 9, for example the levels of SDA, EPA, DPA, DHA, total LC-PUFA ω3, or total ω3 PUFA (includes C18 fatty acids), were minimum levels that could be achieved through feeding the fish a diet including plant derived SDA, and that even higher levels could be expected by using diets with even higher levels of SDA and/or longer feeding times.

The conversion of ALA to SDA involves the desaturation at the Δ6 position of the carbon chain with further chain elongation steps, followed by Δ5 desaturation to form EPA. The synthesis of EPA to DHA requires additional chain elongations and also involves the Δ6 desaturation in the conversion of 24:5 ω3 to 24:6 ω3 before chain shortening to DHA (FIG. 1); this is termed the Sprecher pathway. With the conversion of 18:2 ω6 to 20:4 ω6 also using the Δ6 desaturase, it was possible that the high levels of 18:2 ω6 in vegetable oils might compete for this enzyme and therefore minimal conversion of ALA to SDA would occur in the ω3 pathway. We have found here that this problem can be alleviated by adding SDA in the fish diet. The results indicated that a SDA rich plant oil could be used as a source of dietary oil for aquafeeds and, importantly, that the use of SDA oil did not affect the amount of ω3 LC-PUFA in the FA profile of salmon muscle.

Example 3. Prawn and Lobster Feedstuffs

For feeding of lobsters, prawns or other crustacean with diets high in SDA oil, the following feed compositions can be used (Table 10). Values provided as g/kg dry matter.

Example 4. Isolation of a Gene Encoding a Δ6-Desaturase from *Echium* plantagineum Some plant species such as evening primrose (*Oenothera biennis*), common borage (*Borago officinalis*), blackcurrant (*Ribes nigrum*), and some *Echium* species belonging to the Boragenacae family contain the ω6- and ω3-desaturated C18 fatty acids, γ-linolenic acid (18:3ω6, GLA) and stearidonic acid (18:4ω3, SDA) in their leaf lipids and seed TAG (Guil-Guerrero et al., 2000). GLA and SDA are recognized as beneficial fatty acids in human nutrition. The first step in the synthesis of LC-PUFA is a M-desaturation. GLA is synthesized by a Δ6-desaturase that introduces a double bond into the M-position of LA. The same enzyme is also able to introduce a double bond into Δ6-position of ALA, producing SDA. M-desaturase genes have been cloned from members of the Boraginacae, like borage (Sayanova et al., 1997) and two *Echium* species (Garcia-Maroto et al., 2002).

TABLE 10

Prawn and Lobster feedstuffs.

| | Spiny Lobster | Prawn |
|---|---|---|
| Fish meal (defatted) | 250 | 0 |
| Fish meal (standard) | 0 | 200 |
| Krill meal | 0 | 185 |
| Soybean Meal | 150 | 150 |
| Wheat gluten | 100 | 100 |
| *Echium plantagineum* Oil | 110 | 100 |
| Cholesterol | 2 | 2 |
| Lecithin | 12 | 12 |
| Pre-gel starch | 175 | 100 |
| Manucol | 60 | 60 |
| Vit Pre-Mix | 2.00 | 2.00 |
| Banox E | 0.20 | 0.20 |
| Choline Chloride | 0.20 | 0.20 |
| Vitamin C[a] | 1.00 | 1.00 |
| Carophyll pink | 1.50 | 1.50 |
| Min Pre-Mix [b] | 0.01 | 0.01 |
| TSP Phosphate | 20.00 | 20.00 |
| Mussel meal | 50.00 | 0.00 |
| Filler | 66.00 | 66.00 |
| Total | 1000 | 1000 |
| SDA | 1.54 | 1.40 |

SO, stearidonic rich oil crossential SA14 from Croda chemicals;
[a] L-Ascorbyl-2-polyphosphate (Stay-C, Roche Vitamins Australia, French Forest, NSW, Australia).
[b] Mineral mix (TMV4) to supply per kilogram feed: 117 mg $CuSO_4 \cdot 5H_2O$, 7.19 mg KI, 1815 mg $FeSO_4 \cdot 7H_2O$, 307 mg $MnSO_4 \cdot H_2O$, 659 mg $ZnSO_4 \cdot 7H_2O$, 3.29 mg $Na_2SeO_3$, 47.7 mg $CoSO_4 \cdot 7H_2O$
Soybean (Hamlet Protein A/S, Horsens, Denmark), wheat gluten (Starch Australasia, Land Cove, NSW, Australia) and BOIIC pre-gelatinised maize starch (Penford Australia Limited, Lane Cove, NSW, Australia) were used. S-tay-C and Carophyll pink were supplied from Roche Vitamins Australia (Frenchs Forest, NSW, Australia), Mussel meal obtained from New Zealand Greenshell™ mussel, (Sealord P/L Nelson, New Zealand) and the remaining ingredients were supplied by Sigma-Aldrich (Castle Hill, NSW, Australia).

*Echium plantagineum* is a winter annual native to Mediterranean Europe and North Africa. Its seed oil is unusual in that it has a unique ratio of ω3 and ω6 fatty acids and contains high amounts of GLA (9.2%) and SDA (12.9%) (Guil-Guerrero et al., 2000), suggesting the presence of M-desaturase activity involved in desaturation of both ω3 and ω6 fatty acids in seeds of this plant.

Cloning of *E. Plantagineum* EplD6Des Gene

Degenerate primers with built-in XbaI or SacI restriction sites corresponding to N- and C-termini amino acid sequences MANAIKKY (SEQ ID NO:14) and EALNTHG (SEQ ID NO:15) of known *Echium pitardii* and *Echium gentianoides* (Garcia-Maroto et al., 2002) L6-desaturases were used for RT-PCR amplification of M-desaturase sequences from *E. platangineum* using a proofreading DNA polymerase Pfu Turbo® (Stratagene). The 1.35 kb PCR amplification product was inserted into pBluescript SK(+) at the XbaI and SacI sites to generate plasmid pXZP106. The nucleotide sequence of the insert was determined. It comprised an open reading frame encoding a polypeptide of 438 amino acid residues (SEQ ID NO:10) which had a high degree of homology with other reported Δ6-desaturases from *E. gentianoides* (SEQ ID NO:11), *E. pitardii* (SEQ ID NO:12) and *Borago officinalis* (SEQ ID NO:4). It has a cytochrome $b_5$ domain at the N-terminus, including the HPGG (SEQ ID NO:16) motif in the heme-binding region, as reported for other Δ6- and Δ8-desaturases (Sayanova et al. 1997; Napier et al. 1999). In addition, the *E. plantagineum* Δ6 desaturase contains three conserved histidine boxes present in majority of the 'front-end' desaturases (Napier et al., 1999). Cluster analysis including representative members of Δ6 and Δ8 desaturases showed a clear grouping of the cloned gene with other Δ6 desaturases especially those from *Echium* species.

Heterologous Expression of *E. plantagineum* Δ6-Desaturase Gene in Yeast

Expression experiments in yeast were carried out to confirm that the cloned *E. platangineum* gene (cDNA sequence provided as SEQ ID NO:25) encoded a Δ6-desaturase enzyme. The gene fragment was inserted as an XbaI-SacI fragment into the Small-SacI sites of the yeast expression vector pSOS (Stratagene) containing the constitutive ADH1 promoter, resulting in plasmid pXZP271. This was transformed into yeast strain S288Cα by a heat shock method and transformant colonies selected by plating on minimal media plates. For the analysis of enzyme activity, 2 mL yeast clonal cultures were grown to an $O.D._{600}$ of 1.0 in yeast minimal medium in the presence of 0.1% NP-40 at 30° C. with shaking. Precursor free-fatty acids, either linoleic or linolenic acid as 25 mM stocks in ethanol, were added so that the final concentration of fatty acid was 0.5 mM. The cultures were transferred to 20° C. and grown for 2-3 days with shaking. Yeast cells were harvested by repeated centrifugation and washing first with 0.1% NP-40, then 0.05% NP-40 and finally with water. Fatty acids were extracted and analyzed. The peak identities of fatty acids were confirmed by GC-MS.

The transgenic yeast cells expressing the *Echium* EplD6Des were able to convert LA and ALA to GLA and SDA, respectively. Around 2.9% of LA was converted to GLA and 2.3% of ALA was converted to SDA, confirming the Δ6-desaturase activity encoded by the cloned gene.

Functional Expression of *E. platangineum* 46-Desaturase Gene in Transgenic Tobacco In order to demonstrate that the EplD6Des gene could confer the synthesis of Δ6 desaturated fatty acids in transgenic plants, the gene was expressed in tobacco plants. To do this, the gene fragment was excised from pXZP106 as an XbaI-SacI fragment and cloned into the plant expression vector pBI121 (Clonetech) at the XbaI and SacI sites under the control of a constitutive 35S CaMV promoter, to generate plant expression plasmid pXZP341. This was introduced into *Agrobacterium tumefaciens* AGL1, and used for transformation of tobacco W38 plant tissue, by selection with kanamycin.

Northern blot hybridization analysis of transformed plants was carried out to detect expression of the introduced gene, and total fatty acids present in leaf lipids of wild-type tobacco W38 and transformed tobacco plants were analysed as described above. Untransformed plants contained appreciable amounts of LA (21% of total fatty acids) and ALA (37% of total fatty acids) in leaf lipids. As expected, neither GLA nor SDA, products of Δ6-desaturation, were detected in the untransformed leaf. Furthermore, transgenic tobacco plants transformed with the pBI121 vector had similar leaf fatty acid composition to the untransformed W38 plants. In contrast, leaves of transgenic tobacco plants expressing the EplD6Des gene showed the presence of additional peaks with retention times corresponding to GLA and SDA. The identity of the GLA and SDA peaks were confirmed by GC-MS. Notably, leaf fatty acids of plants expressing the EplD6Des gene consistently contained approximately a two-fold higher concentration of GLA than SDA even when the total Δ6-desaturated fatty acids amounted up to 30% of total fatty acids in their leaf lipids (Table 11).

TABLE 11

Fatty acid composition in lipid from transgenic tobacco leaves (%).

| Plant | 16:0 | 18:0 | 18:1 | 18:2 | GLA | 18:3 | SDA | Total Δ6-desaturated products |
|---|---|---|---|---|---|---|---|---|
| W38 | 21.78 | 5.50 | 2.44 | 21.21 | — | 37.62 | — | — |
| ET27-1 | 20.33 | 1.98 | 1.25 | 10.23 | 10.22 | 41.10 | 6.35 | 16.57 |
| ET27-2 | 18.03 | 1.79 | 1.58 | 14.42 | 1.47 | 53.85 | 0.48 | 1.95 |
| ET27-4 | 19.87 | 1.90 | 1.35 | 7.60 | 20.68 | 29.38 | 9.38 | 30.07 |
| ET27-5 | 15.43 | 2.38 | 3.24 | 11.00 | 0.84 | 49.60 | 0.51 | 1.35 |
| ET27-6 | 19.85 | 2.05 | 1.35 | 11.12 | 4.54 | 50.45 | 2.19 | 6.73 |
| ET27-8 | 19.87 | 2.86 | 2.55 | 11.71 | 17.02 | 27.76 | 7.76 | 24.78 |
| ET27-11 | 17.78 | 3.40 | 2.24 | 12.62 | 1.11 | 51.56 | 0.21 | 1.32 |
| ET27-12 | 16.84 | 2.16 | 1.75 | 13.49 | 2.71 | 50.80 | 1.15 | 3.86 |

Northern analysis of multiple independent transgenic tobacco lines showed variable levels of the EplD6Des transcript which generally correlated with the levels of Δ6-desaturated products synthesized in the plants. For example, transgenic plant ET27-2 which contained low levels of the EplD6Des transcript synthesised only 1.95% of its total leaf lipids as Δ6-desaturated fatty acids. On the other hand, transgenic plant ET27-4 contained significantly higher levels of EplD6Des transcript and also had a much higher proportion (30%) of Δ6-desaturated fatty acids in its leaf lipids.

Analysis of the individual tobacco plants showed that, without exception, GLA was present at a higher concentration than SDA even though a higher concentration of ALA than LA was present in untransformed plants. In contrast, expression of EplD6Des in yeast had resulted in approximately equivalent levels of conversion of LA into GLA and ALA into SDA. Echium plantagineum seeds, on the other hand, contain higher levels of SDA than GLA. EplD6Des probably carries out its desaturation in vivo in Echium plantagineum seeds on LA and ALA esterified to phosphatidyl choline (PC) (Jones and Harwood 1980). In the tobacco leaf assay, the enzyme is most likely desaturating LA and ALA esterified to the chloroplast lipid monogalactosyldiacylglycerol (MGDG) (Browse and Slack, 1981). In the yeast assay, free fatty acid precursors LA and ALA added to the medium most likely enter the acyl-CoA pool and are available to be acted upon by EplD6Des in this form.

In conclusion, the transgenic tobacco plant described herein can be used to produce feedstuffs of the invention.

Functional Expression of E. platangineum Δ6-Desaturase Gene in Transgenic Seed

To show seed-specific expression of the Echium Δ6-desaturase gene, the coding region was inserted into the seed-specific expression cassette as follows. An NcoI-SacI fragment including the Δ6-desaturase coding region was inserted into pXZP6, a pBluescriptSK derivative containing a Nos terminator, resulting in plasmid pXZP157. The SmaI-ApaI fragment containing the coding region and terminator EplD6Des-NosT was cloned into pWVec8-Fp1 downstream of the Fp1 prompter, resulting in plasmid pXZP345. The plasmid pXZP345 was used for transforming wild type Arabidopsis plants, ecotype Columbia, and transgenic plants selected by hygromycin B selection. The transgenic plants transformed with this gene were designated "DP" plants.

Fatty acid composition analysis of the seed oil from T2 seed from eleven T1 plants transformed with the construct showed the presence of GLA and SDA in all of the lines, with levels of Δ6-desaturation products reaching to at least 11% (Table 12). This demonstrated the efficient M-desaturation of LA and ALA in the seed.

Example 5. Transformation of Flax with a Seed-Specific Echium Δ6 Fatty Acid Desaturase Gene Construct The full protein coding region of the Echium Δ6 fatty acid desaturase gene was PCR amplified with the following primers incorporating an XhoI site at the both ends: Ed6F: 5'-ACTCGAGCCACCATGGCTAATGCAATCAA-3' (SEQ ID NO:17) and Ed6R: 5'-CCTCGAGCTCAACCATGAGT-ATTAAGAG-3' (SEQ ID NO:18). PCR was conducted by heating to 94° C. for 2 min, followed by 30 cycles of 94° C. for 40 sec, 62° C. for 40 sec and 72° C. for 1 min 20 sec. After the last cycle, reactions were incubated for 10 min at 72° C. The PCR fragment was cloned into a pGEMTeasy® vector (Promega) and sequenced to ensure that no PCR-induced errors had been introduced. The insert was then digested with XhoI and inserted into the XhoI site of the binary vector, pWBVec8, in a sense orientation between the promoter derived from a seed-specifically expressed flax 2S storage protein gene, linin, and its polyadenylation site/transcription terminator.

TABLE 12

Fatty acid composition in transgenic Arabidopsis seeds expressing Δ6-desaturase from Echium.

| Plant Columbia | Fatty acid (%) | | | | | | | | | Total Δ6-desaturation products (%) |
|---|---|---|---|---|---|---|---|---|---|---|
| | 16:0 | 18:0 | 18:1$^{\Delta 9}$ | 18:2$^{\Delta 9, 12}$ (LA) | 18:3$^{\Delta 6, 9, 12}$ (GLA) | 18:3$^{\Delta 9, 12, 15}$ (ALA) | 18:4$^{\Delta 6, 9, 12, 15}$ (SDA) | 20:0 | 20:1 | |
| DP-2 | 8.0 | 2.8 | 22.9 | 27.3 | 2.5 | 11.3 | 0.7 | 1.6 | 15.8 | 3.2 |
| DP-3 | 7.8 | 2.7 | 20.6 | 25.9 | 3.0 | 12.1 | 0.8 | 1.7 | 17.8 | 3.8 |
| DP-4 | 7.8 | 2.8 | 20.4 | 28.5 | 1.2 | 13.7 | 0.4 | 1.7 | 16.1 | 1.5 |
| DP-5 | 8.2 | 3.2 | 17.4 | 29.3 | 1.2 | 14.2 | 0.3 | 2.1 | 15.6 | 1.6 |
| DP-7 | 8.2 | 2.9 | 18.4 | 26.7 | 5.0 | 12.7 | 1.4 | 1.7 | 15.2 | 6.4 |
| DP-11 | 9.0 | 3.5 | 17.8 | 28.4 | 3.0 | 13.4 | 0.9 | 2.1 | 13.9 | 3.8 |
| DP-12 | 8.6 | 3.0 | 18.9 | 27.8 | 3.3 | 12.6 | 1.0 | 1.8 | 15.4 | 4.3 |
| DP-13 | 8.7 | 2.9 | 14.4 | 27.3 | 8.5 | 13.7 | 2.6 | 1.7 | 12.4 | 11.1 |
| DP-14 | 9.3 | 2.9 | 14.2 | 32.3 | 2.1 | 15.4 | 0.7 | 1.8 | 12.8 | 2.8 |
| DP-15 | 8.2 | 2.9 | 17.8 | 30.1 | 0.3 | 15.3 | 0.2 | 1.9 | 15.5 | 0.5 |
| DP-16 | 8.0 | 2.8 | 19.5 | 29.2 | 2.7 | 13.1 | 0.8 | 1.7 | 14.2 | 3.5 |

The binary vector, pWBVec8 contained a hygromycin resistance gene as a selectable marker for plant transformation (Wang et al., 1998). The construct, designated pVLin-Ed6 and containing the *Echium* Δ6 desaturase gene for seed-specific expression was shown schematically in FIG. 2. The linin promoter (SEQ ID NO:23) and terminator (SEQ ID NO:24) have previously been shown to confer expression in a highly specific manner in developing flax embryos, being expressed maximally in flax seed at the same time as oil accumulation in flax seeds. Both the linin promoter and terminator elements were able to drive seed specific expression of transgenes in flax at levels comparable to the highly active bean phaseolin promoter.

Approximately 150 hypocotyls were excised from 6-7 day old seedlings of flax cultivar Ward grown in sterile condition on MS media. This cultivar was found to produce the highest transformation efficiency among many flax cultivars, however many other cultivars were also amendable for gene transformation. The hypocotyls were inoculated and co-cultivated with *Agrobacterium tumefaciens* strain AGL1 harbouring the binary construct pVLin-Ed6 in a similar fashion to that described for *Brassica* transformation in Example 1. Following a co-cultivation period of 3-4 days at 24° C., the hypocotyls were transferred onto selection medium which was MS medium containing 200 mg/l Cefotaxime, 10 mg/l hygromycin, 1 mg/l BAP (6-benzyl-aminopurine) and 0.1 mg/l NAA (napthaleneacetic acid). Shoot development was initiated after about 2 weeks. Shoots were transferred onto fresh MS medium with the same additives except NAA was reduced to 0.02 mg/l. After 2-3 weeks, healthy green shoots were transferred onto fresh MS media without growth regulators for induction of roots. Rooted shoots were planted in potting mix in glasshouse.

The transgenic nature of regenerated flax plants was confirmed by PCR amplification of part of the *Echium* Δ6 fatty acid desaturase sequence with the primers Ed6s1, 5'-ACTCTGTTTCTGAGGTGTCCA-3' (SEQ ID NO:19); and Ed6a1, 5'-CATATTAACCCTAGCCATACACAT-3' (SEQ ID NO:20). DNA extracted from individual, regenerated flax plants was used as template in PCR reactions using the following amplification conditions: denaturation at 94° C. for 2 min, followed by 30 cycles of 94° C. for 40 sec, 58° C. for 40 sec and 72° C. for 1 min. Seeds set on forty primary transgenic flax plants will be analysed for the presence of SDA and GLA using lipid extraction followed by gas chromatography. It is expected that high levels of SDA will be produced in many of the plants and that SDA levels will be greater than GLA levels.

Seed from the transformed flax plants or extracts such as the oil or the seed meal can be used in feed compositions for use in feeding fish or crustacea.

Example 6. Transformation of Cotton with a Seed-Specific Construct Expressing an *Echium* Δ6 Fatty Acid Desaturase Gene Cottonseed normally contains only negligible amounts (<0.5% of total fatty acids) of α-linolenic acid (ALA). In order to produce ALA at increased levels in cottonseed oil, cotton (*Gossypium hirsutum*) was transformed with a seed-specific gene construct expressing a FAD3 gene from *Brassica napus* (Arondel et al., 1992) (encoded protein amino acid sequence provided as SEQ ID NO:27). The accession number of the cDNA clone of this gene was L01418. The full protein coding region of the *B. napus* FAD3 gene was amplified by PCR using the primers BnFAD3-S1, 5'-CTCCAGCGATGGTTGTTGCTAT-3' (SEQ ID NO:21) and BnFAD3-A1, 5'-AATGTCTCTGGTGACGTAGC-3' (SEQ ID NO:22). The PCR product was cloned into a pGEMTeasy® vector (Promega) and the excised by restriction digest with NotI. The *B. napus* FAD3 coding sequence was inserted in the sense orientation into the NotI site between the soybean lectin gene promoter and terminator sequences (Cho et al., 1995), to provide a seed-specific expression construct. This vector contained an NPTII gene conferring kanamycin resistance as a selectable marker for plant transformation. This vector was introduced into *Agrobacterium* and used to transform cotton as described in Liu et al (2002). Independent transgenic plants expressing the FAD3 gene were obtained and lines accumulating ALA retained.

Separate cotton transformation experiments were performed using a similar seed-specific lectin cassette expressing a Δ6 fatty acid desaturase, to convert LA to GLA and ALA to SDA. The full protein-coding region of the Δ6 desaturase from *Echium plantagineum* (Zhou et al., 2006; SEQ ID NO:25) was amplified by PCR using the following primers incorporating a SmaI site at the 5' end, and SacI at the 3' end. Ed6F: 5'-ATCCCCGGGTACCGGTCGCCAC-CATGGCTAATGCAATCAAGAAGTA-3' (SEQ ID NO:30) and Ed6R: 5'-TTGGAGCTCAACCATGAGTAT-TAAGAGCTTC-3' (SEQ ID NO:31). The PCR fragment was cloned into pGEM-Teasy® vector (Promega) and sequenced to ensure no PCR-induced errors were introduced. The PCR amplified Δ6 desaturase gene was subsequently cloned into the corresponding SmaI/SacI sites in a sense orientation behind the napin (Fp1) promoter and upstream of the nos3' terminator-polyadenylation signal. *Agrobacterium tumefaciens* strain AGL1 harbouring the resulted construct, pGNapin-E6D, was used to transform cotton variety Coker315 by the method described by Liu et al. (2002).

Nine fertile independently transformed plants were obtained. The transformed cotton plants were positive for the presence of the transgene, and expression in developing seeds, by PCR and Northern blot analysis of the expressed RNA. 15 individual mature seeds from each of these primary transgenic plants were subjected to the analysis of fatty acid composition using gas chromatography (GC) as described above. Surprisingly high levels of γ-linolenic acid (GLA) were found to accumulate in four transgenic lines, while there was no detectable GLA in the non-transformed control plants. Levels of GLA of greater than 15% were observed in many seeds, and the level reached greater than 25% in some seeds that were likely to be homozygous for the introduced Δ6 desaturase gene. The accumulation of GLA is mainly at the expense of linoleic acid. Indeed, the conversion of LA to GLA (measured as % GLA×100/(% LA+% GLA) in the seedoil) was highly efficient in these cottonseeds relative to seeds of other plants, being greater than 25% in many seed and reaching in excess of 45% in some seed.

Cotton lines containing both genes will be produced by crossing the transformants expressing the FAD3 gene and transformants expressing the Δ6 desaturase gene, to produce lines containing SDA. By the methods described above, oilseed plants such as cotton or flax may be produced which produce at least 5.5% SDA on a weight basis in the fatty acid of the seed oil. Preferably, the level of SDA in the fatty acid is at least 11%, at least 15%, at least 20%, at least 25%, at least 30%, at least 35%, at least 40%, at least 45% or at least 50% on a weight basis. The efficiency of conversion of ALA to SDA (measured as % SDA×100/(% ALA+% SDA) in the seedoil) is at least 25% and preferably at least 45%. That is, at least 25%, preferably at least 45% of the polyunsaturated fatty acid in the cotton or flax seed that has a carbon chain of C18 or longer is desaturated at the Δ6 position.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed above are incorporated herein in their entirety.

This application claims priority from U.S. 60/737,946, the entire contents of which are incorporated herein by reference.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Abbadi et al. (2001) *Eur. J. Lipid. Sci. Technol.* 103:106-113.
Arondel et al. (1992) *Science* 258:1353-1355.
Barlow (2000) *Global Aquac. Advo.* 3: 85-86.
Baumlein et al. (1991) *Mol. Gen. Genet.* 225:459-467.
Baumlein et al (1992) *Plant J.* 2:233-239.
Bell et al. (1993) *Lipids.* 28: 819-826.
Bell et al. (2002) *J. Nutr.* 132: 222-230.
Bell et al. (2003) *J. Nutr.* 133: 2793-2801.
Bell et al. (2004) *Lipids.* 39: 223-232.
Berberich et al. (1998) *Plant Mol. Biol.* 36:297-306.
Bilyeu et al. (2003) *Crop Sci.* 43: 1833-1838.
Bligh and Dyer (1959) *Can. J. Biochem. Physiol.* 37: 911-917.
Bransden et al. (2003) *Comp. Biochem. Physiol. B.* 135: 611-625.
Broun et al. (1998) *Plant J.* 13:201-210.
Browse and Slack (1981) *FEBS Letters* 131:111-114.
Carter et al. (2003) *Mar. Biotechnol.* 5: 480-492.
Cho et al. (1995) *Plant Mol Biol Rep.* 13:255-269.
Cho et al. (1999) *J. Biol. Chem.* 274:471-477.
Chung et al. (1999) *Plant Cell Physiol.* 40: 114-118.
De Block et al. (1989) *Plant Physiol.* 91:694-701.
Domergue et al. (2002) *Eur. J. Biochem.* 269:4105-4113.
Drexler et al. (2003) *J. Plant Physiol.* 160:779-802.
FAO (2001) *Fishery statistics* Vol. 88/2 aquaculture production. FAO Fisheries series No 58/FAO Statistics series No 160. *FAO.* 178.
Fonseca-Madrigal et al. (2005) *Aquac. Nutr.* 11: 241-250.
Gamborg et al. (1968) *Exp. Cell Res.* 50:151-158.
Garcia-Maroto et al. (2002) *Lipids* 37:417-426.
Girke et al. (1998) *Plant J.* 15:39-48.
Guil-Guerrero et al. (2000) *Phytochemistry* 53:451-456.
Hamada et al. (1994) *Gene* 147: 293-294.
Hamada et al. (1996) *Plant Cell Physiol.* 37: 606-611.
Harel et al. (2002) *Aquaculture.* 213: 347-362.
Hastings et al. (2001) *Proc. Natl. Acad. Sci. U.S.A.* 98:14304-14309.
Helland et al. (1996) *Aquaculture.* 139: 157-163.
Hong et al. (2002) *Lipids* 37:863-868.
Horiguchi et al. (1998) *Plant Cell Physiol.* 39:540-544.
Huang et al. (1999) *Lipids* 34:649-659.
Jones and Harwood (1980) *Biochem J.* 190:851-854.
Kajikawa et al. (2004) *Plant Mol Biol* 54:335-352.
Kirsch et al. (1997) *Proc. Natl. Acad. Sci. U.S.A.* 94: 2079-2084.
Leonard, et al. (2000) *Biochem. J.* 347:719-724.
Li et al. (2003) *Plant Cell* 15:1646-1661.
Liu et al. (2002) *Plant Physiol.* 129:1732-1743.
Metz et al. (2001) *Science* 293:290-293.
Meyer et al. (2003) *Biochemistry* 42:9779-9788.
Michaelson et al. (1998) *J. Biol. Chem.* 273:19055-19059.
Morita et al. (2000) *Biochem. Soc. Trans.* 28:872-879.
Murashige and Skoog (1962) *Physiologica Plantarum* 28:147-150.
Napier et al. (1998) *Biochem J.* 330:611-614.
Napier et al. (1999) *Trends in Plant Sci* 4:2-4.
Naylor et al. (2000) *Nature.* 405: 1017-1024.
Needleman and Wunsch (1970)*J. Mol. Biol.* 48:443-453.
Pereira et al. (2004) *Biochem. J.* 378:665-671.
Polvi and Ackman (1992)*J. Agric. Food Chem.* 40:1001-1007.
Qi et al. (2002) *FEES Lett.* 510:159-165.
Qiu et al. (2001)*J. Biol. Chem.* 276:31561-31566.
Radke et al. (1988) *Theor. Appl. Genet.* 75: 685-694.
Reddy et al. (1993) *Plant Mol. Biol.* 22:293-300.
Sakamoto et al. (1997) *Mol. Microbiol.* 23: 1281-1292.
Sakuradani et al. (1999) *Gene* 238:445-453.
Sargent et al. (2002) *The Lipids*, in *Fish Nutrition*, J. E. Halve; Editor. 2002, Academic Press: San Diego. p. 181-257.
Sayanova et al. (1997) *Proc. Natl. Acad. Sci. U.S.A.* 94:4211-4216.
Sayanova et al. (1999) *Plant Physiol.* 121:641-646.
Sayanova et al. (2003) *FEBS Lett.* 542:100-104.
Sayanova and Napier (2004) *Phytochemistry* 65:147-158.
Seierstad et al. (2005) *Euro. J. Clin. Invest.* 35: 52-59.
Sperling et al. (2000) *Eur. J. Biochem.* 267:3801-3811.
Sperling and Heinz (2001) *Eur. J. Lipid Sci. Technol* 103: 158-180.
Sprecher et al. (1995) *J. Lipid Res.* 36:2471-2477.
Spychalla et al. (1997) *Proc. Natl. Acad. Set U.S.A.* 94:1142-1147.
Suga et al. (2002) *Biosci. Biotechnol. Biochem.* 66: 1314-1327.
Takeyama et al. (1997) *Microbiology* 143:2725-2731.
Tanaka et al. (1999) *Biotechnol. Lett.* 21:939-945.
Tang et al. (1999) *Plant Physiol.* 119: 364.
Tanhuanpaa et al. (2002) *Mol. Breed.* 10: 51-62.
Torstensen et al. (2004) *Aquac. Nutr.* 10: 175-192.
van de Loo and Somerville (1994) *Plant Physiol.* 105: 443-444.
Volkman and Nichols (1991) *J. Planar Chromatogr.* 4: 19-26.
Vrinten et al. (2005) *Plant Physiol.* 139: 79-87.
Wallis and Browse (1999) *Arch. Biochem. Biophys.* 365: 307-316.
Wang et al. (1998) *Acta Horticulturae* 461: 401-405.
Wedemeyer 1996. Physiology of Fish in Intensive Culture Systems, Chapman & Hall, New York.
Whitney et al. (2003) *Planta* 217:983-992.
Yadav et al. (1993) *Plant Physiol.* 103: 467-476.
Yamamoto et al. (1992) *Plant Cell Physiol.* 33: 13-20.
Yamazaki et al. (1992) *Biochim. Biophys. Acta.* 1123: 18-26.
Yang et al. (2004) *J. Exp. Bot.* 55: 2251-2259.
Yazawa (1996) *Lipids* 31:S297-S300.
Yu et al. (2000) *Lipids* 35:1061-1064.
Zhang et al. (2004) *FEBS Lett.* 556:81-85.
Zhou et al. (2006) *Plant Sci.* 170:665-673.

The invention claimed is:

1. A fish whose white muscle, red muscle, or white and red muscle long-chain polyunsaturated fatty acid (LC-PUFA) content has been increased by feeding the fish a feedstuff comprising plant oil whose total fatty acid content comprises 5.5% (w/w) stearidonic acid (SDA), wherein the LC-PUFA content of the white muscle, red muscle, or white and red muscle of the fish has been increased relative to the white muscle, red muscle, or white and red muscle, respectively, of a corresponding fish fed a corresponding feedstuff lacking plant oil whose total fatty acid content comprises 5.5% (w/w) SDA.

2. The fish of claim 1, wherein the white muscle, red muscle, or white and red muscle content of docosahexaenoic acid (DHA) in the fish has been increased relative to the white muscle, red muscle, or white and red muscle, respectively, of the corresponding fish.

3. The fish of claim 1, wherein the fish is a salmon.

4. The fish of claim 3, wherein the fish is an Atlantic Salmon.

5. The fish of claim 3, wherein the salmon was fed the feedstuff comprising the plant oil for at least 6 weeks.

6. The fish of claim 3, wherein the salmon was fed the feedstuff comprising the plant oil at a larval or a juvenile stage of development.

7. The fish of claim 1, wherein the feedstuff comprising the plant oil comprises 7.2 g/kg dry matter of SDA.

8. The fish of claim 7, wherein the feedstuff comprising the plant oil comprises 14.3 g/kg dry matter of SDA.

9. The fish of claim 1, wherein the total fatty acid content of the feedstuff comprising the plant oil comprises less than 30% (w/w) total saturated fatty acids (SFA).

10. The fish of claim 1, wherein the total fatty acid content of the feedstuff comprising the plant oil comprises 15% (w/w) α-linolenic acid (ALA).

11. The fish of claim 1, wherein the feedstuff comprising the plant oil comprises 0.1% (w/w) phytosterol, wherein the phytosterol is brassicasterol, campesterol, stigmasterol, β-sitosterol or any combination of these.

12. The fish of claim 1, wherein at least 90% of the SDA in the feedstuff comprising the plant oil is esterified in the form of triacylglycerols.

13. The fish of claim 1, wherein the lipid content of the feedstuff comprising the plant oil is at least 100 g/kg dry matter.

14. The fish of claim 1, wherein:
the total fatty acid content of the white muscle lipid of the fish comprises 18.3% DHA (w/w) and less than 29.6% SFA (w/w);
the total fatty acid content of the red muscle lipid of the fish comprises 9.6% DHA (w/w) and less than 28.2% SFA (w/w); and/or
the total fatty acid content of the white muscle lipid of the fish comprises 2.1% SDA (w/w).

15. The fish of claim 1, wherein the levels of 14:0 fatty acid and 16:0 fatty acid in muscle tissue of the fish are reduced by at least 10% relative to a corresponding fish fed a corresponding feedstuff which comprises fish oil instead of the plant oil whose total fatty acid content comprises 5.5% (w/w) SDA.

16. The fish of claim 1, wherein the fish, after having been fed the feedstuff comprising the plant oil for at least 6 weeks, has about the same weight, specific growth rate, weight gain, total feed consumption, feed efficiency ratio, hepatosomatic index and/or survival when compared with the corresponding fish fed the corresponding feedstuff whose total fatty acid content lacks 5.5% (w/w) SDA.

17. The fish of claim 1, wherein the fish, after having been fed the feedstuff comprising the plant oil for at least 6 weeks, has higher SDA and eicosatetraenoic acid (ETA) levels in muscle tissue when compared with the corresponding fish fed the corresponding feedstuff whose total fatty acid content lacks 5.5% (w/w) SDA.

18. The fish of claim 1, wherein the fish, after having been fed the feedstuff comprising the plant oil for at least 6 weeks, has lower SFA levels in muscle tissue when compared with a corresponding fish fed a corresponding feedstuff which comprises fish oil instead of the plant oil whose total fatty acid content comprises 5.5% SDA.

19. The fish of claim 15, wherein the plant oil comprises canola oil, soybean oil or flax seed oil.

20. The fish of claim 19, wherein the plant oil is from a plant which is genetically modified such that the total fatty acid content of the plant oil comprises 5.5% (w/w) SDA.

21. The fish of claim 1, wherein the feedstuff comprising the plant oil comprises a transgenic organism, or extract or portion thereof, and at least one other ingredient, wherein the organism is genetically modified such that the total fatty acid content of the organism, or extract or portion thereof, comprises 5.5% (w/w) SDA.

22. The fish of claim 21, wherein the organism is yeast.

* * * * *